United States Patent
Fukaya et al.

(10) Patent No.: US 6,613,066 B1
(45) Date of Patent: Sep. 2, 2003

(54) BALLOON CATHETER AND PRODUCTION METHOD THEREFOR

(75) Inventors: Kohei Fukaya, Settsu (JP); Hiromi Maeda, Uji (JP); Takuji Nishide, Settsu (JP); Shogo Miki, Suita (JP); Ryoji Nakano, Settsu (JP); Masato Hashiba, Settsu (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/787,930

(22) PCT Filed: Oct. 5, 1999

(86) PCT No.: PCT/JP99/05467

§ 371 (c)(1),
(2), (4) Date: Apr. 3, 2001

(87) PCT Pub. No.: WO00/20063

PCT Pub. Date: Apr. 13, 2000

(30) Foreign Application Priority Data

| Oct. 5, 1998 | (JP) | 10-282113 |
| Dec. 18, 1998 | (JP) | 10-360641 |
| Dec. 24, 1998 | (JP) | 10-366912 |
| Feb. 1, 1999 | (JP) | 11-023447 |
| Feb. 15, 1999 | (JP) | 11-035251 |
| Mar. 25, 1999 | (JP) | 11-081962 |
| Mar. 26, 1999 | (JP) | 11-084555 |

(51) Int. Cl.$^7$ .................................. A61M 29/00
(52) U.S. Cl. ............... 606/192; 606/194; 606/198; 604/96.1
(58) Field of Search .............. 606/108, 191, 606/192, 194, 195, 198; 604/96.01, 102.9, 102.02, 103.03, 103.04, 103.09, 264, 523, 524, 528, 103.13

(56) References Cited

U.S. PATENT DOCUMENTS 4,276,874 A * 7/1981 Wolvek et al. ............... 600/18
4,315,512 A * 2/1982 Fogarty ........................ 606/194

(List continued on next page.)

FOREIGN PATENT DOCUMENTS

| EP | 0 437 795 A1 | 7/1991 |
| EP | 0 707 865 A1 | 4/1996 |

(List continued on next page.)

*Primary Examiner*—Michael J. Milano
*Assistant Examiner*—Gwen Phanijphand
(74) *Attorney, Agent, or Firm*—Armstrong, Westerman & Hattori, LLP

(57) ABSTRACT

A balloon catheter 1 is configured so as to comprise a catheter shaft 2 formed by joining a proximal-side tubular member 3 and a distal-side tubular member 4, an adapter member 6 connected to the base end of the catheter shaft 2, and a balloon 5 joined to the distal end of the catheter shaft 2. A metal coiled elastic member 10 is deployed in the internal space in the adapter member 6, so that it can move toward the distal end. This coiled elastic body 10 abuts on a ring-shaped wall part 11a formed on the outer circumferential surface of the base end of an elastic force transmitting member 11 and supports the elastic force transmitting member 11 to the distal side. The leading end of a linear member 12 that is one of the components of the elastic force transmitting member 11 reaches to an internal space 5f in the balloon and is bonded to the outer circumferential surface of a guide wire passing tube 7. Thus the elastic supporting force of the coiled elastic body 10 is transmitted via the elastic force transmitting member 11 to the distal-side sleeve part 5d of the balloon 5, and tension is imparted to the balloon 5 in the axial direction.

34 Claims, 32 Drawing Sheets

U.S. PATENT DOCUMENTS

| | | | |
|---|---|---|---|
| 4,998,923 A | * 3/1991 | Samson et al. | 606/194 |
| 5,304,198 A | 4/1994 | Samson | |
| 5,397,306 A | 3/1995 | Nobuyoshi et al. | |
| 5,415,637 A | * 5/1995 | Khosravi | 604/105 |
| 5,632,760 A | 5/1997 | Sheiban et al. | |
| 5,645,789 A | 7/1997 | Roucher, Jr. | |
| 5,674,287 A | * 10/1997 | Slepian et al. | 128/898 |

FOREIGN PATENT DOCUMENTS

| | | |
|---|---|---|
| EP | 0 787 504 A2 | 8/1997 |
| JP | 63-277062 | 11/1988 |
| JP | 3-188875 | 8/1991 |
| JP | 6-292727 | 10/1994 |
| JP | 8-206217 | 8/1996 |
| JP | 8-257128 | 10/1996 |
| JP | 9-192227 | 7/1997 |
| JP | 9-271517 | 10/1997 |
| JP | 9-509860 | 10/1997 |
| JP | 10-33681 | 2/1998 |
| JP | 10-506315 | 6/1998 |
| JP | 10-179754 | 7/1998 |
| JP | 10-179756 | 7/1998 |
| JP | 10-234845 | 9/1998 |
| WO | WO 94/11047 | 5/1994 |
| WO | WO 95/23619 | 9/1995 |
| WO | WO 97/03716 | 2/1997 |

* cited by examiner

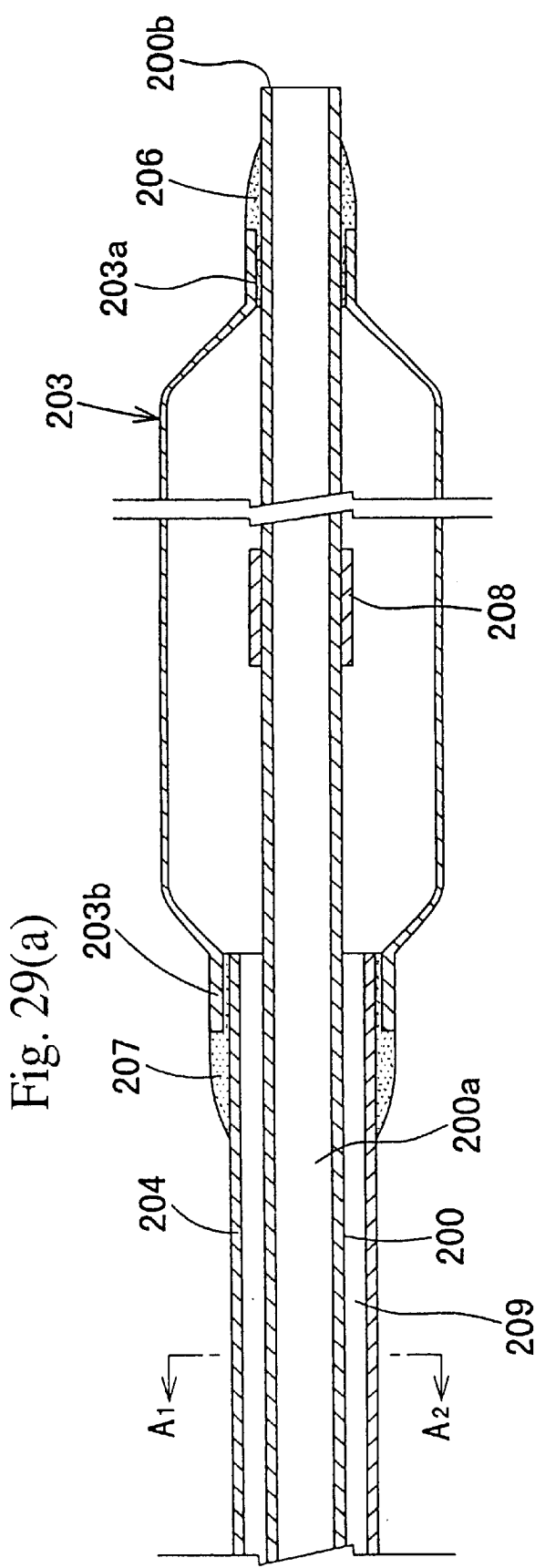
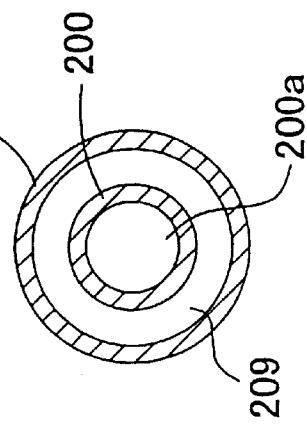
Fig. 29(a)
Fig. 29(b)

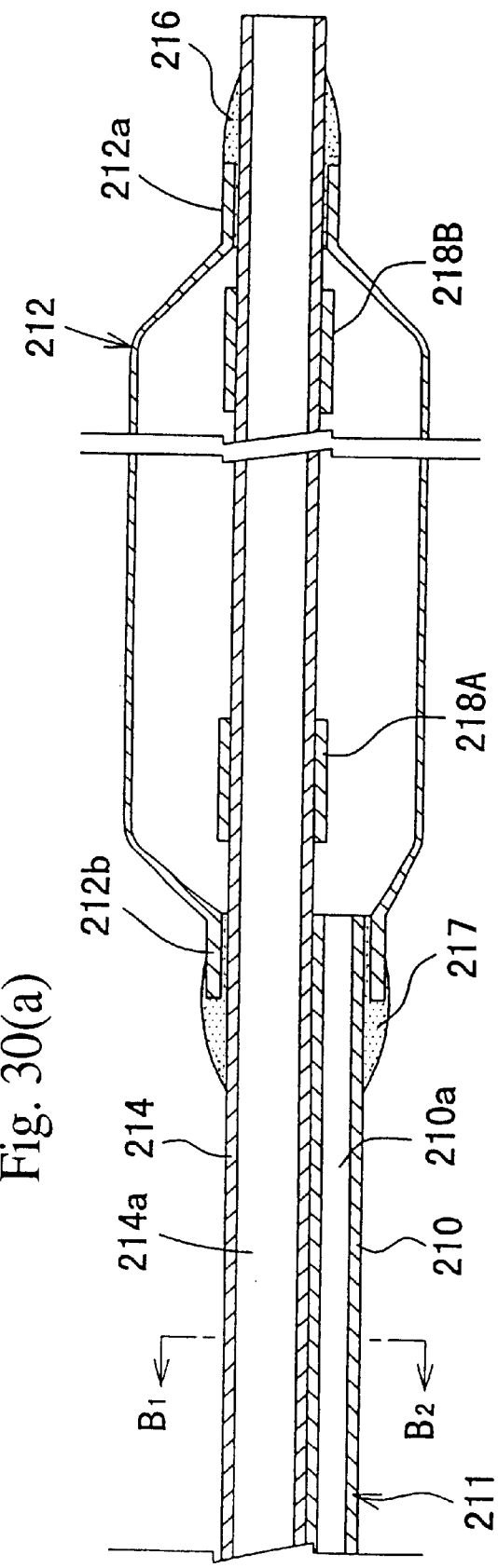

BALLOON CATHETER AND PRODUCTION METHOD THEREFOR

BACKGROUND OF THE INVENTION

1. Field of the Invention

This invention relates to a balloon catheter used primarily in medical treatment and surgery for the purpose of dilating lesion sites such as strictures or blockages in passages in the body, and more particularly to a balloon catheter, and method for manufacturing a balloon catheter, used in percutaneous translumin angioplasty (PTA) or percutaneous translumin coronary angioplasty (PTCA), which are treatments for dilating lesion sites such as strictures or blockages in coronary arteries, extremital arteries, kidney arteries, and peripheral blood vessels, etc.

2. Description of the Related Art

The common balloon catheter is formed by joining a balloon that is expanded and contracted by adjusting the internal pressure therein to the distal end of a catheter shaft, wherein, in the interior of the catheter shaft, are formed, extending in the axial direction thereof, a lumen (guide wire lumen) for inserting therein a guide wire, and a lumen (inflation lumen) for passing a pressurized fluid that is supplied for adjusting the inner pressure in the balloon. Using such a balloon catheter as this, angioplasty is performed according to the procedure now described. First, the guide wire passed through the guide wire lumen is made to pass through the stricture or other lesion site, the balloon is inserted into the body along that guide wire and made to coincide with the lesion site, a pressured fluid such as a suitably diluted shadow-casting agent is supplied through the inflation lumen to the balloon, the balloon is caused to expand, and the lesion site is subjected to dilation therapy. After the lesion site has been subjected to the dilation therapy, the balloon is first made to contract by reducing the pressure therein and folded, and then removed from the body, whereupon the angioplasty is finished.

Such balloon catheters as these are divided into two types, namely in over-the-wire type balloon catheter wherein a tube 200 for passing the guide wire is deployed so that it reaches from an adapter member 202 connected to the base end of the catheter shaft 201 to the distal end of the balloon 203, as exemplified in FIG. 27, and a rapid exchange type balloon catheter wherein a tube 210 for passing the guide wire is deployed so that its reach is limited from midway along the catheter shaft 211 to the distal end of the balloon 212, as exemplified in FIG. 28. In FIG. 27 and 28, the distal part containing the balloon is represented slightly enlarged over the near portion to facilitate understanding.

The over-the-wire balloon catheter diagrammed in FIG. 27 is configured with a catheter shaft 201 formed by the joining of a tube 204 on the distal side and a tube 205 on the proximal side, a balloon 203 joined to the distal end of the tube 204 on the distal side, and the adapter member 202 joined at the base end of the tube 205 on the proximal side.

The structure of the distal part of such a balloon catheter is exemplified in FIG. 29(a). The guide wire passing tube 200 having a guide wire lumen 200a is passed through the inner space of the balloon 203. The inner circumferential surface of a sleeve part 203a on the distal side of this balloon 203 and the outer circumferential surface of the guide wire passing tube 200 are joined concentrically with an adhesive 206. And the inner circumferential surface of a sleeve part 203b on the proximal side of the balloon 203 and the outer circumferential surface at the distal end of the outside tube 204 are joined concentrically with an adhesive 207. Symbol 208 in this figure designates a radiopaque marker. Also, as diagrammed in the $A_1$–$A_2$ cross-section in FIG. 29(b), the guide wire passing tube 200 and outside tube 204 are deployed concentrically, and an inflation lumen 209 for passing the pressurized fluid supplied to the balloon 203 is formed between the inner surface of the outside tube 204 and the outer surface of the guide wire passing tube 200. Although, in this example, the guide wire passing tube 200 and outside tube 204 are deployed concentrically, there are also configurations wherein the outer circumferential surface at the distal end of the guide wire passing tube 200 is bonded securely to the inner surface of the outside tube 204 so that the guide wire passing tube 200 will not move backwards relative to the outside tube 204 such that the relative position therebetween shifts greatly.

There is also another distal part structure, such as exemplified in FIG. 30. According to FIG. 30, a guide wire passing tube 214 configuring a guide wire lumen 214a and an inflation tube 210 configuring an inflation lumen 210a are deployed in parallel. As diagrammed in the $B_1$–$B_2$ cross-section in FIG. 30(b), both tubes are secured by a heat-shrunk tube 215 to configure a catheter shaft 211. Also, the inner circumferential surface of the sleeve part 212a is bonded to the outer circumferential surface on the distal end of the guide wire passing tube 214 with an adhesive 216, and the inner circumferential surface of the sleeve part 212b on the proximal side of the balloon 212 and the outer circumferential surface of the catheter shaft 211 are bonded with an adhesive 217. The symbols 218A and 218B in this figure indicate radiopaque markers. There is yet another distal part configuration, such as that diagrammed in FIG. 31. In the $C_1$–$C_2$ cross-section in FIG. 31(b) is diagrammed a catheter shaft 211 consisting of a single-structure tube-shaped member 219 comprising a guide wire shaft 214 and inflation lumen 219a internally.

The rapid exchange type balloon catheter diagrammed in FIG. 28, on the other hand, has a catheter shaft 211 comprising a tube shaped member, configured such that the balloon 212 is joined to the distal end of that catheter shaft 211, the adapter member 213 is joined to the base end of the catheter shaft 211, and a guide wire passing tube 210 also deployed in the distal part.

In general, in the interest of smooth insertion into a passage in the body and reaching the most distant site along that internal passage, balloon catheters having smaller outer diameters are advantageous. That being so, unused balloon catheters are commonly provided in a condition wherein the balloon has been made to contract under reduced pressure and folded up to minimize the outer diameter of the balloon.

The properties required as minimal limitations in such balloons are (1) that they be able to withstand pressures sufficiently so that they do not burst when the inner pressure is increased by a pressurized fluid, (2) that they exhibit a predetermined relationship between the expanded outer diameter and the expansion pressure (expansion characteristics), and (3) that the strength of the balloon in the circumferential direction and axial direction be calculated in a balanced manner so that the balloon can exhibit deformation so as to conform to winding internal passages when expanded. It is also preferable that the skin thickness of the balloon itself be as thin as possible in order to make the outer shape of the balloon small when it is folded up.

Balloon catheters, moreover, are often used a number of times for the same lesion site. In such cases, from the perspective of reintroducing the balloon catheter, it is important that the balloon exhibit the property of being able to retain well the condition wherein it is made to contract under reduced pressure and folded up (folded shape retention characteristics). Also, the skin thickness of the straight tubular part of the balloon should be as thin as possible so that it has a small outer diameter in the folded condition, and the skin thickness in the conical parts or sleeve parts of the balloon should also be as thin as possible, for the same reasons, but also to realize good reintroduction performance toward the lesion site when reused. That the balloon exhibit good fold-up retention, thin skin in the straight tubular part, and thin skin in the sleeve parts is equally important from the perspective of retracting the balloon easily from the internal passage after the lesion site has been subjected to dilation therapy.

However, conventional balloon catheters are inadequate, for the two reasons stated below, in terms of their performance in being reintroduced to a lesion site and in terms of the ease of retracting the balloon from the internal passage following dilation therapy. The first reason is that, although the balloons are subjected to a heat treatment to cause them to remember and retain the condition wherein they are folded up, it is very difficult to maintain the folded condition retention properties and memory properties in these balloons. The balloon is formed from a polymer material, and therefore is inferior in terms of shape retention and shape memory, and that shape retention and shape memory are the more lost the higher the internal pressure to which the balloon is subjected during treatment is made. The shape retention and shape memory of the balloon are largely dependent on the material of which the balloon is made and the skin thickness thereof. As that skin thickness is made thinner, shape retention and shape memory decline very rapidly. When the shape retention and shape memory of the balloon have declined, after it has been expanded, it will not return to a folded condition even when made to contract but, as diagrammed in the side elevation in FIG. 32(*a*) and the $D_1$–$D_2$ cross-section in FIG. 32(*b*), the balloon 220 joined to the guide wire passing tube 221 and outside tube 222 form flat wings 220*a* and 220*b*, the outer diameter of the balloon 220 takes on maximum width, and, simultaneously, the controllability of the balloon catheter declines markedly due to the hard wings 220*a* and 220*b*. Accordingly, a design is desired wherewith, after insuring satisfactory basic performance in the balloon, the balloon configuring material can be made as pliable as possible, with the skin thickness made thin, so that, even if wings are formed in the balloon, the controllability thereof can be prevented from declining. Conversely, however, when the highest priority is placed on balloon folded shape retention and shape memory, and the balloon skin thickness is made thicker than necessary, the folded shape thereof does not stabilize, the sleeve parts of the balloon become thick at the same time, and it becomes markedly more difficult both to reinsert the balloon to the lesion site and to retract the balloon from the internal passage after treatment.

The second reason is that, when the balloon is caused to contract by reducing the pressure therein, wrinkles 223 are formed in the outer surface of the balloon 220 wherein wings 220*a* and 220*b* have formed, in an angular direction that is at right angles to or nearly at right angles to the axial direction of the catheter. When the balloon contracts in this condition with the wrinkles 223 developed therein, it becomes easier for the wings described above to form, and, at the same time, the wrinkles function just like a framework, and the wings are readily formed in a flat shape, as diagrammed in FIG. 32(*b*). The primary cause of the development of such wrinkles is that the relative deployment relationship between the guide wire passing tube and the balloon is not maintained as it should be. In a balloon catheter structured such that the guide wire passing tube 200 is deployed concentrically inside the outside tube 204, as diagrammed in FIG. 29, for example, when the balloon catheter is being pushed ahead inside an internal passage and advanced to a lesion site, when a resistance force is encountered at the leading end of the balloon catheter, that resistance force acts on the tip 200*b* of the guide wire passing tube 200, and the guide wire passing tube moves backward relative to the outside tube 204. Thereupon, the balloon 203 can do nothing but absorb the positional discrepancy between the two tubes, resulting in wrinkles forming in the balloon 203. When the balloon 203 is expanded with a high pressure, the balloon 203 extends in the axial direction, but, at the same time, a pulling force in the axial direction also acts on the guide wire passing tube 200 that is passing through the interior of the balloon, whereupon the guide wire passing tube 200 is pulled out from the outside tube 204 on the distal side. When the balloon 203 is made to contract under reduced pressure in this condition, there is too much length in the guide wire passing tube 200 inside the balloon 203, and the guide wire passing tube 200 can do nothing but effect a snaking movement. As a result, the ability of the guide wire to pass through declines, the refolding properties decline, and the wrinkles described above develop. Such a phenomenon as this can occur in the balloon catheters diagrammed in FIG. 30 and FIG. 31 as well as in the balloon catheter diagrammed in FIG. 29. More specifically, with the balloon catheters diagrammed in FIGS. 30 and 31, because the guide wire passing tube and inflation tube are joined, when the balloon is expanded under high pressure, the guide wire passing tube extends inside the balloon, and, when the balloon is made to contract under reduced pressure, there is too much length in the guide wire passing tube, and snaking results.

In the foregoing, the structure demanded in the far portion of the balloon catheter containing the balloon, and the problems therewith, are described, but good following or conforming properties and controllability are demanded in a balloon catheter so that the manipulations of a technician on the base end are communicated well to the leading end of the balloon catheter. Therefore, the catheter shaft of a balloon catheter is commonly configured such that tubular members are connected, using a comparatively flexible tubular member in the far portion and a tubular member that is stiffer than that of the far portion in the near portion. However, when tubular members having different rigidity are connected together, there is a strong likelihood that breakage or bending will occur at that connection, a likelihood that is particularly strong in slender structures like catheters. That being so, tubular members having extremely different rigidity are not used, and it has been necessary to effect such measures as (1) to connect a plurality of tubular members having gradually different rigidity in multiple stages, (2) to reinforce the connection between the tubular members using a reinforcing material, or (3) to use a tapered tubular member wherewith the rigidity is made to continuously vary. When a plurality of tubular members having gradually different rigidity are connected in multiple stages, a material limitation arises per force in that a material exhibiting rigidity close to that required must be selected. This is a problem in that, as a result, it is difficult to secure the desired controllability. When the tubular member connections are reinforced with a reinforcing material, great care must be taken with respect to the dimensions of the reinforcing material so that the outer diameter of the catheter is not made too large by that reinforcing material and so that interior space (for the lumens, etc.) can be adequately secured. In addition to that, in some cases, the bond between the reinforcing member(s) and the stiff tubular member on the proximal side becomes very hard and catheter controllability declines. The method of using a tapered tubular member and continuously varying the rigidity thereof is an excellent method, but requires an enormous amount of labor to fabricate the tapered tubular member, and it is difficult to fabricate products of stable quality.

Now, conventionally, as means of enhancing the controllability of balloon catheters, and particularly the controllability when the balloon catheter is passed through winding internal passages, methods have been employed such as applying a coating to the far portion of the catheter, using a lubricant consisting of silicon oil or a fluorine resin, or applying a hydrophilic coating that can activate the surface so that it is lubricated when wetted. A hydrophilic coating is particularly beneficial from the standpoint of durability and low friction relative to winding internal passages. The method almost always adopted in hydrophilic coatings capable of activating the surface so that it is lubricated when wetted is that of forming a surface by bonding polymer materials exhibiting water solubility or hydrophilia, and derivatives thereof, to a base material on the surface constituting the target. When this method is applied to the distal part of a balloon catheter, the hydrophilic coating will also be applied to the balloon. However, in order to secure good controllability and good advancing properties in the internal passage, the balloon should be administered in a state wherein it has been conditioned to fold-up. When the hydrophilic coating described above is applied to such a balloon, the hydrophilic coating acts just as an adhesive, whereupon the balloon clings in the folded state, so that the balloon becomes incapable of expanding. This problem is caused by moistening when the catheter is subjected to ethylene oxide gas sterilization or by the moisture in the atmosphere when in storage, and develops when the water soluble or hydrophilic polymers configuring the hydrophilic coating exhibit adhesion, and the surfaces of the folded balloon that have been given the hydrophilic coating contact each other and stick to each other. Also, when surfaces that have been given a high-density hydrophilic coating stick to each other, there have been times when the coating peels off. In order to suppress these problems, it is necessary to lower the density of the hydrophilic coating administered to the balloon. When the density of the hydrophilic coating is lowered, however, adequately low friction properties cannot be imparted to the catheter surface, making it very difficult to secure good controllability in winding internal passages, which was the original objective.

Conventionally, moreover, hydrophilic coatings have been applied only to the far portions of balloon catheters, but there are cases where, in actual use, performance is greatly affected not only by the friction between the catheter and the internal passage, but also by friction between the catheter and other items used together therewith, such as treatment instruments. The procedure used when performing vasodilation therapy on coronary arteries is described below as an example. The balloon catheter is led into the coronary artery through a guiding catheter that is first deployed from a femoral artery or humeral artery, through the aorta, to the vicinity of the entrance to the coronary artery. The guiding catheter, however, is formed so as to be bent in a particular shape, so that the leading end of the guiding catheter on the distal side, and the leading end orifice thereof, can be more easily deployed at the entrance to the coronary artery, in view of the fact that the aorta bends sharply at the aortic arch.

When the balloon catheter encounters intense friction at the bent portion of the guiding catheter, and particularly when the comparatively stiff proximal-side tube of the balloon catheter is located in that bent portion, the controllability of the balloon catheter declines markedly. Also, when the outer diameter of the proximal-side tube configuring the catheter shaft is larger than the tube on the distal side, the friction becomes great between the large diameter portion of that proximal-side tube and the bent portion of the guidance catheter, and the controllability of the balloon catheter declines markedly.

There are also cases, relating to a different phenomenon than that described above, where, when treating lesions at vascular branches or branching lesions, multiple balloon catheters are simultaneously passed through the same guidance catheter and deployed in the coronary artery. The friction naturally becomes great between the balloon catheters and the guidance catheter or between the balloon catheters themselves during such procedures, whereupon the controllability of the balloon catheters deteriorates. This phenomenon is also now a problem. In a recent trend, moreover, guidance catheters of smaller diameter are being used in an increasing number of cases due to the increase in the use of approaches from the humeral artery. More specifically, there is a gradually increasing trend in the use of the 6 Fr size over the conventional 7 or 8 Fr size. This means that the trend is toward increasing the friction with the balloon catheter that is passed therethrough. It also means, in cases where the outer diameter of the near-portion tube is larger than the outer diameter of the far-portion tube, that the friction between the near-portion tube and the small-diameter guidance catheter will become greater.

Also, various materials are being used for the catheter shaft, depending on the performance demanded, but synthetic resin materials which combine flexibility and machinability are used most widely. However, in cases where it is particularly desired to make the configuration stiff on the technician's end, as described in the foregoing, and in cases where it is desired to prevent squashing by pressure from internal tissue or treatment instruments used concurrently, a tubular member made of metal has been used as part of the configuring material of the balloon catheter. When a metal tubular member is used as a configuring member of the balloon catheter, however, the metal is generally readily susceptible to plastic deformation, and a residual bending tendency is readily assumed, wherefore, once a deformation has been imparted for some reason, the bent condition becomes perpetuated. As a result, many cases have been observed where the balloon catheter could not thereafter be used, or the controllability thereof deteriorated markedly.

Next, the conventional balloon and the problems therewith are described. As described in the foregoing, the properties required as minimal limitations in balloons include, (1) that they be able to withstand pressures sufficiently so that they do not burst when the inner pressure is increased by a pressurized fluid, and (2) that they exhibit a predetermined relationship between the expanded outer diameter and the expansion pressure (expansion characteristics). The expanded outer diameter relative to each nominal pressure determined within a range extending roughly from 4 atmospheres (approximately 0.4 MPa) to 10 atmospheres (approximately 1 MPa) is called the "nominal expanded diameter." When using a balloon catheter, a suitable balloon is selected according to the diameter of the internal passage at the treatment site, giving consideration to the nominal expanded diameter and the expansion characteristics. As described earlier, it is better if the balloon skin thickness is thin, and it is particularly important that the tip of the balloon catheter that becomes the leading end have a small outer diameter and be flexible in order to pass through internal passages of high curvature and pass ahead of lesion sites that are highly constricted or occluded. Also, the tip is generally formed such that it is fused or bonded concentrically to the guide wire passing tube and the sleeve part on the distal side of the balloon, but, irrespective of the bonding or fusing, it is obvious that the tip will have a narrower diameter and be more flexible the thinner the skin thickness of the distal-side sleeve part.

Balloons of various nominal expanded diameters are usually provided in accordance with the diameters of the internal passages. In the manufacture of such balloons, in order to manifest the ability to withstand pressure and accurate expansion characteristics expected in the balloon, tubular members (parisons) having a predetermined shape for each nominal expanded diameter are prepared, and stretching processing is performed with magnitudes corresponding to the nominal expanded diameters. For most of those stretching processes, a blow molding method is adopted wherein metal molds are used which have cavities corresponding to the nominal expanded diameters. Thus, when the balloon is formed with the nominal expanded diameter as a reference criterion, (1) it is necessary, in order to secure pressure withstanding performance, to make the skin thickness of the straight tube portion of a balloon of large nominal expanded diameter slightly thicker than in a balloon of small nominal expanded diameter, and (2) it is necessary to make the skin thickness of the tubular member that constitutes the raw material synergistically greater because, as the nominal expanded diameter becomes greater, the amount of stretching increases. Accordingly, when the skin thickness of the tubular member is increased as the nominal expanded diameter is made larger, the skin thickness of the straight tube part of the balloon increases, while the skin thickness in the sleeve parts becomes extremely thick, thicker than the skin thickness of the straight tube part where there is only a small factor of stretching in the circumferential dimension, whereupon both diameter narrowing and flexibility are lost. When high-strength material is used, on the other hand, the skin of the straight tube part can be made thin, and the skin thickness of the sleeve parts naturally also becomes thinner to some extent, but, because the high-strength material is used, the sleeve parts are rigidly hard, whereupon flexibility is lost. If follows that there is room for improvement in terms of balloon strength to withstand pressure, and the balance between the skin thickness of the straight tube part and the skin thickness of the sleeve parts.

Also, as described earlier, in order to realize good controllability in winding internal passages and good transiting characteristics at highly constricted lesion sites, as required in a balloon catheter, it is important to make the diameter of the tip of the balloon catheter smaller and to enhance flexibility. For that reason, even more diameter narrowing and flexibility enhancement in the distal-side sleeve part that forms the tip are strongly desired. However, when balloons are formed using the blow method, it is necessary to use resin materials having intermolecular forces suitable to blow molding, and there are often limitations on the fluidity of the resin material during molding, wherefore it has been very difficult to freely make the skin thickness of the sleeve part thinner.

To date, a number of methods have been developed relating to effecting thinner skin thickness and high strength in balloons. In Japanese Patent Application Laid-Open No H3-37949/1991 (title of invention: "Thin-Skin, High-Strength Balloon and Manufacture Thereof"), a balloon made from polyethylene terephthalate (PET) is disclosed. This balloon realizes thin skin and high strength, and excels in dimensional stability. Nevertheless, it suffers the shortcomings of lacking flexibility and being susceptible to pinhole failure. With pinhole failure, in particular, if the balloon fails inside a blood vessel, the vascular wall is subjected locally to high stresses, and there is an extremely high danger of damaging the vascular wall, wherefore this is undesirable.

In Japanese Patent Application Laid-Open No. H7-178174/1995 (title of invention: "Base Tube and Balloon Catheter"), moreover, a balloon is disclosed wherein thinner skin and higher strength are realized, and dimensional variation during expansion is suppressed, by fiber-reinforcing the base tube. With this method, however, the base tube becomes a three-layer structure, making it very difficult to achieve skin thickness thinning, particularly in the base tube of a balloon of small diameter, as a result whereof it is very difficult to form a balloon having a thinner skin thickness. In other words, this can hardly be called an ideal method for realizing the thin-skin balloons currently demanded where medical treatments are performed. The fact that the method of fabricating the base tube is complex presents a further problem in the production area.

As means for effecting both thinner skin and high strength in balloons, furthermore, balloons are made multi-layer using multiple polymer materials. In Japanese Patent Application Laid-Open No. H9-164191/1997, for example, a multi-layer balloon is disclosed wherein are used flexible polymers exhibiting an elongation at the break point near that of high-strength polymers. And in Japanese PCT Patent Application Laid-Open (KOHYO) No. H9-506008/1997, a balloon is disclosed that is based on a combination of a thermoplastic elastomer and a non-flexible-structure polymer material. In these multi-layer balloons, balloons are realized that exhibit high strength while retaining flexibility, but peeling between the respective layers is a worry. Compared to a single-layer tube, moreover, the process of extruding a multi-layer tube is generally more complex, which gives rise to problematic cost disadvantages.

As is evident from the examples of the prior art described in the publications noted above, while the disclosed balloon manufacturing methods do impart outstanding characteristics to the balloon, they nevertheless cause other problems, and hence cannot be called completely satisfactory methods.

SUMMARY OF THE INVENTION

An object of the present invention, in view of the several problems noted in the foregoing, is to provide a balloon catheter and method for manufacturing same wherewith (1) when the balloon is made to contract under reduced pressure and put in a folded condition again, after a lesion site has been subjected to dilation therapy, wrinkles are prevented from occurring in the balloon by favorably maintaining the folded shape retention and shape memory of the balloon, and favorably maintaining the relative deployment relationship between the balloon and the guide wire passing tube that passes through the interior of the balloon, (2) outstanding controllability is exhibited because well-balanced rigidity is effected from the proximal part to the distal part of the catheter shaft, (3) stickiness does not occur in the balloon in the folded condition even when a hydrophilic coating is applied to the far portion of the catheter, within a prescribed range, and adequate wear resistance is imparted thereto, (4) in cases where a tubular member made of a metal is used as a catheter shaft configuring member, performance deterioration is not brought about by plastic deformation in the metal tubular member, (5) a balloon is realized wherein the diameter thinning, and flexibility of the tip of the balloon catheter can be enhanced while retaining adequate ability to withstand pressure, and (6) a balloon is realized wherewith it is possible to make the skin thinner while retaining adequate ability to withstand pressure, and which exhibits flexibility such that insertion to a bent lesion site is made easy.

In order to achieve the object stated above, a first invention is a balloon catheter for use in therapy and surgery the purpose whereof is a dilation operation, configured with a balloon deployed on the distal end of a catheter shaft, comprising tension generation means for generating a tension in the axial direction of the balloon.

Here, it is desirable that there be a guide wire passing tube that passes through the interior of the balloon at the distal part of the catheter and that joins the distal end of the balloon, and that a tension be generated in the axial direction of the balloon by the application of a force in the axial direction at the distal part of the guide wire passing tube by means of the tension generation means.

It is also permissible to first join a non-tensioned guide wire passing tube to the distal end of the balloon and then assemble the balloon catheter in a condition wherein a force is applied in the axial direction to the distal part of that guide wire passing tube by the tension generation means.

A second invention is a balloon catheter for use in therapy and surgery the purpose whereof is a dilation operation, configured with a balloon deployed on the distal end of a catheter shaft, comprising a function for suppressing the generation of wrinkles oriented at angles perpendicular or nearly perpendicular to the axial dimension of the balloon when the balloon is caused to contract after expansion.

For the tension generation means described above and for specific means for realizing the wrinkle generation suppression function described above, it is preferable to use an elastic body that is incorporated in the interior of the balloon catheter. A favorable specific example of this elastic body is a coiled elastic body made of metal or the like.

It is also permissible that the balloon catheter have an elastic force transmitting body inside it that is supported by the elastic body, whereby a tension is imparted to the balloon in the axial direction through that elastic force transmitting body.

Furthermore, it is preferable that the elastic force transmitting body noted above comprise, as a configuring component, a linear member that extends to the vicinity of the balloon. It is also preferable that at least a portion of the linear member exhibit a tapered shape.

Another favorable configuration is one wherein the linear member is joined to one end of the coiled elastic body, and is deployed so as to extend from the interior of that coiled elastic body to the balloon.

It is also desirable that the stress generated by displacements in the elastic body be adjusted to within a range of 5 gf to 200 gf, inclusively, but preferably within a range of 10 gf to 50 gf, inclusively, in order to generate the desired tension in the balloon. By "stress" here in the present invention is meant the force (in units gf) that acts, when an elastic body is displaced, in a direction opposite the direction of that displacement.

The catheter shaft noted above should be formed from multiple tubular members having at least one lumen, wherein the rigidity in the proximal part and distal part of the catheter shaft are mutually different, and the rigidity of that proximal part is set higher than that of the distal part. More specifically, catheter shafts wherein the proximal part thereof is configured with a polyimide material as the main component and the distal part thereof is formed from a polymer material having a lower modulus of elasticity than the polyimide, or wherein the proximal part thereof is formed from a metal material and the ,distal part thereof is formed from a polymer material, are highly suitable.

Furthermore, when applying a hydrophilic coating to the distal part of such a catheter shaft, it is preferable to set the hydrophilic coating range so that it extends to the proximal part of the catheter shaft that contacts the distal part thereof, and/or to set the hydrophilic coating range so that it extends to the proximal part of the catheter shaft configured with a larger diameter than the distal part thereof.

Furthermore, in order to adjust the rigidity of the catheter shaft and enhance the controllability of the balloon catheter, the flexibility of the catheter shaft may be varied from the distal part to the proximal part, either in multiple stages or continuously.

Furthermore, in a so-called rapid exchange type balloon catheter wherein the formation of a guide wire lumen for passing the guide wire is limited to extend from the distal end to midway along the catheter shaft, it is preferable that a hydrophilic coating be applied to the outer surface of the catheter shaft from the leading end of the balloon catheter to a site that is more to the proximal side than the back end opening of the guide wire lumen, it being particularly desirable to apply the hydrophilic coating in a range that extends from the farthest end of the balloon catheter to a point that is at least 300 mm on the proximal side thereof.

When applying the hydrophilic coating to the catheter shaft and balloon in the distal part of the balloon catheter, it is better to adjust the thickness of the hydrophilic coating layer on that catheter shaft so that it is greater than the thickness of the hydrophilic coating layer on the balloon and near the balloon, and to adjust the friction resistance of the hydrophilic coating layer of the catheter shaft when wetted so that it is smaller than the friction resistance at the balloon and near the balloon. Here, it is better to adjust the thickness of the hydrophilic coating layer of the catheter shaft to be 2 $\mu$m or greater.

Alternatively, such a hydrophilic coating may be applied only to the catheter shaft in the distal part of the balloon catheter.

One method of applying a hydrophilic coating to the balloon catheter in this manner comprises a process step for coating a hydrophilic polymer solution onto the balloon and catheter shaft in the distal part of the balloon catheter, a process step for coating and washing the balloon or the balloon and the vicinity of that balloon with a hydrophilic polymer solution of weaker concentration, and a process step for fixing the hydrophilic polymer to the balloon catheter. Another method comprises a process step for coating a hydrophilic polymer solution onto the balloon and catheter shaft in the distal part of the balloon catheter, a process step for washing the balloon or the balloon and the vicinity of the balloon with a solvent that dissolves that hydrophilic polymer solution, and a process step for fixing the hydrophilic polymer onto the balloon catheter.

Now, in a balloon catheter wherein a metal tubular member is used for at least one of the plurality of tubular members configuring the catheter shaft, in order to prevent a decline in performance due to the plastic deformation of the metal tubular member or members, it is desirable that (1) when such metal tubular member is bent 90 degrees with a radius of curvature that is 50 times the outer diameter thereof, held in that condition for 1 minute, and then released, the bend angle produced in that metal tubular member is 15 degrees or less, or (2) when such metal tubular member is bent 90 degrees with a radius of curvature that is 35 times the outer diameter thereof, held in, that condition for 1 minute, and then released, the bend angle produced in that metal tubular member is 30 degrees or less, or, alternatively, (3) when such metal tubular member is bent 90 degrees with a radius of curvature that is 25 times the outer diameter thereof, held in, that condition for 1 minute, and then released, the bend angle produced in that metal tubular member is 35 degrees or less.

For the material used in such metal tubular members, specifically, materials which contain molybdenum or titanium, or stainless steel selected from among 316 stainless steel, 321 stainless steel, and 430F stainless steel, are preferable.

An example of a favorable form for the balloon described in the foregoing is a balloon having a straight tube part, two conical parts, formed at either end of the straight tube part, tapered so that the diameter thereof becomes increasingly smaller toward the outer end thereof, and two cylindrical sleeve parts formed at the two ends of those conical parts, wherein the skin thickness has been adjusted so that the skin thickness ratio ($W_B/W_A$) between the skin thickness of the straight tube part ($W_A$) and the skin thickness of the sleeve part ($W_B$) is less than 2.5 for a balloon nominal expanded diameter of 3.5 mm to 3.0 mm, that skin thickness ratio ($W_B/W_A$) is less than 2.3 for a balloon nominal expanded diameter of 2.5 mm, that skin thickness ratio ($W_B/W_A$) is less than 2.1 for a balloon nominal expanded diameter of 2.0 mm, and that skin thickness ratio ($W_B/W_A$) is less than 2.0 for a balloon nominal expanded diameter of 1.5 mm.

A good raw material for such balloons is a thermoplastic resin exhibiting a Shore hardness greater than 75D, elongation of less than 250%, and a glass transition temperature of less than 37° C.

In making the skin thickness thinner in the sleeve part, in particular, it will be well to stretch the tubular member that is the balloon raw material in the axial direction, form it into a balloon by causing it to stretch in the circumferential dimension by blowing, load the straight tube part and conical parts of the balloon into a metal mold while introducing a higher pressure than that occurring during the stretching in the circumferential dimension into the interior of the balloon to thin the skin thickness of the sleeve parts, and stretching the sleeve parts in the axial direction. It is also permissible, however, alternatively to thin the skin thickness of the sleeve parts of the balloon by polishing or grinding.

Furthermore, it is preferable that the balloon described in the foregoing be configured from a polymer material having a crystallized region, and that the crystallinity of the balloon be adjusted to between no less than 10% and no greater than 40%. For a specific method of manufacturing a balloon having such crystallinity as that, first, the balloon is molded by biaxial stretch blow molding a single-lumen tube molded by extrusion molding and exhibiting an elongation of 250 to 450% at the tensile break point, and is then annealed at a temperature that is 10 to 40° C. higher than the biaxial stretch blow molding temperature, preferably for 40 to 120 seconds.

BRIEF DESCRIPTION OF THE DRAWINGS

FIG. 29($a$) is a simplified cross-sectional view of the leading end of a common balloon catheter, while FIG. 29($b$) is the $A_1$–$A_2$ cross-section thereof;

FIG. 30($a$) is a simplified cross-sectional view of the leading end of a common balloon catheter, while FIG. 30($b$) is the $B_1$–$B_2$ cross-section thereof;

DESCRIPTION OF THE PREFERRED EMBODIMENTS

The present invention is now described in detail, referencing the attached drawings.

Figure 1:
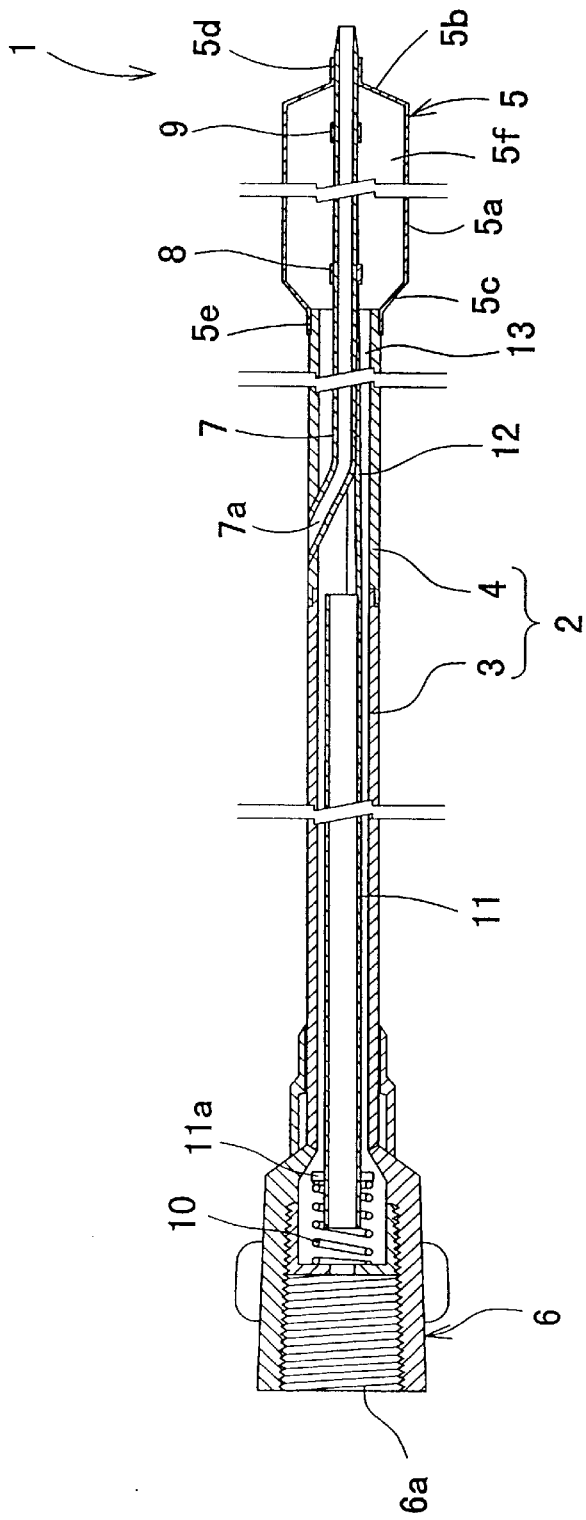
FIG. 1 is a simplified cross-sectional view of a first embodiment of a rapid exchange balloon catheter relating to the present invention.
Figure 2:
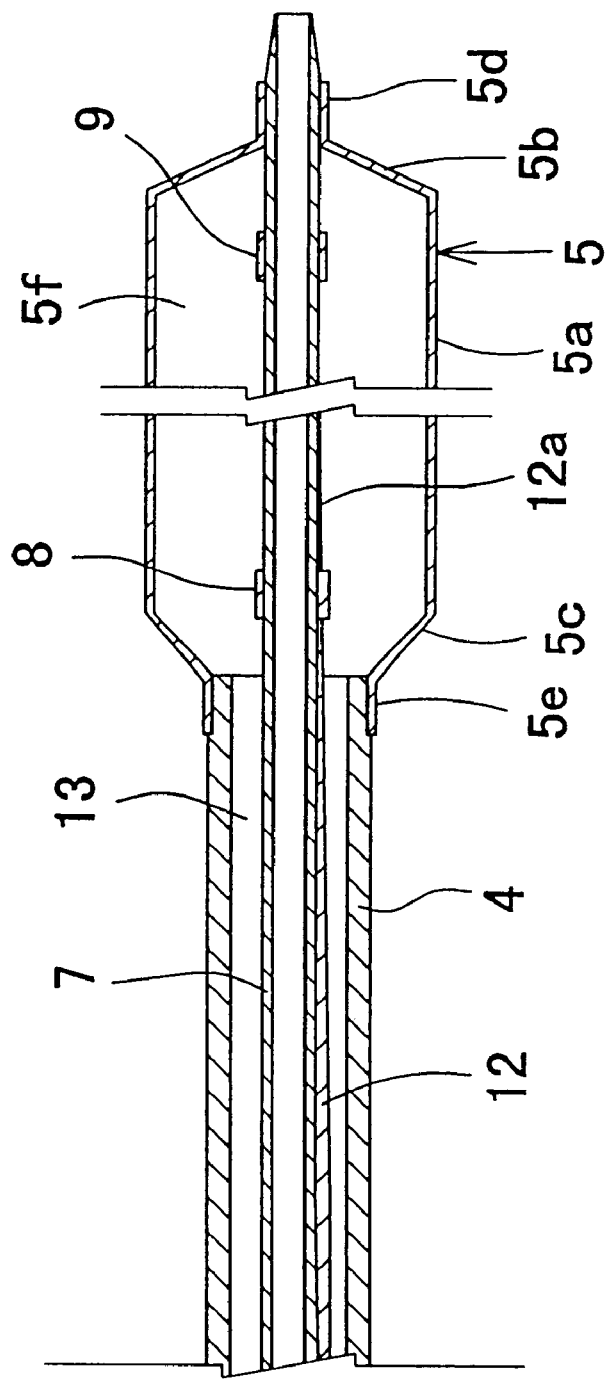
FIG. 2 is an enlarged view of the distal part of the balloon catheter diagrammed in FIG. 1

FIG. 1 is a simplified cross-sectional view of a first embodiment of a rapid exchange balloon catheter relating to the present invention. FIG. 2 is an enlarged view of the distal part of the balloon catheter of this embodiment. The balloon catheter 1 in this embodiment comprises a catheter shaft 2 formed by joining a proximal-side tubular member 3 and a distal-side tubular member 4, a balloon 5 joined to the distal end of the catheter shaft 2, and an adapter member 6 provided with a pressurized fluid induction port 6$a$ for supplying a pressurized fluid to the balloon 5 connected to the base end of the catheter shaft 2. In the present invention, moreover, the term. "near" designates the direction toward the adapter member having either a pressurized fluid induction port connected to an inflation lumen, or a port connecting to a guide wire lumen, communicating with the balloon, relatively in the catheter. The term "far" designates the direction toward the balloon, relatively, in the catheter.

The balloon 5 is formed from a straight tube part 5$a$, a distal-side conical part 5$b$ and a proximal-side conical part 5$c$, formed at either end of the straight tube part 5$a$, tapering so that the diameters thereof become progressively smaller toward the outer ends thereof, and a distal-side sleeve part 5$d$ and a proximal-side sleeve part 5$e$ formed at the two ends of those conical parts 5$b$ and 5$c$. The inner circumferential surface of the proximal-side sleeve part 5$e$ is joined to the outer circumferential surface at the distal end of the distal-side tubular member 4.

In the vicinity of the proximal end of the distal-side tubular member 4, that is, midway along the catheter shaft 2, a back end opening 7$a$ is formed for a guide wire passing tube 7. That guide wire passing tube 7 passes from the back end opening 7$a$ through the lumen in the distal-side tubular member 4 and the internal space in the balloon 5, and extends on to the distal-side sleeve part 5$d$ that is the forward end of the balloon 5 where the inner circumferential surface of the distal-side sleeve part 5$d$ is joined to the outer circumferential surface of the guide wire passing tube 7. Symbols 8 and 9 in FIG. 1 indicate radiopaque markers that are secured to the outer circumferential surface of the guide wire passing tube 7.

In the internal space in the adapter member 6, furthermore, a coiled elastic body 10 made of a metal is deployed, in a condition wherein the back end thereof is supported, and such that it can move in the axial direction. This coiled elastic body 10 abuts a ring-shaped wall piece 11$a$ formed in the outer circumferential surface in the proximal part of an elastic force transmitting member 11 and supports the elastic force transmitting member 11 toward the distal end. This elastic force transmitting member 11, furthermore, has a linear member 12 as one of its configuring components. The leading end 12$a$ of that linear member 12 reaches the internal space 5$f$ in the balloon 5 and is bonded to the outer circumferential surface of the guide wire passing tube. Thus the supporting stress of the coiled elastic body 10 is communicated by the elastic force transmitting member 11 to the distal-side sleeve part 5$d$ of the balloon 5. As a consequence, the distal end of the balloon is in a condition wherein it is pushed out in the near direction, and a pulling stress acts at both the near and distal ends of the balloon 5, wherefore a tension will be imparted to the balloon 5 in the axial direction.

Thus a tension can be generated in the axial direction of the balloon 5 by the tension generation means comprising the elastic body 10 and the elastic force transmitting member 11, when the balloon 5 is made to contract under reduced pressure, after subjecting the lesion site to dilation therapy, and again put in a folded condition, it is possible to favorably maintain the folded shape retention and shape memory of the balloon 5, and to favorably maintain the relative deployment positioning relationship between the balloon 5 and the guide wire passing tube 7 that passes through the space 5$f$ in the interior of the balloon. Furthermore, by the tension generation means in this embodiment, when the balloon 5 is made to contract under reduced pressure, after being expanded, the development of wrinkles in a direction perpendicular to the axial direction of the balloon 5 or in an angular direction close to a perpendicular direction thereto can be suppressed.

Furthermore, the tension generation means relating to the present invention is neither limited to or by that of this embodiment, nor subject to any particular limitation. It is also possible, for example, to suitably select the material and dimensions of the guide wire passing tube, support that guide wire passing tube in the axial direction by the elastic body, and impart tension in the axial direction to the balloon, or to provide a structure such that a contractive force acts on a part or the whole of the tubular member or members configuring the catheter shaft, pull the distal end of the balloon in the axial direction, and impart tension to the balloon in the axial direction.

Such a tension in the axial direction may be imparted to the balloon when the balloon catheter is assembled, but a structure is also permissible wherewith the stress produced by the elastic body acts only during use. By "during use" here is meant the time from the insertion of the balloon catheter into the body until it is removed therefrom. It is particularly preferable that the tension on the balloon in the axial direction be generated when the balloon is being contracted, after it has been expanded, because that makes the shape of the balloon when folded up again good, and is advantageous when reintroducing the balloon of the balloon catheter to the lesion, when extracting it from the internal passage after treatment, and when reusing it after it has been removed for a time from inside the body.

Also, the deployment position of the elastic body described above in the interior of the balloon catheter is in no way limited to or by this embodiment, and may be suitably determined, near the balloon or in the middle part of the catheter shaft, etc., so that a balance is achieved in the balloon catheter between good shape and flexibility.

The properties of the elastic body 5 should be selected so as to maintain good overall balance in the tension on the balloon and the various properties of the balloon catheter. Nevertheless, in order to cope with various processes on the balloon catheter after assembly and shape variation in the balloon catheter resulting from storage and the like, it is preferable that assembly be effected so that the displacement in the elastic body is 1 mm or greater, and the elastic body should be capable of generating, by that displacement, a stress of approximately 5 gf to 200 gf, but preferably of 10 gf to 50 gf, in order to generate some degree of tension in the balloon.

As to the shape and characteristics of the elastic force transmitting body, the method of connecting it to other members, and the places where connected, furthermore, a shape should be selected such that the flow of the pressurized fluid supplied to the balloon is not interfered with, and such that the flexibility of the distal part of the catheter is not impaired. It is possible to use a metal linear member having an outer diameter of 0.02 mm to 0.15 mm at the distal part of the catheter, a tapered metal linear member that has a larger diameter than that at the proximal end, which diameter gradually becomes larger as the proximal side is approached, or a metal cylindrical structure, or a metal columnar structure having a C-shaped cross-section. A metal cylindrical structure or a metal columnar structure having a C-shaped cross-section is particularly desirable because there are cases where that will be advantageous in terms of the flow characteristics of the pressurized fluid supplied to the balloon.

A more specific embodiment of the balloon catheter of the first embodiment described in the foregoing is now described in detail.

EMBODIMENT 1

The balloon catheter of Embodiment 1 is a balloon catheter having the structure diagrammed in FIG. 1, as noted earlier, comprising a polycarbonate adapter member 6, a proximal-side tubular member 3 made of a polyimide that communicates with the pressurized fluid induction port 6a, a distal-side tubular member 4 made of a polyethylene, and a guide wire passing tube 7 deployed inside the inflation lumen 13 that passes through the interior of the lumen 5 to form a concentric shape. A metal linear member 12 is also provided in the distal part, while the proximal part is made of metal and a cylindrical elastic force transmitting member 11 is deployed inside the catheter shaft 2. The leading end 12a of the linear member 12 passes through a cut-in part (not shown) in the radiopaque marker and is bonded to the external surface of the guide wire passing tube 7. The elastic body 10 is deployed so that it can apply an axially directed stress to the elastic force transmitting member 11 when no internal pressure is being applied to the balloon 5. Before it was used, the balloon was subjected to a folding heat treatment and the folded condition was memorized to maintain foldability, and then the balloon 5 was sterilized with ethylene oxide gas. The nominal expanded diameter of this balloon is 3.0 mm.

EVALUATION OF EMBODIMENT 1

Figure 3:
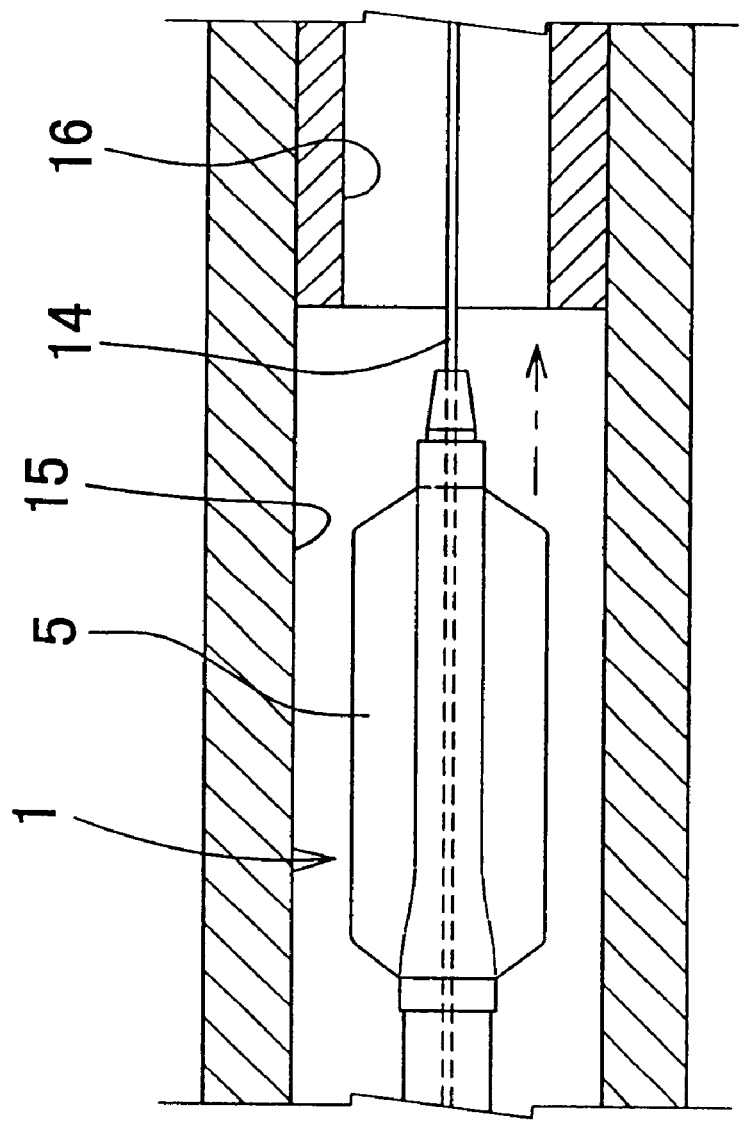
FIG. 3 is a simplified diagram of a test system for demonstrating the controllability of a balloon catheter.

The balloon catheter of Embodiment 1 was evaluated using the test system diagrammed in FIG. 3. Specifically, a core material 14 was inserted into and passed through the guide wire passing tube, a negative pressure was applied to the balloon 5, causing it to contract, and the load acting on the balloon catheter was measured when the leading end of the balloon catheter 1 with wings formed therein was advanced in a narrow-diameter tube 16 (inner diameter 2.0 mm) deployed inside a tube 15 having a comparatively thick inner diameter (3.5 mm).

According to the results, with Embodiment 1, when the balloon was caused to contract after being expanded, tension developed in the axial direction of the balloon, wherefore no wrinkles developed in directions roughly perpendicular to the axial direction, and as a consequence of the balloon being made to contract with folds produced parallel to the catheter axial direction, the balloon portion could easily be advanced inside the narrow-diameter tube 16 in 10 cases out of 10.

Figure 33:
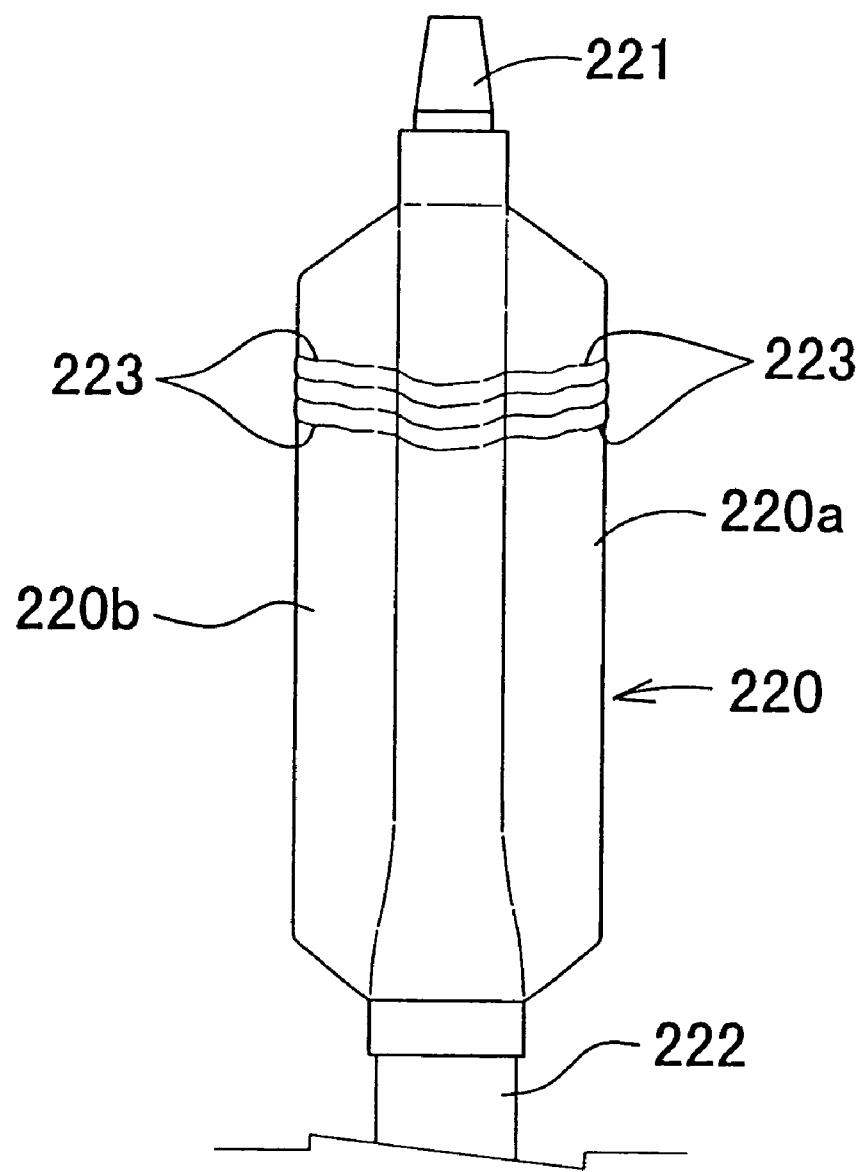
FIG. 33 is a simplified diagram showing a condition wherein wrinkles have formed in a roughly perpendicular direction relative to the axial dimension of wings which have developed in a balloon.

A comparative example (balloon nominal expanded diameter=3.0 mm) provided with no tension generation means was prepared. When this was evaluated similarly with the test system, when the balloon was made to contract after being expanded, the folded shape did not stabilize, a condition was observed wherein wrinkles developed at right angles to the axial direction of the wings, as diagrammed in FIG. 33 (conventional diagram), and the balloon could not be advanced in the narrow-diameter tube 16 in 5 cases out of 10.

Figure 4:
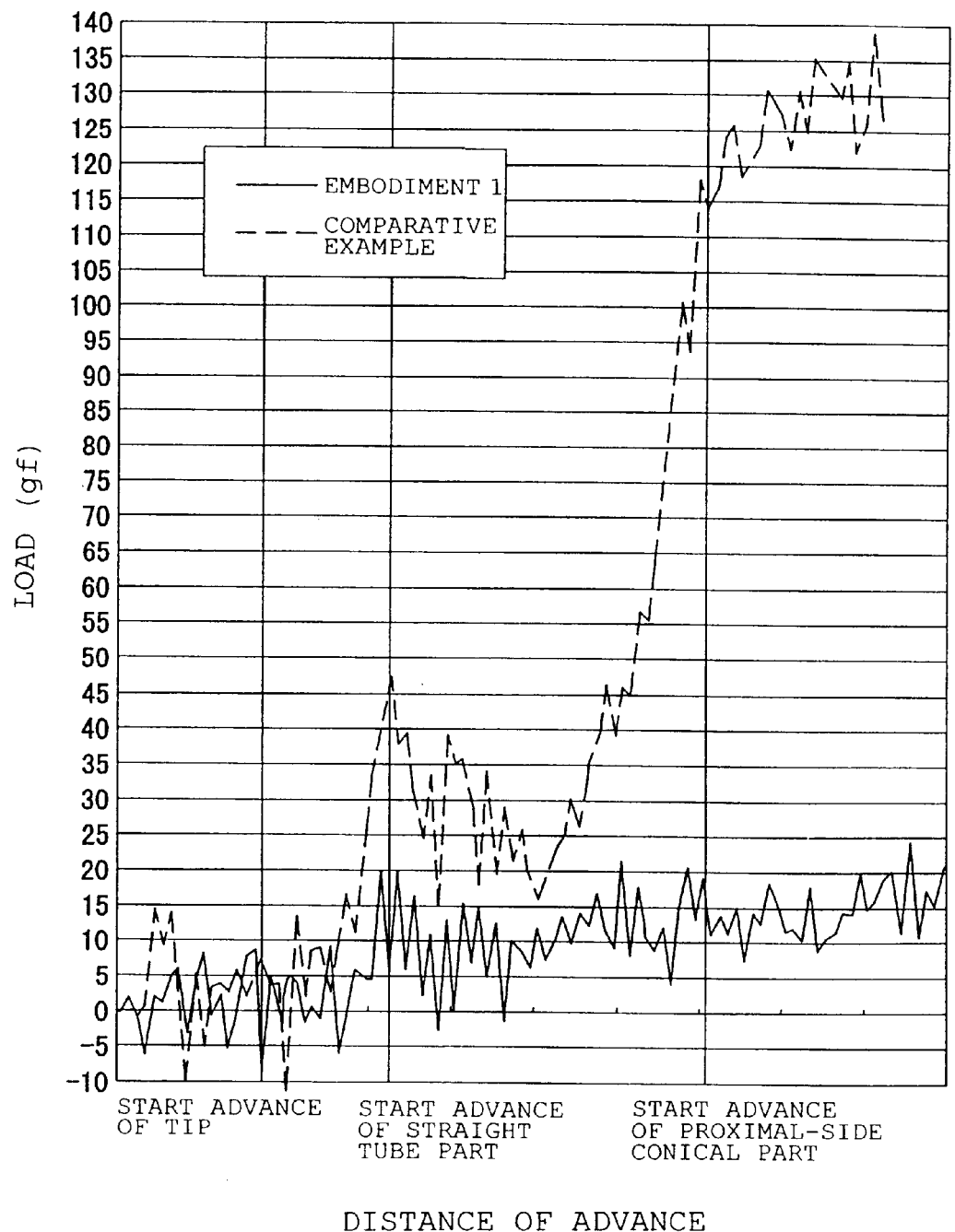
FIG. 4 is a graph representing the results of testing balloon catheters in the test system diagrammed in FIG. 3.

The loads acting on the balloon catheters of Embodiment 1 and the comparative example were graphed, as shown in FIG. 4. In FIG. 4, the "load" acting on the balloon catheter is plotted on the vertical axis and the "advance distance" of the balloon is plotted on the horizontal axis. When evaluations are made at several points in time, namely at the balloon's "foremost end (tip) advance start," "straight tube part advance start," and "proximal-side conical part advance start" times, with Embodiment 1, a slight resistance develops from the point in time where the straight tube part of the balloon is advanced into the narrow-diameter tube, but, with the comparative example, even when it was possible to advance the balloon into the narrow-diameter tube, a greater resistance developed from the point in time where the straight tube part of the balloon was advanced into the narrow-diameter tube than with Embodiment 1, as is indicated in the graph.

Thus, with the balloon catheter of Embodiment 1, a tension is produced in the balloon in the axial direction, wherefore wrinkles do not develop at right angles to the axial direction of the catheter, and, as a consequence of folds being produced parallel to the axial direction of the catheter and the balloon being caused to contract and folded up, the balloon catheter in Embodiment 1 exhibits outstanding characteristics of redeployment to lesion sites and outstanding ease of balloon retraction from inside internal passages after treatment, thus exhibiting extremely favorable characteristics as a balloon catheter.

Figure 5:
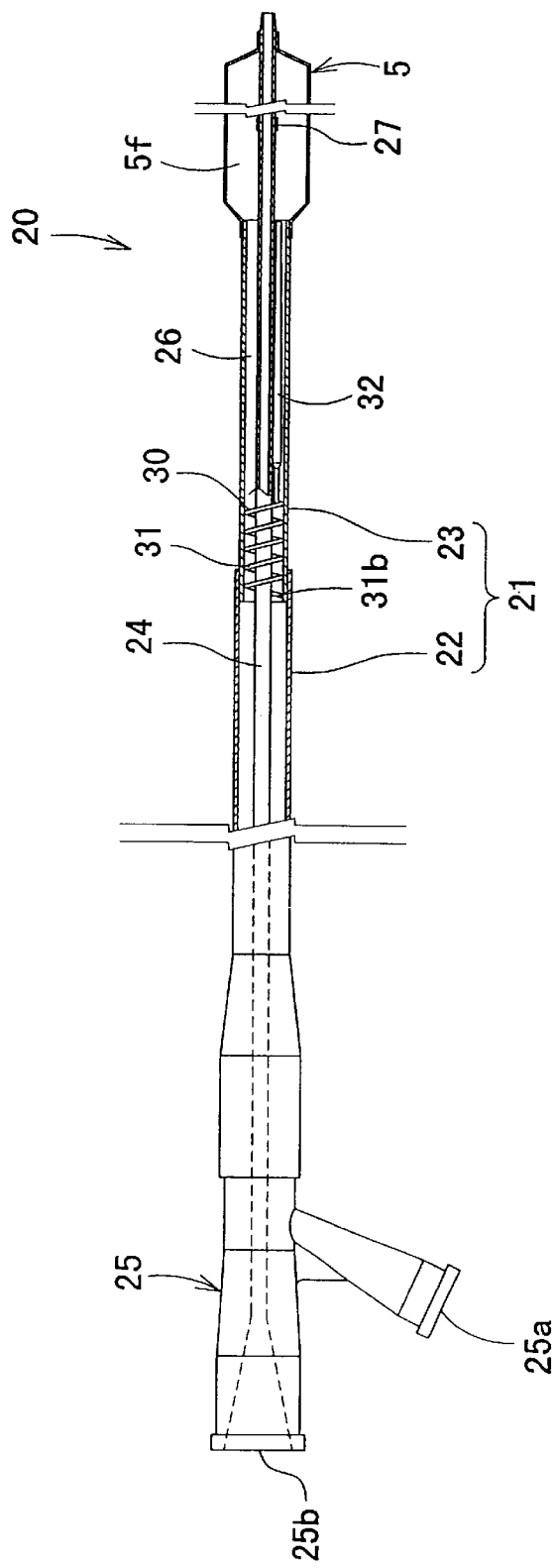
FIG. 5 is a simplified cross-sectional view of a second embodiment of a balloon catheter relating to the present invention.

A balloon catheter in a second embodiment relating to the present invention is described next. FIG. 5 is a simplified cross-sectional view of an over-the-wire type balloon catheter that is the second embodiment. The balloon catheter 20 in this embodiment is configured such that it comprises a catheter shaft 21 wherein a proximal-side tubular member 22 and a distal-side tubular member 23 are fit together and joined concentrically, in the interior whereof a guide wire passing tube 24 is deployed, an adapter member 25 joined to the base end of that catheter shaft 21, and a balloon 5 joined to the distal end of the catheter shaft 21. The adapter member 25 is provided with a guide wire insertion port 25b and a pressurized fluid induction port 25a that communicates with an inflation lumen that passes the pressurized fluid supplied to the balloon 5. In FIG. 5, furthermore, symbol 27 indicates a radiopaque marker secured to the outer circumferential surface of the guide wire passing tube 24. That, i.e. the balloon, which is denoted by the same symbol as noted in the foregoing has roughly the same structure and is not further described here.

Figure 6:
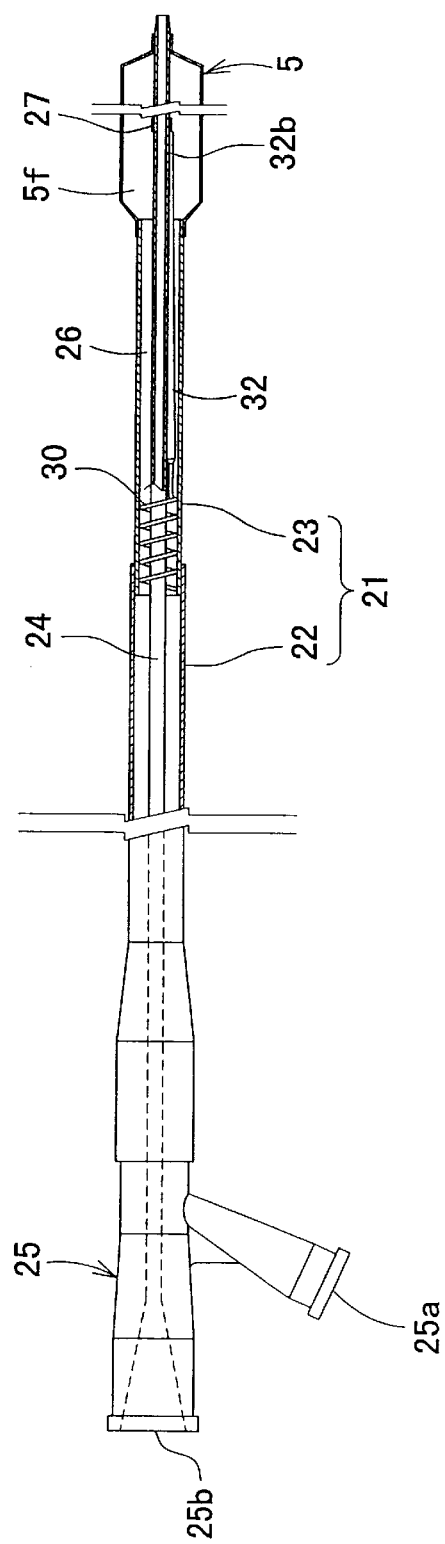
FIG. 6 is a simplified cross-sectional view of a modification of the balloon catheter of the second embodiment.
Figure 7:
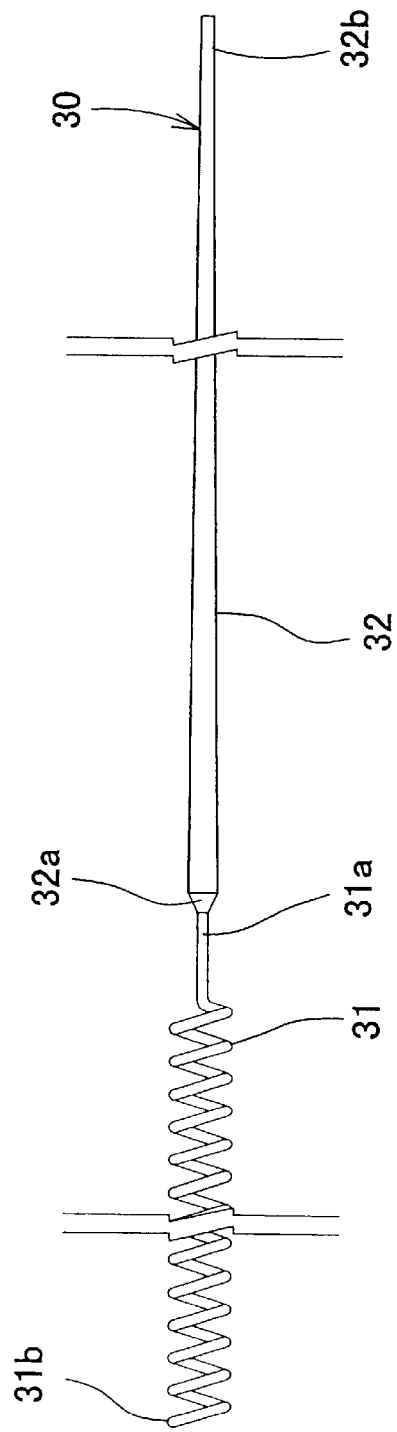
FIG. 7 is a simplified side view of one embodiment of tension generation means relating to the present invention.

In this embodiment, in the interior of the distal-side tubular member 23, tension generation means 30 are provided, configured such that the back end 32a of a linear member 32 having a tapered shape wherewith the diameter gradually decreases as the leading end is approached is joined to one end 31a of a coiled elastic body 31, as diagrammed in FIG. 7. As diagrammed in FIG. 6, the coiled elastic body 31 of the tension generation means 30 is deployed in the interior of the distal-side tube 23, and passed through the guide wire passing tube 24, the linear member whereof is deployed so that it extends to the vicinity of the balloon 5. The back end 31b of the coiled elastic body 31 is bonded securely to the inner circumferential surface of the proximal end of the distal-side tubular member 23, wherefore the linear member 32 can be elastically supported by the coiled elastic body 31 in the distal direction. The leading end 32b of the linear member 32 is joined to the outer) circumferential surface of the guide wire passing tube 24, making it possible to impart tension to the balloon 5 in the axial direction, with the leading end of the guide wire passing tube 24 elastically supported in the distal direction. By deploying such tension generation means inside the catheter, moreover, it becomes possible to continuously vary the rigidity of the catheter shaft from the proximal part (proximal-side tubular member) to the distal part (distal-side tubular member), so catheter controllability improves.

Here, in FIG. 6, a modification of the balloon catheter of this embodiment is exemplified. This modification is roughly the same as the embodiment described above, excepting in that the linear member 32 is longer than in the embodiment described above, the leading end 32b thereof intrudes into the internal space 5f of the balloon 5, and the leading end 32b thereof and the outer surface of the guide wire passing tube 24 are joined. By deploying the leading end 32b of the linear member 32 more to the distal side in this manner, stress from the elastic body is more readily communicated to the leading end of the balloon 5, which in some cases is preferable from the perspective of preventing the guide wire passing tube 24 from excessively snaking inside the catheter after the balloon 5 has been expanded under high pressure and then made to contract so that guide wire controllability is adversely affected.

Figure 8:
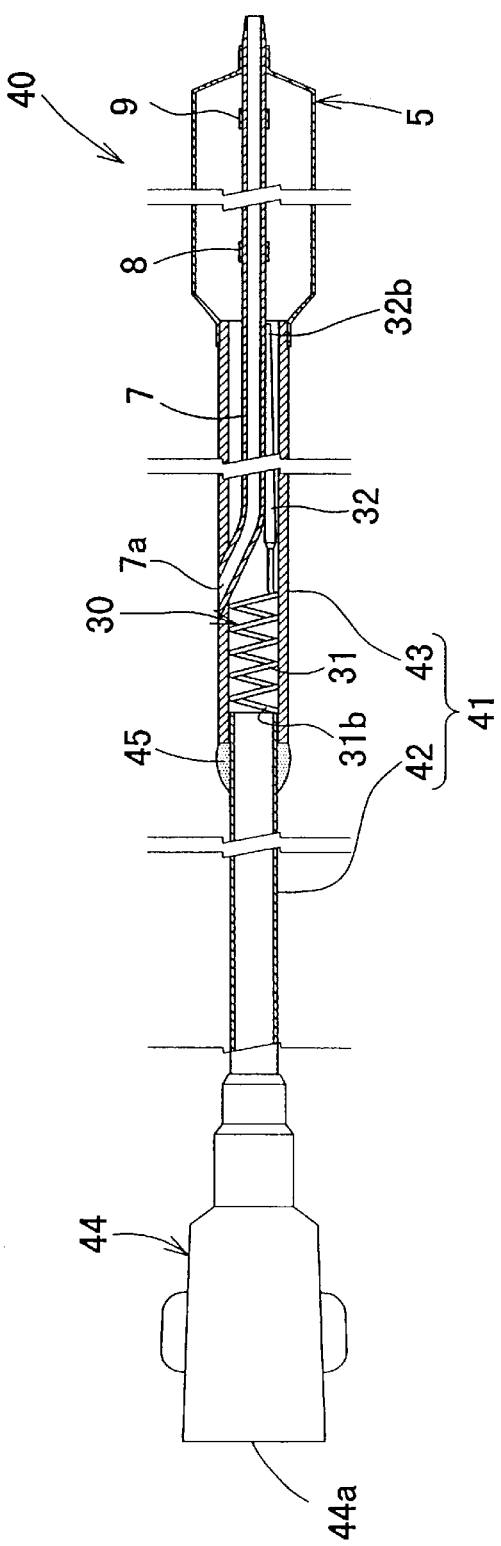
FIG. 8 is a simplified cross-sectional view of a third embodiment of a balloon catheter relating to the present invention.

A balloon catheter in a third embodiment relating to the present invention is next described. FIG. 8 is a simplified cross-section of a rapid exchange type balloon catheter that is the third embodiment. In this embodiment, while this is a rapid exchange type, the same as in the first embodiment diagrammed in FIG. 1, it differs from the first embodiment in that a metal tubular member is used for the proximal-side tubular member. The balloon catheter 40 in this embodiment is configured such that it comprises a catheter shaft 41 wherein a proximal-side tubular member 42 made of a metal and a distal-side tubular member 43 made of a resin are fit together and joined concentrically, an adapter member 44 joined to the base end of that catheter shaft 41, and a balloon 5 joined to the distal end of the catheter shaft 41. In FIG. 8, furthermore, what are denoted by the same symbols as noted in the foregoing have roughly the same configuration and so are not described in detail here.

In this embodiment, the distal end of the metal tubular member 42 is fit to the inner circumferential surface of the proximal end of the distal-side tubular member 43 made of resin and bonded using an adhesive 45. The back end 31b of the coiled elastic body 31 diagrammed in FIG. 7 abuts the distal end of that distal-side tubular member 43. Meanwhile, the leading end 32b of the linear member 32 that is joined to the front end of this coiled elastic body 31, extending to the distal side, contacts the outer circumferential surface of the guide wire passing tube 7. Thus the discontinuity of rigidity between the distal-side tubular member 43 made of resin and the metal tubular member 42 is considerably moderated. As a modification of this embodiment, a balloon catheter is exemplified, as diagrammed in FIG. 9, wherein a linear member 32 is used which is formed longer than in the embodiment. This linear member 32 is deployed to the distal side, passing through a cut-in (not shown) made in the radiopaque marker 8 in the internal space 5f of the balloon 5, and the leading end 32b thereof is joined to the outer surface of the guide wire passing tube 7.

Figure 11:
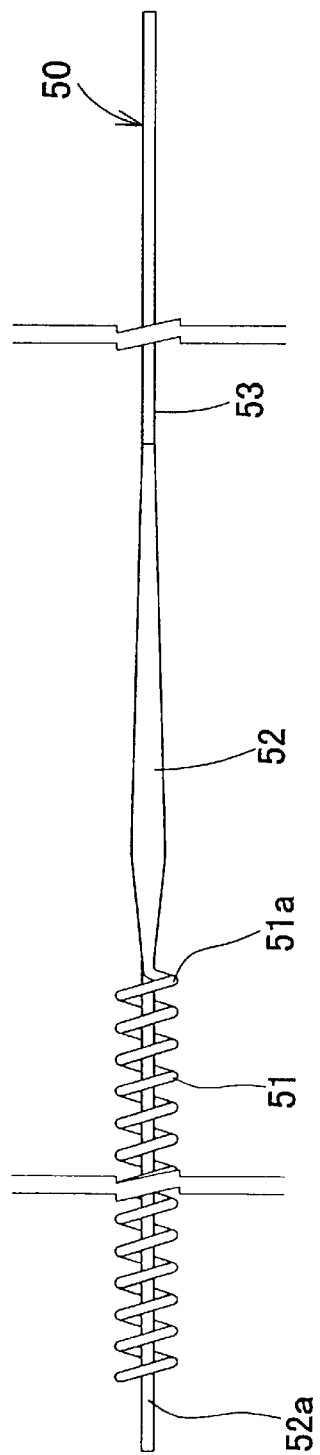
FIG. 11 is a simplified side view of another embodiment of tension generation means relating to the present invention.

In the second embodiment and third embodiment described in the foregoing, tension generation means such as are diagrammed in FIG. 7 are always used. However, instead thereof, a configuration is preferable, in a rapid exchange type balloon catheter, wherein the linear member is comprised of a proximal part 52 and a distal part 53, as diagrammed in FIG. 11, joined to one end 51a of the coiled elastic body 51, and wherein one end 52a of the proximal part is deployed so as to extend, passing through the interior of that coiled elastic body 51, because the coiled elastic body 51 is then reinforced and protected. It is also preferable that the elastic body described above be deployed in a condition wherein displacement therein is possible, and it is better, to the extent possible, that the elastic body not be secured or connected to, the tubular members configuring the catheter shaft. As to the shape of the elastic body in the present invention, as exemplified in the embodiments described above, a coil shape is to be preferred in the interest of preventing failure and deformation in the transition portion between the proximal part and distal part of the catheter shaft, and in the interest also of moderating rigidity discontinuity in that transition portion.

The characteristics of such an elastic body should be selected so as to favorably maintain an overall balance between the tension imparted to the balloon in the axial direction and suitable properties in the balloon catheter. In order to cope with various processes on the balloon catheter after assembly and shape variation in the balloon catheter resulting from storage and the like, the balloon catheter should be assembled so that the displacement in the elastic body is made 1 mm or greater, and the elastic body should be capable of generating, by that displacement, a stress within a range of approximately 5 gf to 200 gf, but preferably of 10 gf to 50 gf, in order to generate some degree of tension in the balloon.

As to the shape of the linear member described above, moreover, the linear member is deployed inside the inflation lumen, wherefore a shape should be selected wherewith the flow of the pressurized fluid flowing through the inflation lumen is not interfered with and the flexibility of the distal part of the catheter is not impaired. A shape is preferable that is a tapered shape, wherewith the outer diameter of the distal part of the catheter shaft is 0.05 mm to 0.15 mm, and preferably 0.01 mm to 0.15 mm, and the outer diameter of the proximal part is larger than the outer diameter of the distal part, such that the diameter becomes larger as the proximal side is approached.

More specific embodiments of the balloon catheters of the second and third embodiments described in the foregoing are now described in detail.

EMBODIMENT 2

The balloon catheter in Embodiment 2 is a balloon catheter having the structure diagrammed in FIG. 5, comprising a polycarbonate adapter member 25, a proximal-side tubular member 22 made of polyimide that communicates with the pressurized fluid induction port 25a, a distal-side tubular member 23 made of a polyamide elastomer that is more flexible that the proximal-side tubular member 22, and a guide wire passing tube 24 that is deployed inside the inflation lumen 26 and passes concentrically through the internal space 5f in the balloon 5. Accordingly, this is a balloon catheter wherein the catheter shaft 21 is configured so that the proximal part thereof is stiffer than the distal part.

The tension generation means 30 described earlier are deployed inside the distal-side tubular member 23 of such a balloon catheter. The outer diameter of the linear member 32 joined to the coiled elastic body 31 is 0.12 mm at the farthest end, and 0.30 mm at the proximal end. The metal coiled elastic body 31 is deployed in the vicinity of the proximal-side tubular member 22 that is the proximal end lumen in the tubular member 23 that is relatively on the distal side in the inflation lumen. Before it was used, the balloon was subjected to a folding heat treatment and the folded condition was memorized to maintain foldability, and then the balloon 5 was sterilized with ethylene oxide gas.

EMBODIMENT 3

The balloon catheter in Embodiment 3 is a balloon catheter having the structure diagrammed in FIG. 8, comprising a polycarbonate adapter member 44, a proximal-side tubular member 42 made of a metal that communicates with the pressurized fluid induction port 44a, a distal-side tubular member 43 made of polyethylene that is more flexible that the proximal-side tubular member 42 made of metal, and a guide wire passing tube 7 that passes concentrically through the internal space 5f in the balloon 5. Accordingly, this is a balloon catheter wherein the catheter shaft 41 is configured such that the proximal part thereof is stiffer than the distal part thereof.

Tension generation means 30 having the same structure as was used in Embodiment 2 are deployed in the interior of the distal-side tubular member 43 of such a balloon catheter. Before it was used, the balloon was subjected to a folding heat treatment and the folded condition was memorized to maintain foldability, and then the balloon was sterilized with ethylene oxide gas.

EMBODIMENT 4

The balloon catheter in Embodiment 4 is a balloon catheter having the structure diagrammed in FIG. 6. The structure thereof is roughly identical to that in Embodiment 2 described above, excepting in that the linear member 32 of the tension generation means 30 is made long in the distal direction and the leading end 32b thereof is bonded to the outer surface of the guide wire passing tube 24 in the interior space 5f of the balloon 5.

EMBODIMENT 5

Figure 9:
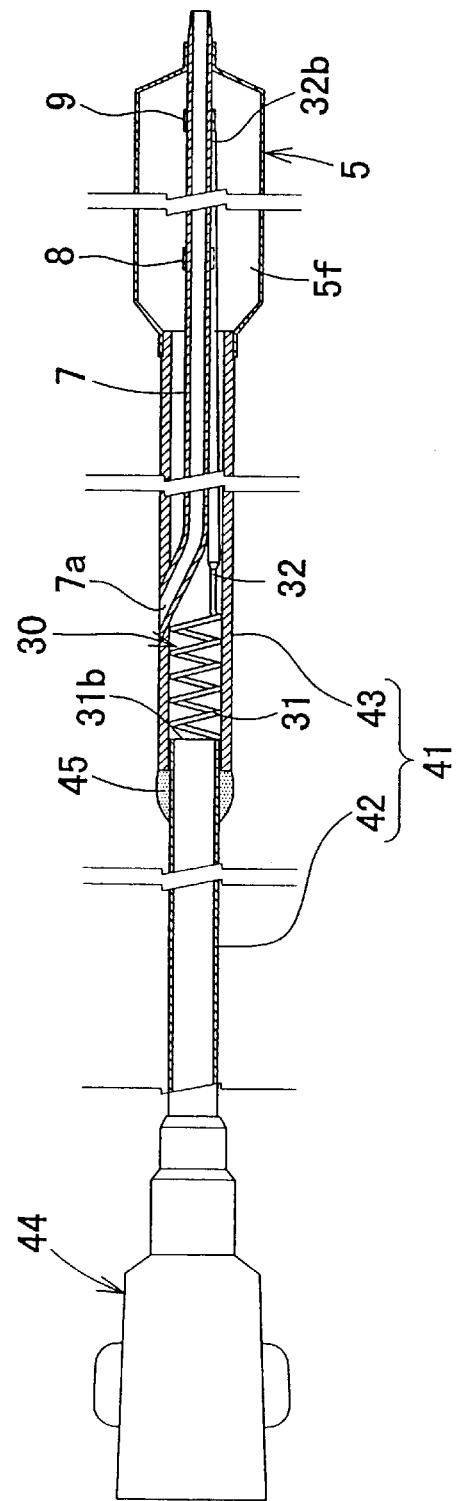
FIG. 9 is a simplified cross-sectional view of a modification of the balloon catheter of the third embodiment.
Figure 10:
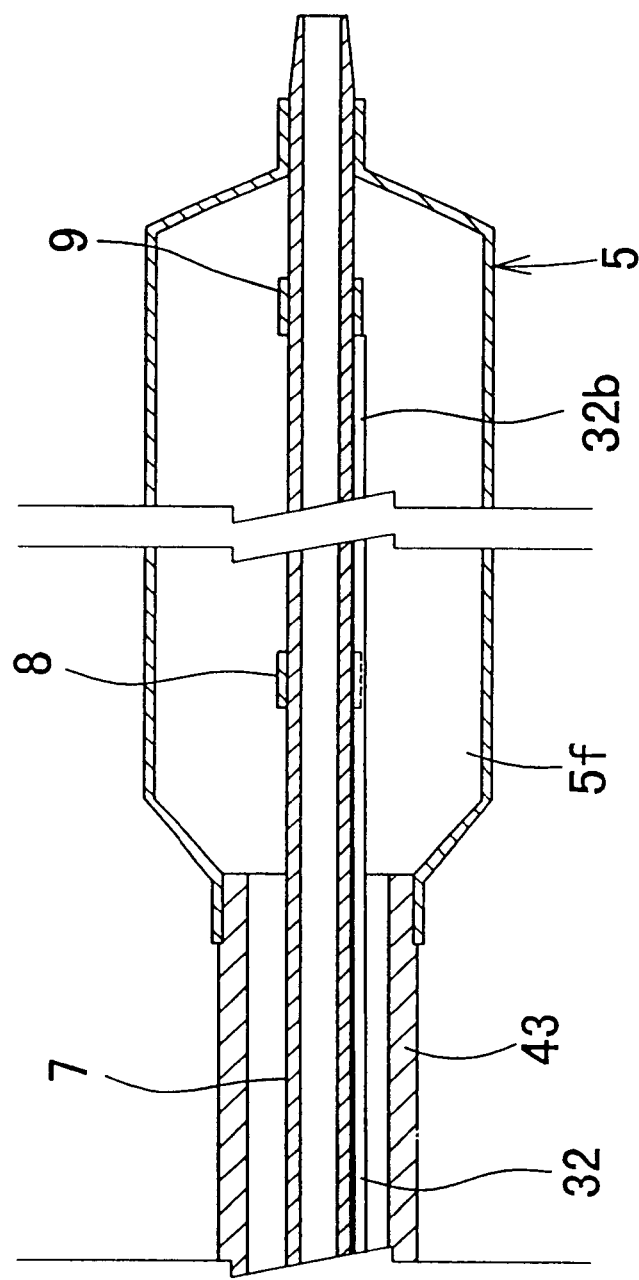
FIG. 10 is an enlarged view of the distal part of the balloon catheter diagrammed in FIG. 9.

The balloon catheter in Embodiment 5 is a balloon catheter having the, structure diagrammed in FIG. 9. The structure thereof is roughly identical to that in Embodiment 3 described above, excepting in that the linear member 32 of the tension generation means 30 is made long in the distal direction and the leading end 32b thereof is bonded to the outer surface of the guide wire passing tube 7 in the interior space 5f of the balloon 5.

EVALUATION OF EMBODIMENTS 2–5

Embodiment 2 and Embodiment 4, as described in the foregoing, were fabricated using a proximal-side tubular member made of a polyimide in the proximal part of the catheter shaft, and using a distal-side tubular member made of a polyamide elastomer in the distal part of the catheter shaft, but there was no particular need for any other reinforcement at the place where the proximal-side tubular member and distal-side tubular member were joined, and it was verified that these were catheters wherein deformations or failures such as kinks or buckling do not readily occur. Also, it was verified that these are catheters that exhibit outstanding controllability because the rigidity varies continuously from the proximal part to the distal part of the catheter.

Furthermore, Embodiment 3 and Embodiment 5 were fabricated using a proximal-side tubular member made of metal in the proximal part of the catheter shaft and using a distal-side tubular member made of polyethylene exhibiting greatly different rigidity than that of the metal tubular member in the distal part of the catheter shaft, but there was no particular need for any other reinforcement at the place where the proximal-side tubular member and distal-side tubular member were joined, and it was verified both that these were catheters wherein deformations or failures such as kinks or buckling do not readily occur, and that these are catheters that exhibit outstanding controllability because the rigidity varies continuously from the proximal part to the distal part of the catheter.

The balloon catheters of the embodiments described in the foregoing were evaluated using the test system diagrammed in FIG. 3, described earlier. Specifically, an internal pressure of 6 atm was introduced into balloon catheters having balloons having a nominal value of 3.0 mm, the balloons were expanded for 1 minute, and then made to contract with the application of a negative pressure. The balloons, in that condition, were advanced into a narrow-diameter tube 16 (inner diameter=2.0 mm) deployed inside a tube 15 having a relatively large inner diameter (3.5 mm), and the loads acting on each of those balloons were measured.

According to the results, with Embodiment 4 and Embodiment 5, when the balloons were made to contract after being expanded, a tension was produced in the balloon in the axial direction, wherefore no wrinkles roughly at right angles to the axial direction were produced, and the balloons were made to contract with folds being produced parallel to the axial direction of the catheters. Hence in 10 out of 10 cases, in both embodiments, the balloon portion could be easily advanced into the narrow-diameter tube 16.

Balloon catheters in comparative examples mounted with the same balloon as in those embodiments, but without the tension generation means, were prepared and evaluated in the same manner with the test system noted above. When the balloons were made to contract after being expanded, the folded condition did not stabilize, a condition was observed wherein wrinkles developed at right angles to the axial direction of the wings, as diagrammed in FIG. 33 (conventional diagram), and it was impossible to advance the balloons into the narrow-diameter tube 16 in 5 cases out of 10.

Figure 12:
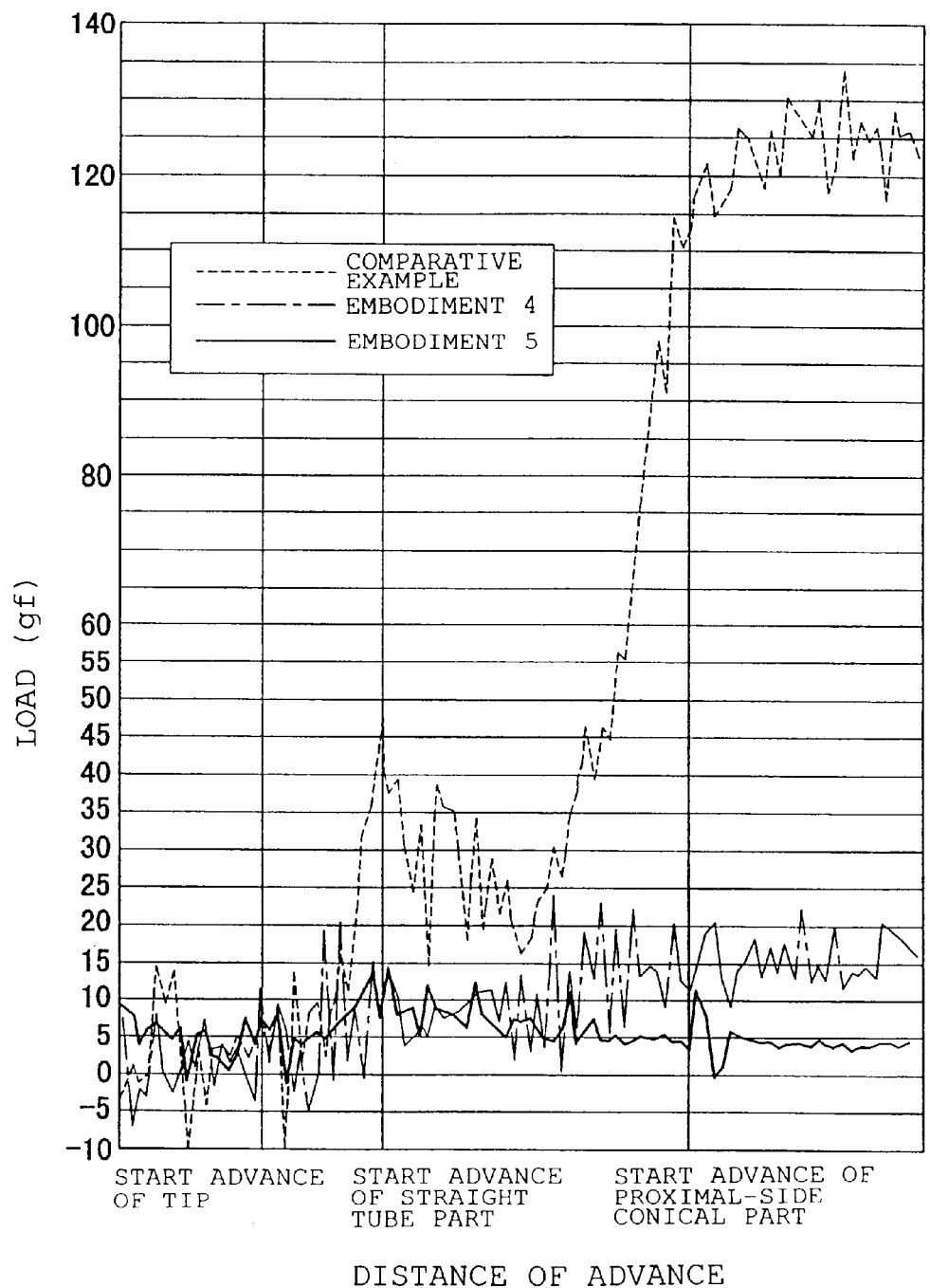
FIG. 12 is a graph representing the results of testing balloon catheters.

In FIG. 12, as in the graph presented in FIG. 4, loads acting on balloon catheters in embodiments and comparative examples are plotted. As plotted in FIG. 12, it is indicated that, even when it is possible to advance the balloon into the narrow-diameter tube 16, with Embodiment 4 and Embodiment 5, the resistance value (generated load) at the point in time when the straight tube part of the balloon is advanced into the narrow-diameter tube is small, whereas, with the comparative examples, a larger resistance is produced than in Embodiment 4 or Embodiment 5 from the point in time when the straight tube part of the balloon is advanced into the narrow-diameter tube.

Thus, with the balloon catheters of Embodiment 4 and Embodiment 5, because tension develops in the balloon in the axial direction, no wrinkles develop at right angles to the axial direction of the catheter, and the balloon is folded up, and made to contract with folds produced parallel to the axial direction of the catheter. Therefore these are balloon catheters that exhibit outstanding redeployability to lesion sites and ease of balloon extraction from internal passages after treatment, and have extremely favorable characteristics as balloon catheters.

A method of applying a hydrophilic coating to the outer surface of the distal part of a balloon catheter to enhance the low resistance characteristic of balloon catheters like those described in the foregoing is next described. The degree of stiffness in the outside tubular member configuring the catheter shaft is such that the bending rigidity of the tubular member, for example, can be calculated with the product of the cross-sectional secondary moment and elastic modulus of the intermediate member, and, further, such that it is possible to make measurements, material-dynamically, in tests, from the sag amount and load amount when the tubular member is caused to sag in a flexible curve. In general, it is represented that stiffness is greater the higher the bending rigidity. Ordinarily, however, portions that clearly feel stiff can be judged to be "hard" compared to other portions. The diameter of the outside tubular member can be measured with a laser outer diameter measurement instrument or the like, moreover, but, in view of the circumstances wherein it is used, a balloon catheter should be evaluated by its outer diameter when it has a circular shape, and by the outer diameter at the longer axis when it has an elliptical shape, and is represented as having a larger diameter the larger that outer diameter is.

In general, over-the-wire type balloon catheters are configured such that, in terms of materials and shape, the near portion of the outside tubular member is stiff, and the far portion is more flexible than the near portion, but there are cases where, particularly as respecting the far portion, the stiffness thereof varies, either in stages or continuously. In such cases as that, the portion wherein the shape and rigidity are comparatively unchanged through a range from the vicinity of the adapter member out to a distance of 1 meter or so on the distal-side should be recognized as the near portion, and the range from there on toward the balloon side recognized as the far portion. There are also cases where no distinction can be made between the outside tubular member and the inside tubular member in a balloon catheter. It has already been made clear, for example, that a shape can be effected wherein the tubes forming the inflation lumen and the guide wire lumen are deployed in parallel or integrated. Even in such cases as that, the fact that being configured such that the range within 300 mm or so from the farthest end of the catheter is flexible, and the range from there on the proximal side is stiff, is effective, is the same as in a common over-the-wire or rapid exchange type balloon catheter. The present invention indicates that applying a hydrophilic coating within a range extending from the foremost end of the balloon catheter for a distance of more than 300 mm is effective irrespective of the balloon catheter type or shape.

It should be noted that there is no limitation on the type of or method for applying the hydrophilic coating used in the present invention. It is possible to use a water soluble or hydrophilic polymer material such, for example, as a polyethylene glycol, polyethylene oxide, polyvinyl alcohol, polyvinyl pyrrolidone, polyacrylamide, collagen, or chitosan, or copolymer or derivative thereof, as may be suitable. For the method of fixing these polymer materials to the catheter, moreover, a method of inducting a reactive polymer into the catheter base material, or graft polymerization using a plasma or radiation, or graft polymerization using a photo-reactive substance or the like, can be used. Furthermore, as to where the hydrophilic coating is applied in the present invention, there is no limitation on position, deployment, continuity, or thickness, so long as there is no specific limitation cited in the claims, but it is preferable that application be made to those sites in the catheter shaft configuring the balloon catheter that are relatively hard, in particular.

Embodiments wherein the hydrophilic coating relating to the present invention is applied are now described more specifically and in greater detail.

EMBODIMENT 6

Figure 27:
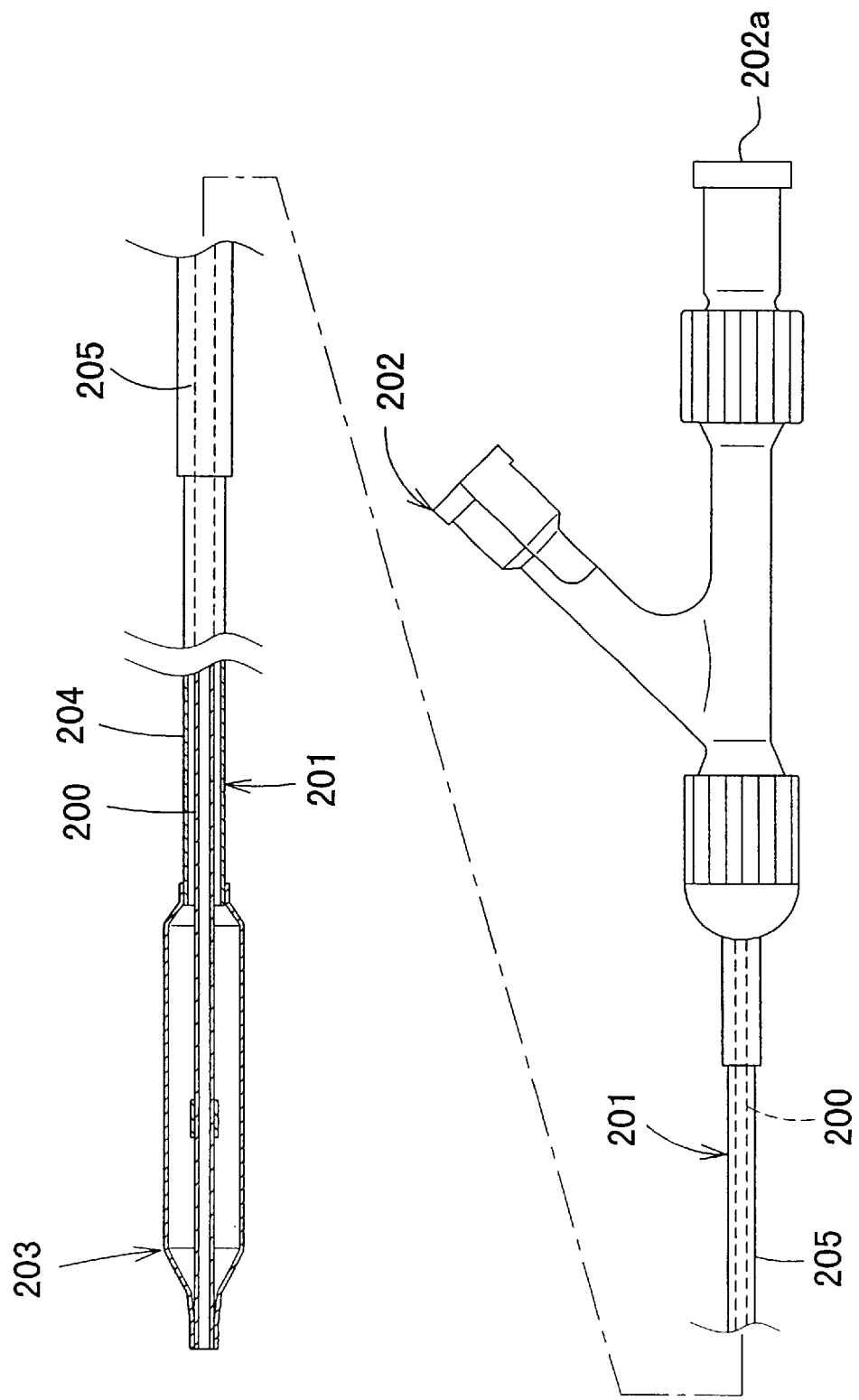
FIG. 27 is a cross-sectional view of the main parts of a conventional over-the-wire type balloon catheter.

An over-the-wire balloon catheter having the same structure as the catheter diagrammed in FIG. 27 was prepared. In configuring this balloon catheter, a distal-side tubular member made of a polyamide elastomer and having an outer diameter of 0.90 mm, an inner diameter of 0.72 mm, and a bending rigidity of 475 gf·mm$^2$ was used for the catheter distal part, and a proximal-side tubular member made of a polyimide and having an outer diameter of 1.07 mm, an inner diameter of 0.87 mm, and a bending rigidity of 7241 gf·mm$^2$ was used for the catheter proximal part, making it a balloon catheter wherein the proximal part of the catheter is substantially stiffer than the distal part thereof. To the base end of the catheter shaft configured using such tubular members, an adapter member is joined, to the distal end the balloon is joined, and a guide wire passing tube is deployed concentrically inside the catheter shaft, extending from the base end to the balloon distal end. The flexible distal part (the part made of the polyamide elastomer) of such a catheter shaft exists within a range extending 270 mm from the farthest end of the balloon catheter toward the proximal side.

The range of 300 mm from the farthest end of the balloon catheter toward the proximal side was immersed in a 22.5 v/v% isopropyl alcohol solution containing approximately 1% each of a polyvinyl pyrrolidone copolymer wherein benzoylbenzoic acid was introduced and a polyacrylamide copolymer wherein benzoylbenzoic acid was introduced. Thus a portion of the proximal part (the polyimide portion) that is stiffer than the distal part was immersed in the coating solution. After that, the range so immersed was irradiated with ultraviolet light to fix the coating. Then, after folding up the balloon and covering it with a sheath, sterilization was performed using ethylene oxide gas. Thus the balloon catheter of Embodiment 6 was fabricated.

EMBODIMENT 7

An over-the-wire balloon catheter like that in Embodiment 6 was prepared. Then the range extending 1000 mm from the farthest end of the balloon catheter toward the proximal side was immersed in a 22.5 v/v% isopropyl alcohol solution containing approximately 1% each of a polyvinyl pyrrolidone copolymer wherein benzoylbenzoic acid was introduced and a polyacrylamide copolymer wherein benzoylbenzoic acid was introduced. After that, that immersed range was irradiated with ultraviolet light to fix the coating, and, after folding up the balloon and covering it with a sheath, sterilization was performed using ethylene oxide gas. Thus the balloon catheter of Embodiment 7 was fabricated.

EMBODIMENT 8

Figure 28:
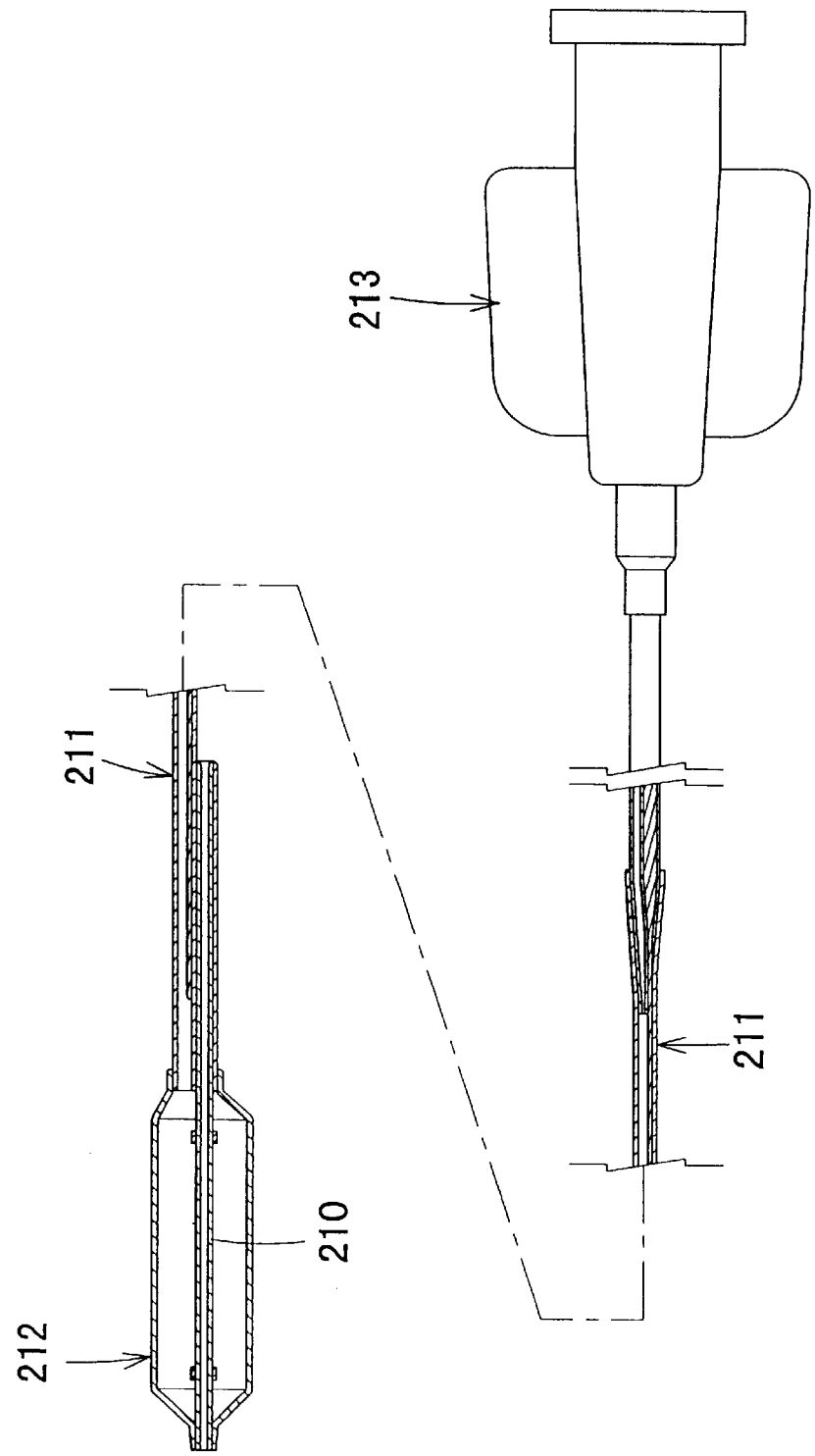
FIG. 28 is a cross-sectional view of the main parts of a conventional rapid exchange type balloon catheter.
Figure 31A:
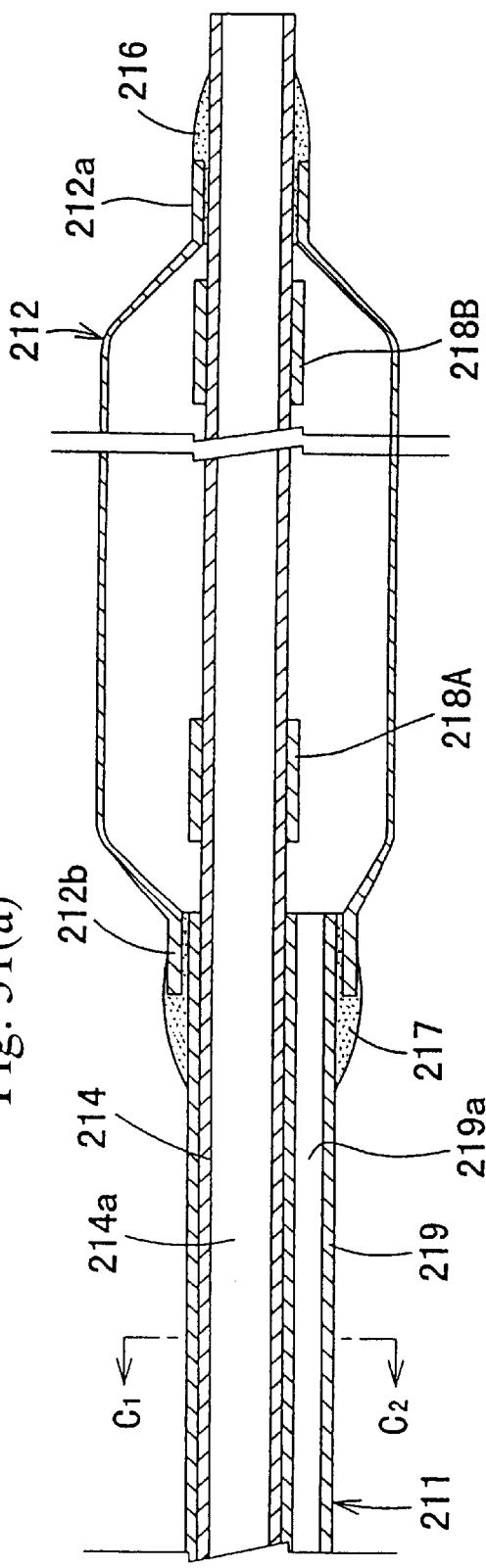
FIG. 31($a$) is a simplified cross-sectional view of the leading end of a common balloon catheter, while FIG. 31($b$) is the $C_1$–$C_2$ cross-section thereof.
Figure 31B:
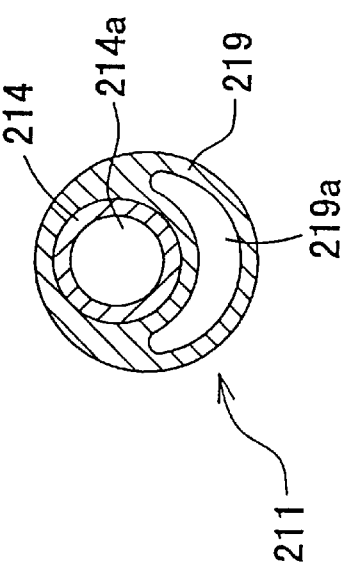
Figure 32A:
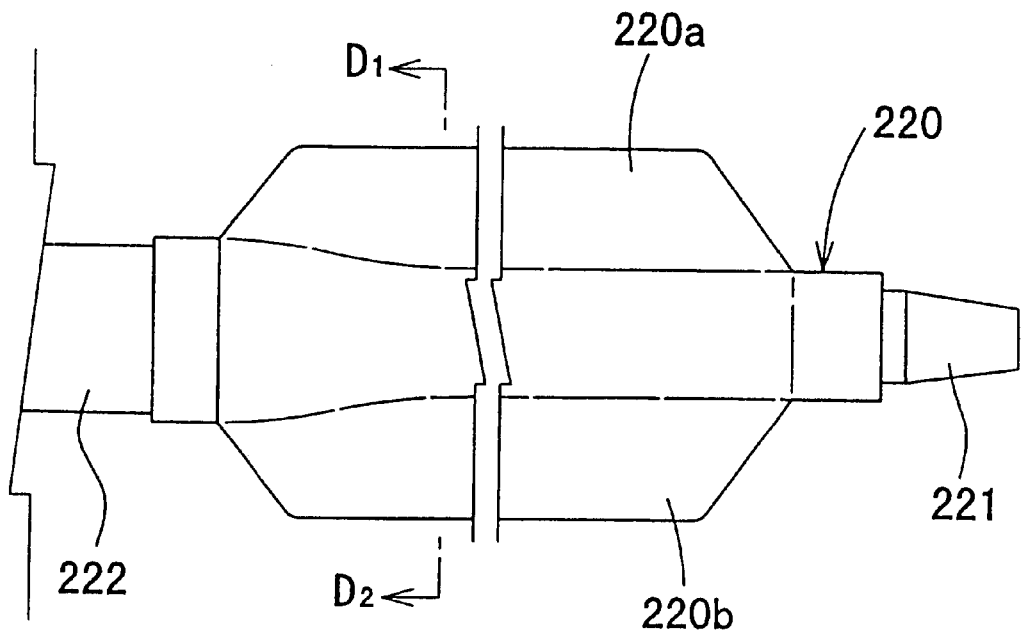
FIG. 32 is simplified diagram of a balloon wherein wings are formed, with (a) being a side view of the balloon and (b) being the $D_1$–$D_2$ cross-section thereof.
Figure 32B:
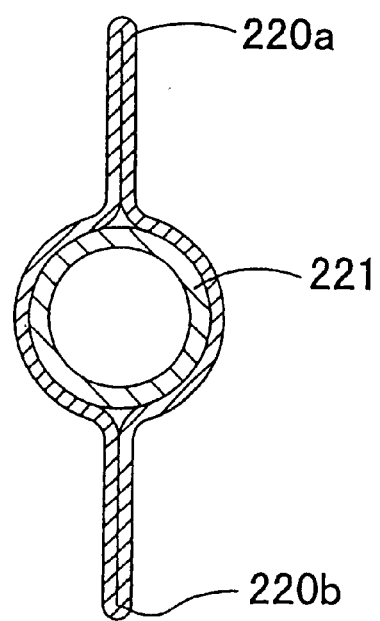

A rapid exchange balloon catheter having the same structure as the catheter diagrammed in FIG. 28 was prepared. In this balloon catheter, the guide wire passing tube is deployed only in the catheter distal part, and a back end opening (guide wire insertion opening) for the guide wire passing tube is formed at a position 250 mm on the proximal side from the farthest end of the balloon catheter.

Thereupon, after protecting the passage for passing the guide wire (the guide wire lumen), a range extending 300 mm from the farthest end of this balloon catheter toward the proximal side was immersed in a 22.5 v/v% isopropyl alcohol solution containing approximately 1% each of a polyvinyl pyrrolidone copolymer wherein benzoylbenzoic acid was introduced and a polyacrylamide copolymer wherein benzoylbenzoic acid was introduced. After that, that immersed range was irradiated with ultraviolet light to fix the coating, and, after folding up the balloon and covering it with a sheath, sterilization was performed using ethylene oxide gas. Thus the balloon catheter of Embodiment 8 was fabricated.

EMBODIMENT 9

A rapid exchange balloon catheter like that in Embodiment 8 was prepared. Then a range extending 1000 mm from the farthest end of the balloon catheter toward the proximal side was immersed in a 22.5 v/v% isopropyl alcohol solution containing approximately 1% each of a polyvinyl pyrrolidone copolymer wherein benzoylbenzoic acid was introduced and a polyacrylamide copolymer wherein benzoylbenzoic acid was introduced. After that, that immersed range was irradiated with ultraviolet light to fix the coating, and, after folding up the balloon and covering it with a sheath, sterilization was performed using ethylene oxide gas. Thus the balloon catheter of Embodiment 9 was fabricated.

COMPARATIVE EXAMPLE 1

An over-the-wire balloon catheter like that in Embodiment 6 was prepared. Then a range extending 250 mm from the farthest end of the balloon catheter toward the proximal side was immersed in a 22.5 v/v% isopropyl alcohol solution containing approximately 1% each of a polyvinyl pyrrolidone copolymer wherein benzoylbenzoic acid was introduced and a polyacrylamide copolymer wherein benzoylbenzoic acid was introduced. Accordingly, unlike the cases of the embodiments described in the foregoing, there was no immersing of the solution described above in the catheter shaft proximal part (polyimide part). After that, that immersed range was irradiated with ultraviolet light to fix the coating, and, after folding up the balloon and covering it with a sheath, sterilization was performed using ethylene oxide gas. Thus the balloon catheter of Comparative Example 1 was fabricated.

COMPARATIVE EXAMPLE 2

A rapid exchange balloon catheter like that in Embodiment 8 was prepared. Then, after protecting the passage for passigng the guide ware (the guide wire lumen), a range extending 230 mm from the farthest end of the catheter shaft was immersed in a 22.5 v/v% isopropyl alcohol solution containing approximately 1% each of a polyvinyl pyrrolidone copolymer wherein benzoylbenzoic acid was introduced and a polyacrylamide copolymer wherein benzoylbenzoic acid was introduced. After that, that immersed range was irradiated with ultraviolet light to fix the coating, and, after folding up the balloon and covering it with a sheath, sterilization was performed using ethylene oxide gas. Thus the balloon catheter of Comparative Example 2 was fabricated.

TEST SYSTEM; EVALUATIONS OF EMBODIMENTS 6–9

Comparative Examples 1 and 2

Figure 13:
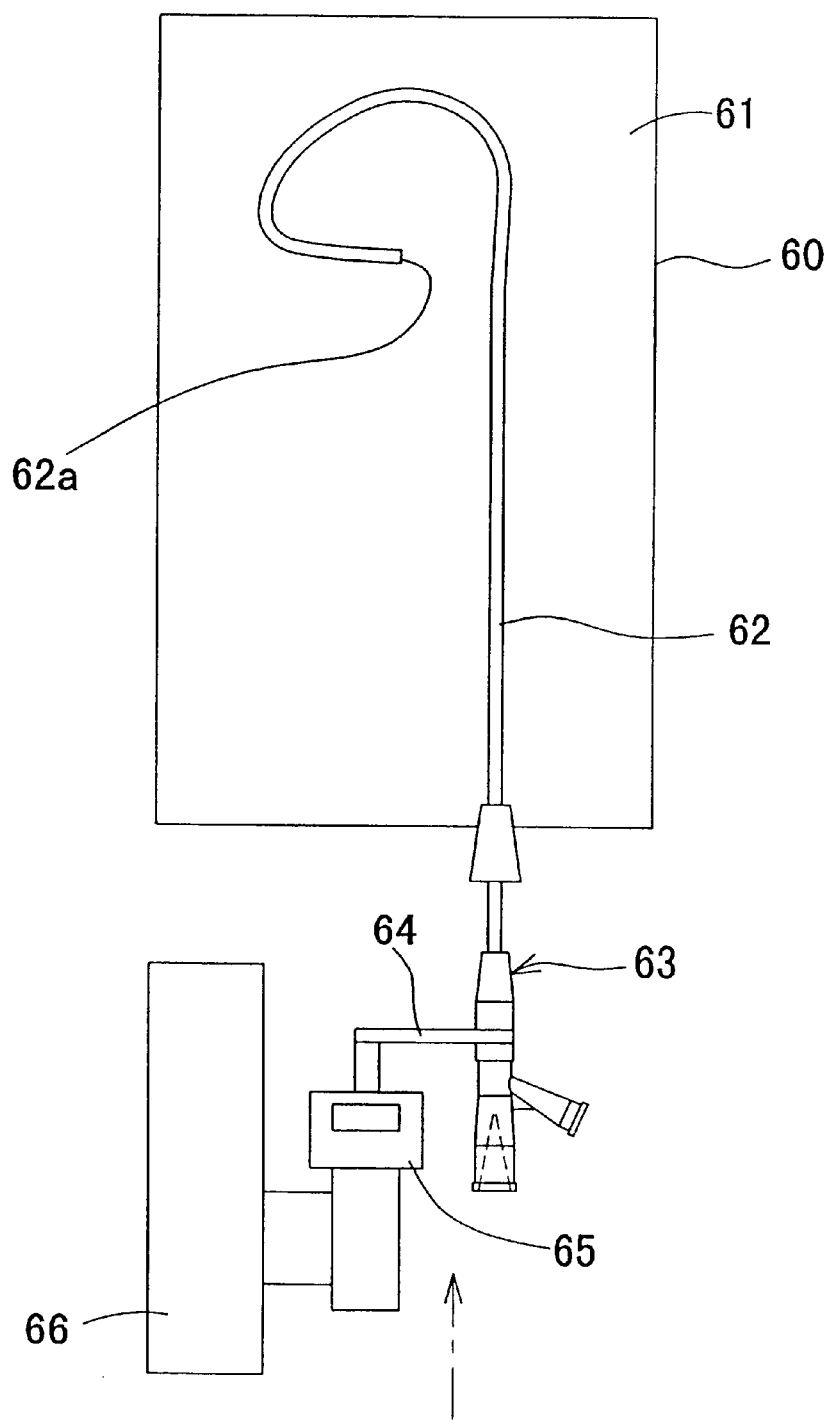
FIG. 13 is a simplified view of a test system for testing samples of balloon catheters relating to the present invention.

The test system diagrammed in FIG. 13 was prepared in order to evaluate the balloon catheters of Embodiments 6 to 9 and Comparative Examples 1 and 2. Specifically, a guiding catheter 62 was deployed in a vessel 60 filled with physiological saline solution 61 at 37° C. The adapter member of a balloon catheter 63 (the subject of evaluation) was fixed in a holding jig 64. This holding jig 64 is connected to a force gauge 65. The force gauge 65 is supported by a manipulator 66. The manipulator 66 was moved, advancing the balloon catheter, and the loads acting on the adapter member were measured while pushing the balloon catheter being evaluated ahead at 20 mm/sec inside the guiding catheter 62 until the leading end of the balloon catheter reached a distance of 200 mm from the farthest end of the balloon catheter.

The measurements were made using two types of guiding catheter 62, namely a commercially available size 8F-JL4 product having inner surfaces made of Teflon (hereinafter called guiding catheter I), and a commercially available size 8F-JL4 product having inner surfaces made of polypropylene (hereinafter called guiding catheter II).

The measurement results are given in Table 1 below.

TABLE 1

|  | Guiding Catheter I Maximum resistance value when used (gf) | Guiding Catheter II Maximum resistance value when used (gf) |
| --- | --- | --- |
| Embodiment 6 | 25 | 29 |
| Embodiment 7 | 25 | 27 |
| Embodiment 8 | 22 | 26 |
| Embodiment 9 | 21 | 23 |
| Comparative Example 1 | 50 | 120 |
| Comparative Example 2 | 30 | 76 |

Comparing the over-the-wire type Embodiments 6 and 7 against Comparative Example 1 in Table 1, in cases of both guiding catheter I and guiding catheter II, the values for Embodiments 6 and 7 were smaller than the resistance values for Comparative Example 1. Thus a pronounced resistance diminishing effect was observed in both of these embodiments.

Comparing the rapid exchange type Embodiments 8 and 9 against Comparative Example 2, in cases of both guiding catheter I and guiding catheter II, the values for Embodiments 8 and 9 were smaller than the resistance values for Comparative Example 2. Thus a resistance diminishing effect was observed in both of these embodiments, and a particularly pronounced effect was observed for the guiding catheter II having inner surfaces made of polypropylene.

Also, using the guiding catheter I having inner surfaces made of Teflon in the test system described earlier, a condition was created wherein Embodiment 7, Embodiment 9, Comparative Example 1, and Comparative Example 2 were deployed two at a time, simultaneously, in that guiding catheter I so as to extend out 100 mm from the leading end 62a of the guiding catheter 62. One of the balloon catheters was thereupon moved reciprocally with an amplitude of 20 mm and period of 2 seconds, and the loads acting on the adapter member of the balloon catheter being reciprocally moved were measured.

The measurement results are given in Table 2 below.

TABLE 2

|  | Maximum sliding friction value (gf) when deploying two balloon catheters simultaneously using guiding catheter I |
| --- | --- |
| Embodiment 6 | 37 |
| Embodiment 7 | 17 |
| Embodiment 8 | 32 |
| Embodiment 9 | 15 |
| Comparative Example 1 | 46 |
| Comparative Example 2 | 39 |

When the over-the-wire Embodiments 6 and 7 and Comparative Example 1 are compared, looking at the results given in Table 2, it is seen that the values for Embodiments 6 and 7 are respectively smaller than the resistance values for Comparative Example 1, and a particularly large resistance diminishing effect is observed in the case of Embodiment 7 where the range of the hydrophilic coating is a comparatively broad range.

When the rapid exchange type Embodiments 8 and 9 are compared against Comparative Example 2, moreover, the values for Embodiments 8 and 9 are respectively smaller than the resistance value for Comparative Example 2, and a particularly large resistance diminishing effect is observed in the case of Embodiment 7 where the range of the hydrophilic coating is a comparatively broad range.

Thus it was verified that balloon catheters relating to the present invention wherein the hydrophilic coating range is established all the way to the proximal part of the balloon catheter exhibit a friction reducing effect with the guiding catheter and a balloon catheter that is inserted simultaneously therewith, and that good controllability can be obtained with those balloon catheters.

Figure 14:
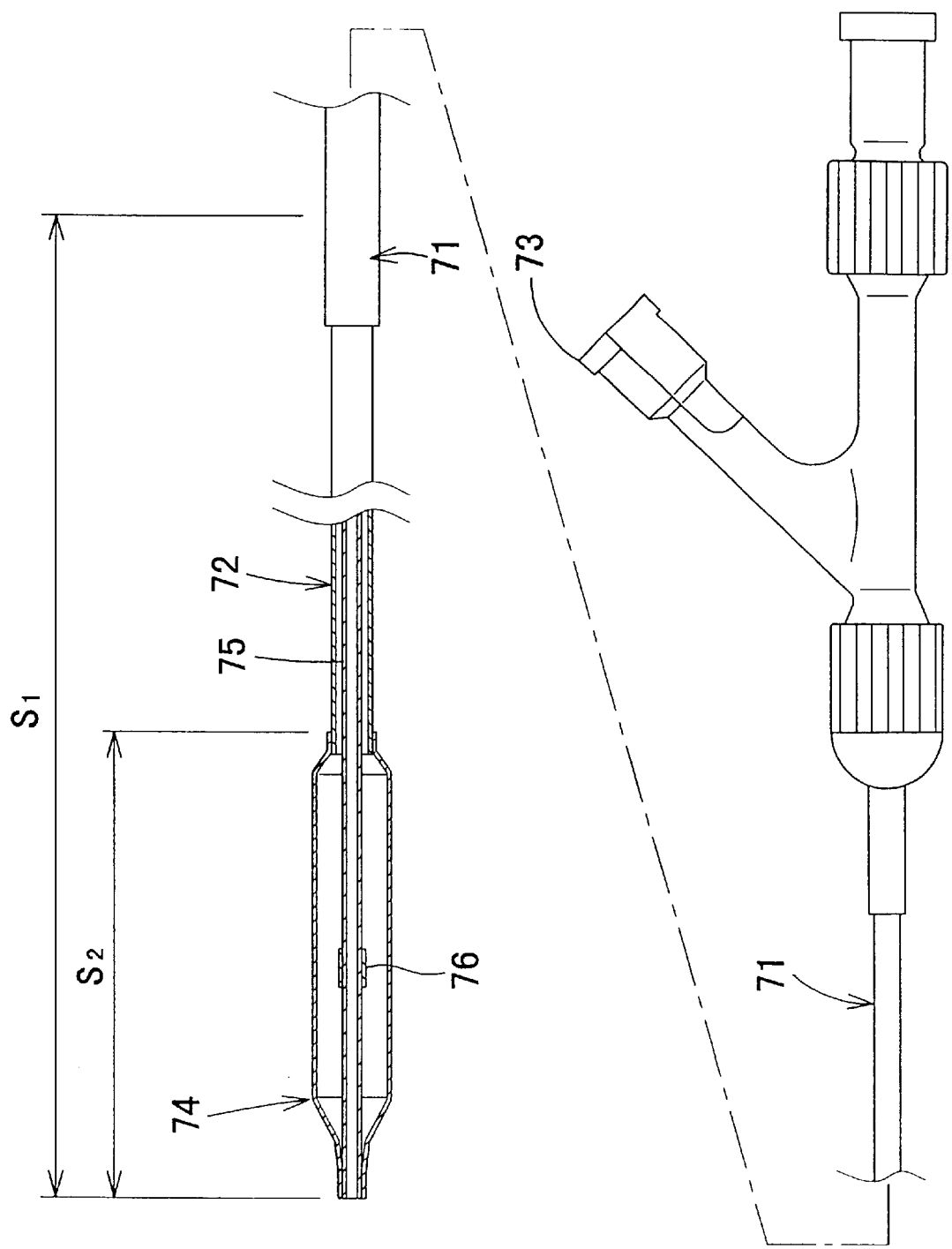
FIG. 14 is a simplified diagram showing the range wherein a hydrophilic coating is applied to the outer surface of a balloon catheter.

Next, as described earlier, when a hydrophilic coating is applied to the distal part of a catheter and a hydrophilic coating is also applied to the balloon, there has been a problem in that sticking occurs in the balloon when folded up, and the expansion performance thereof declines sharply. A hydrophilic coating method which overcomes this problem is now described. This is described below, taking the over-the-wire balloon catheter diagrammed in FIG. 14 as an example. In the present invention, however, there is no limitation to an over-the-wire type, and application is also possible with rapid exchange types of the same vasodilating catheters. In FIG. 14, the symbol 71 denotes a proximal-side tubular member, 72 a distal-side tubular member, 73 an adapter member, 74 a balloon, 75 a guide wire passing tube, and 76 a radiopaque marker. To facilitate understanding, moreover, the catheter distal part is diagrammed as slightly enlarged compared to the proximal part.

First, in the distal part of the balloon catheter, a hydrophilic polymer solution is applied to the outer surfaces over a range $S_1$ containing the balloon 74, distal-side tubular member 72, and proximal-side tubular member 71. Next, the outer surfaces of a range $S_2$ containing the balloon 74 and the vicinity thereof are washed by the application of a hydrophilic polymer solution of weak concentration, the concentration of the hydrophilic polymer solution on the outer surfaces of the range $S_1$ is diluted, and then the adhering hydrophilic polymer is subjected to a fixing treatment by applying a heat treatment or UV radiation over the range through which the hydrophilic polymer solution was applied. Thus only a hydrophilic coating of weak concentration is applied to the balloon 74 and vicinity thereof, wherefore sticking can be prevented from occurring in the balloon when folded up.

Another coating method may be employed wherewith, after applying the hydrophilic polymer solution to the outer surfaces in the range $S_1$, the outer surfaces of the range $S_2$ are washed with a solvent that dissolves the hydrophilic polymer solution, and then the hydrophilic polymer adhering to the surfaces of the balloon catheter is subjected to a fixing treatment.

By hydrophilic coating here is meant a coating that exhibits lubricating properties in an environment wherein it is immersed in water, physiological saline, body fluids, or blood, etc., that is, when wetted. There is no particular limitation on the type thereof or method of application. It is possible to use a water soluble or hydrophilic polymer material such, for example, as a polyethylene glycol, polyethylene oxide, polyvinyl alcohol, polyvinyl pyrrolidone, polyacrylamide, collagen, or chitosan, or copolymer or derivative thereof, as may be suitable. The solvent used is one capable of dissolving the water soluble or hydrophilic polymer material, and it is preferable that it be a solvent that does not react with the water soluble or hydrophilic polymer materials noted above, and that contains no reactive group. Suitable solvents include water, low-order alcohols, dichloroethylene, dichloroethane, chloroform, acetohitrile, methylene chloride, and acetone, as well as mixtures thereof. For the method of fixing these polymer materials to the catheter, moreover, a method of inducting a reactive polymer into the catheter base material, or graft polymerization using a plasma or radiation, or graft polymerization using a photo-reactive substance or the like, can be used.

By the expression, balloon or the balloon and vicinity thereof, that is used to indicate the range for the hydrophilic coating of the present invention is meant either the balloon itself, or a range extended adjacently from the balloon, within a range of from approximately 5 mm to 20 mm or so from the balloon on the proximal side thereof, as shown by the range $S_2$ in FIG. 14.

The thickness of the hydrophilic coating layer in the present invention can be observed with a scanning electron microscope, or measured by using a scanning electron microscope and x-ray analysis apparatus together. The thickness of a suitable hydrophilic coating layer is 2 $\mu$m or greater, but preferably 2 to 10 $\mu$m, at the catheter shaft of the distal part of the catheter. The thickness at the balloon or at the balloon and vicinity thereof should be less than 2 $\mu$m, and preferably 0 to 1 $\mu$m. Accordingly, in the distal part of the balloon catheter, it is better that the thickness of the hydrophilic coating layer on the balloon or on the balloon and vicinity thereof be less than the thickness of the hydrophilic coating layer on the catheter shaft. As to a specific fabrication method, however, a method is preferred wherewith, after treating the distal part of the catheter containing the balloon with a hydrophilic coating solution of comparatively high concentration, the hydrophilic coating of comparatively high concentration applied to the balloon is removed using a comparatively dilute hydrophilic coating solution or a solution that acts to remove a hydrophilic coating.

The friction resistance when wet in the present invention can be measured by a variety of methods. A preferred procedure, however, is one wherewith a probe subjected to a certain load in a direction perpendicular to the tube or balloon portion that has been wetted with water is moved in a direction perpendicular to the axial direction of the tube or balloon, and the friction resistance is expressed as the resistance value detected in that direction. In that case, a measurement probe shaped in a variety of ways suitable to the measurement can be suitably used, but a tubular probe is preferable that can easily be deployed so as to be perpendicular to the catheter that is the subject of the measurements because therewith it is possible to compare friction resistances with practically no error relative to the outer diameter of the balloon and the tubular member or members configuring the catheter.

When such a tubular probe is used, moreover, comparatively similar measurement results are obtained when the balloon is folded up and when it is expanded, but the folded condition is preferable because then the probe is closer to the diameter of the tube in the direction of the vicinity of the balloon.

As to where the measurements are taken, sites are preferable whereat a horizontal condition can be maintained relative to the catheter axial direction over the entire measurement range. When the locations being measured are at the balloon or vicinity thereof, sites in the straight tube part of the balloon are preferable. When the tubular member in the catheter distal part is made the measurement location, locations are preferable that are sufficiently removed from the balloon and vicinity thereof, where there is no tube connection or other step, such, for example, as sites that are more to the proximal side from the balloon and connection thereof by 5 cm to 10 cm or so.

Embodiments of balloon catheters wherein the hydrophilic coating described in the foregoing have been applied are now described more specifically.

EMBODIMENT 10

An over-the-wire balloon catheter such as that diagrammed in FIG. 14 was prepared. As to the materials used here in each part, a polyester copolymer was used in the balloon 74, a polyamide elastomer in the distal-side tubular member 72, a polyimide in the proximal-side tubular member 71, and polyethylene in the guide wire passing tube 75. The outer surface of the range $S_1$ in such a balloon catheter was immersed in methylethyl ketone containing 1% of γ-aminopropyl triethoxy silane, and then heated and an amino group introduced in the surface. Next, the outer surface of the range $S_1$ thereof was immersed for 10 seconds in a mixed solution of chloroform and acetonitrile containing 0.8% of a copolymer of acrylic acid N-hydroxy succinic acid imide ester and N-vinyl pyrrolidone, and, immediately thereafter, the outer surface of the range $S_2$ of the balloon catheter was immersed for 15 seconds in a mixed solution of chloroform and acetonitrile containing 0.2% of a copolymer of acrylic acid N-hydroxy succinic acid imide ester and N-vinyl pyrrolidone. The entire catheter was then blow-dried and subjected to a heat treatment to fix the coating. After folding up the balloon portion and covering it with a sheath, sterilization was performed using ethylene oxide gas. Thus the balloon catheter of Embodiment 10 was fabricated.

EMBODIMENT 11

An over-the-wire balloon catheter like that of Embodiment 10 was prepared. The outer surface of the range $S_1$ in this balloon catheter was immersed in methylethyl ketone containing 1% γ-aminopropyl triethoxy silane, and then heated and an amino group introduced in the surface. Next, the outer surface of the range $S_1$ thereof was immersed for 10 seconds in a mixed solution of chloroform and acetonitrile containing 0.8% of a copolymer of acrylic acid N-hydroxy succinic acid imide ester and N-vinyl pyrrolidone, and, immediately thereafter, the B portion of the balloon catheter was immersed for 20 seconds in a mixed solution of chloroform and acetonitrile, the copolymer of acrylic acid N-hydroxy succinic acid imide ester and N-vinyl pyrrolidone was removed, the entire catheter was blow-dried, a heat treatment was done to fix the coating, the balloon portion was folded up and covered with a sheath, and sterilization was performed using ethylene oxide gas. Thus the balloon catheter of Embodiment 11 was fabricated.

EMBODIMENT 3

An over-the-wire balloon catheter like that in Embodiment 10 was prepared. The outer surface of the range $S_1$ in this balloon catheter was immersed in methylethyl ketone containing 1% γ-aminopropyl triethoxy silane, and then heated and an amino group introduced in the surface. Next, the outer surface of the range $S_1$ thereof was immersed for 10 seconds in a mixed solution of chloroform and acetonitrile containing 0.2% of a copolymer of acrylic acid N-hydroxy succinic acid imide ester and N-vinyl pyrrolidone, then the entire catheter was blow-dried, a heat treatment was done to fix the coating, the balloon portion was folded up and covered with a sheath, and sterilization was performed using ethylene oxide gas. Thus the balloon catheter of Comparative Example 3 was fabricated.

COMPARATIVE EXAMPLE 4

An over-the-wire balloon catheter like that in Embodiment 10 was prepared. The outer surface of the range $S_1$ in this balloon catheter was immersed in methylethyl ketone containing 1% γ-aminopropyl triethoxy silane, and then heated and an amino group introduced in the surface. Next, the outer surface of the range $S_1$ thereof was immersed for 10 seconds in a mixed solution of chloroform and acetonitrile containing 0.8% of a copolymer of acrylic acid N-hydroxy succinic acid imide ester and N-vinyl pyrrolidone, then the entire catheter was blow-dried, a heat treatment was done to fix the coating, the balloon portion was folded up and covered with a sheath, and sterilization was performed using ethylene oxide gas. Thus the balloon catheter of Comparative Example 4 was fabricated.

EVALUATION OF EMBODIMENT 10 AND 11 AND COMPARATIVE EXAMPLES 3 AND 4

Evaluations were made on Embodiments 10 and 11 and Comparative Examples 3 and 4, based on measured results obtained by the methods described in (1) to (4) below.
(1) Test Method 1:
    The balloon of the balloon catheter being evaluated was pressurized, holding the pressure at each additional 0.1 atmosphere for 1 second, and the balloon expansion pressure was measured.
(2) Test Method 2:
    A portion of the distal-side tubular member in the balloon catheter distal part was cut away, the cross-section there examined with a scanning electron microscope and x-ray analyzer, and the thickness of the hydrophilic coating layer (hereinafter called HC layer) in each portion was measured.

Figure 15:
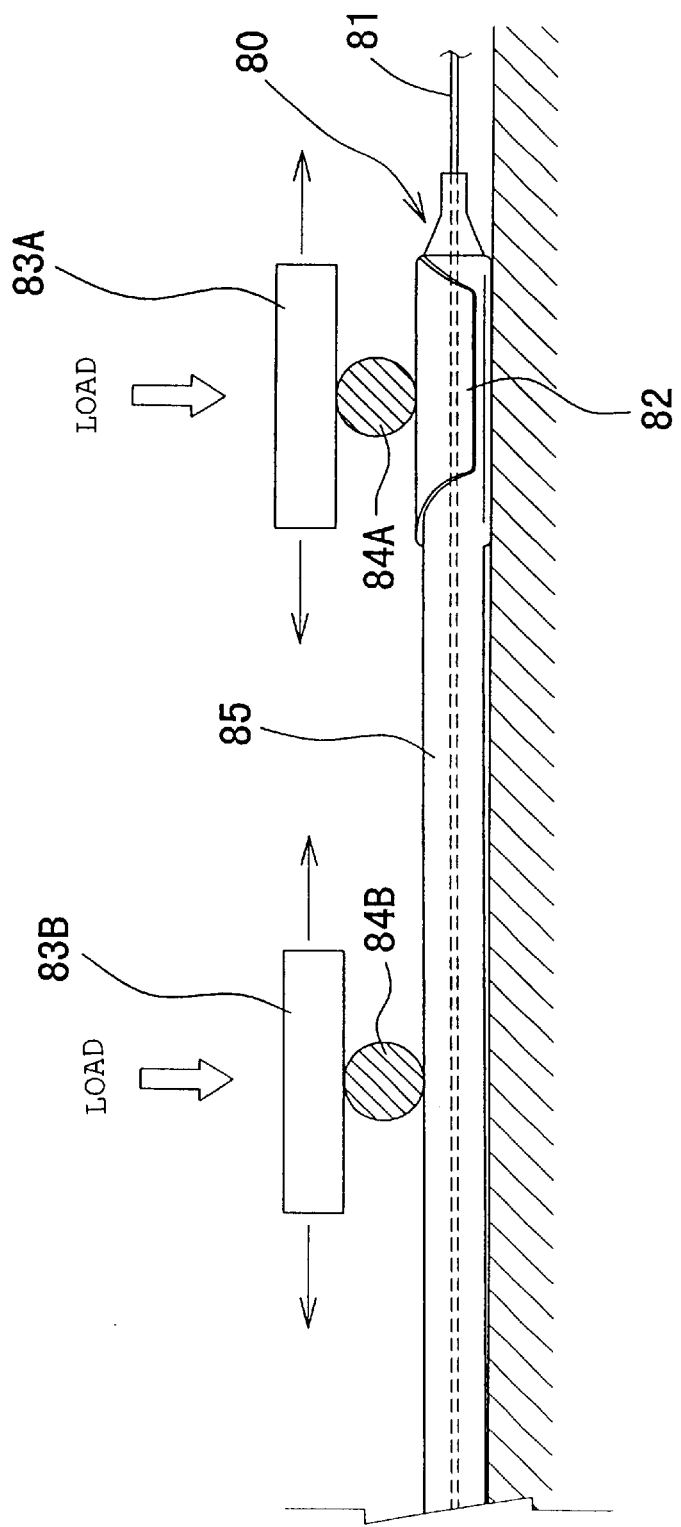
FIG. 15 is a simplified side view of a test system for measuring the friction resistance of the outer surface of a balloon catheter.

(3) Test Method 3:

The test system diagrammed in FIG. 15 was prepared. Specifically, a core material 81 was inserted in the guide wire lumen of a balloon catheter 80 placed on a platform for evaluation, and then the outer circumferential surface of a tubular measurement probe 84A made of vinyl chloride and connected to an ASTM flat pressure piece 83A was brought into contact with the outer surface of the balloon 82 that was made to contract under reduced pressure, folded up, and wetted, and the outer circumferential surface of a tubular probe 84B made of vinyl chloride and connected to an ASTM flat pressure piece 83B was brought into contact with the outer surface of the distal-side tubular member 85 in the catheter distal part, also in a wetted condition. The tubular probes 84A and 84B were moved forward and backward in the axial direction, and the friction resistance forces on those surfaces were measured. For the measurement instrument, the friction tester "HEIDN14DR" made by Shinto Scientific Co., Ltd. (with a measurement probe speed of 300 mm/min, load of 100 g, and stroke of 15 mm) was used.

Figure 16:
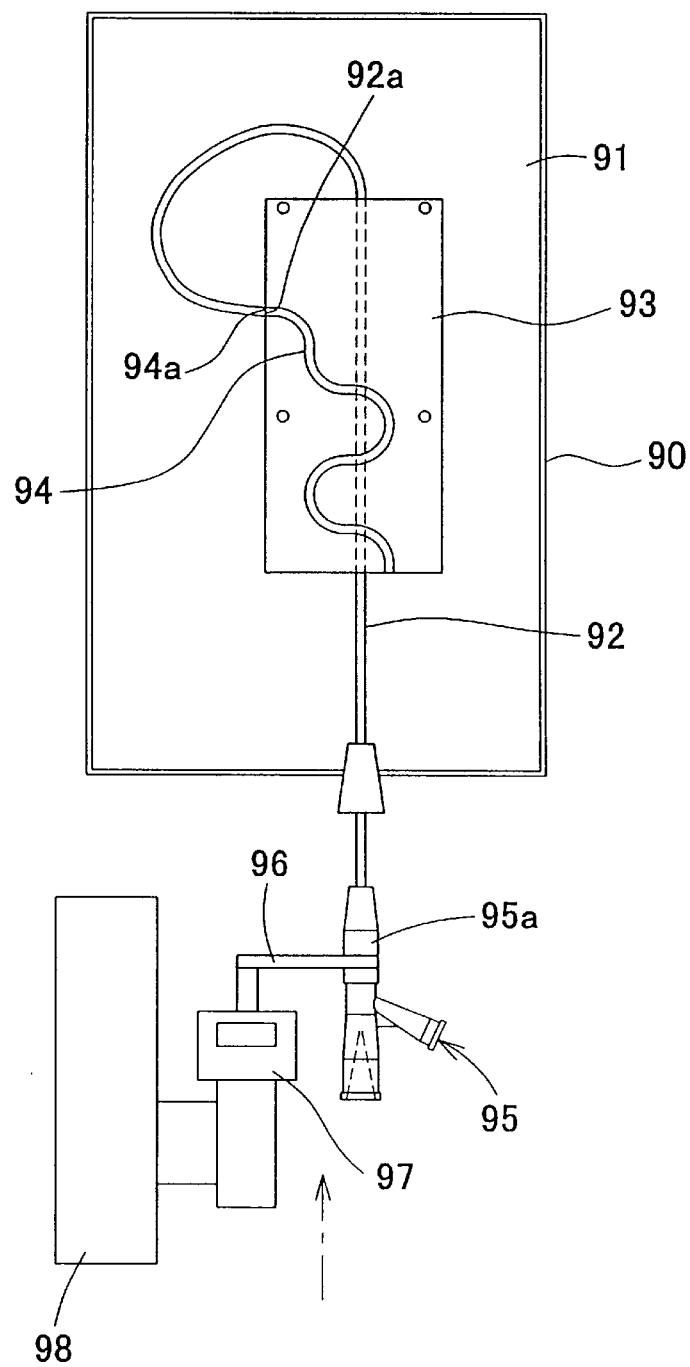
FIG. 16 is a simplified diagram of a test system for testing the controllability of balloon catheters.
Figure 17:
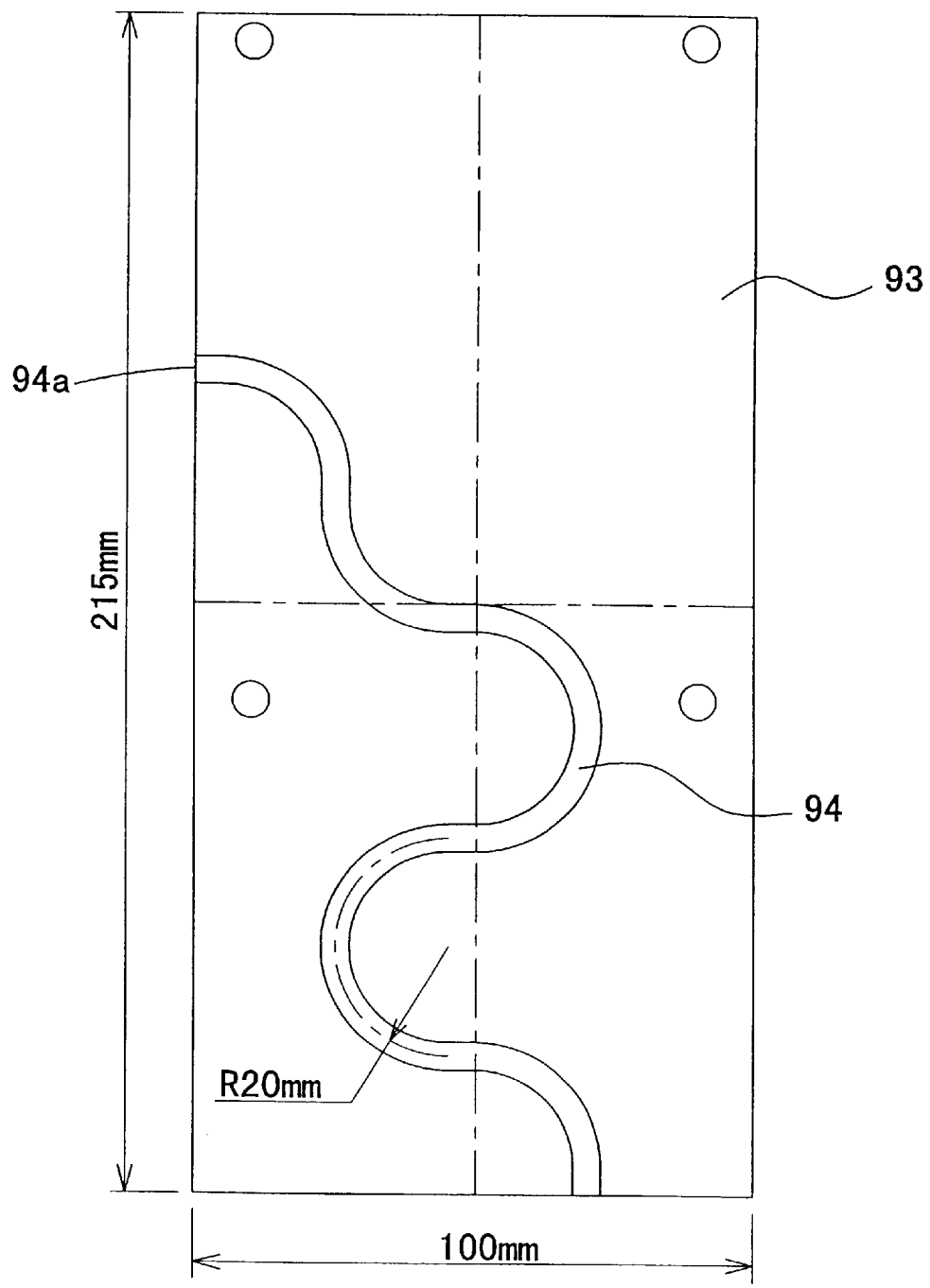
FIG. 17 is a diagram of a polyurethane tube deployment plate and the dimensions thereof.

(4) Test Method 4:

The test system diagrammed in FIG. 16 was prepared. Specifically, a guiding catheter 92 was deployed in a vessel 90 filled with physiological saline solution 91 at 37° C. The distal end 92a of this guiding catheter 92 was linked and made to communicate with the intake end 94a of a polyurethane tube 94 in a deployment plate 93 wherein that polyurethane tube (hereinafter called a PU tube) was deployed in a winding condition. The adapter member 94a of the balloon catheter 95 being evaluated was secured in a holding jig 96. This holding jig 96 is connected to a force gauge 97. The force gauge 97 is supported by a manipulator 98. The manipulator 98 was moved, causing the balloon catheter 95 to advance, and the loads acting on the adapter member 95a were measured when the balloon catheter 95 was pushed ahead inside the polyurethane tube 94 at 20 mm/second, starting at the intake end 94a of the polyurethane tube 94. In FIG. 17, the dimensions of the parts of the deployment plate 93 and polyurethane tube 94 are indicated.

The measurement results based on the test methods 1 to 4 above are given in Table 3 below.

TABLE 3

| Test Method Number | | Embodiment 10 | Embodiment 11 | Comparative Example 3 | Comparative Example 4 |
|---|---|---|---|---|---|
| 1 | Balloon Expansion Pressure (atm) | 0.5 | 0.5 | 0.5 | 5.5 ※2 |
| 2 | Balloon HC Layer Thickness (μm) | 1 | 0 | 1 | 2 |
|   | Tubular Member HC Layer Thickness (μm) | 2 | 2 | 1 | 2 |
| 3 | Balloon Friction Resistance Value (gf) ※1 | 17 | 25 | 20 | — |
|   | Tubular Member Friction Resistance Value (gf) ※1 | 3 | 3 | 20 | — |
| 4 | Resistance Value When Advanced 5 cm Inside PU Tube (gf) | 15 | 30 | 38 | — |
|   | Resistance Value When Advanced 10 cm Inside PU Tube (gf) | 28 | 35 | 40 | — |
|   | Resistance Value When Advanced 15 cm Inside PU Tube (gf) | 37 | 45 | 70 | — |

Note 1: Friction resistance value after 100 strokes.
Note 2: Further evaluation suspended due to failure of hydrophilic coating layer or rupture of balloon.

According to the results given in Table 3, with Comparative Example 4, sticking developed in the folded balloon due to the hydrophilic coating, and the balloon catheter could not be used due to damage to the hydrophilic coating layer and the balloon. With Embodiment 10 and Embodiment 11, however, the expansion pressure when the folded balloon was expanded was sufficiently small (Test Method 1), and neither the coating layer nor the balloon suffered damage. In Embodiments 10 and 11, moreover, as compared to Comparative Example 3, the friction resistance values inside the winding polyurethane tube were small.

It was thus verified that the hydrophilic coating layer on the balloon portion in the embodiments is controlled, and that such problems as inadequate balloon expansion or hydrophilic coating layer failure do not occur. Accordingly, with the balloon catheters relating to the present invention, good controllability can be obtained even in a winding internal passage.

Next, as described earlier, when a metal tubular member is used for a configuring member in a catheter shaft, as in the balloon catheters diagrammed in FIGS. 8 and 9, there are cases where the metal tubular member produces plastic deformation and causes a decline in performance. In the interest of preventing such performance decline, it is preferable to use (1) that wherewith the bending angle produced in the metal tubular member is 15 degrees or less when that metal tubular member is released after being held for 1 minute in a condition wherein it is bent 90 degrees with a radius of curvature that is 50 times the outer diameter thereof, or (2) that wherewith the bending angle produced in the metal tubular member is 30 degrees or less when that metal tubular member is released after being held for 1 minute in a condition wherein it is bent 90 degrees with a radius of curvature that is 35 times the outer diameter thereof, or (3) that wherewith the bending angle produced in the metal tubular member is 35 degrees or less when that metal tubular member is released after being held for 1 minute in a condition wherein it is bent 90 degrees with a radius of curvature that is 25 times the outer diameter thereof.

Figure 18:
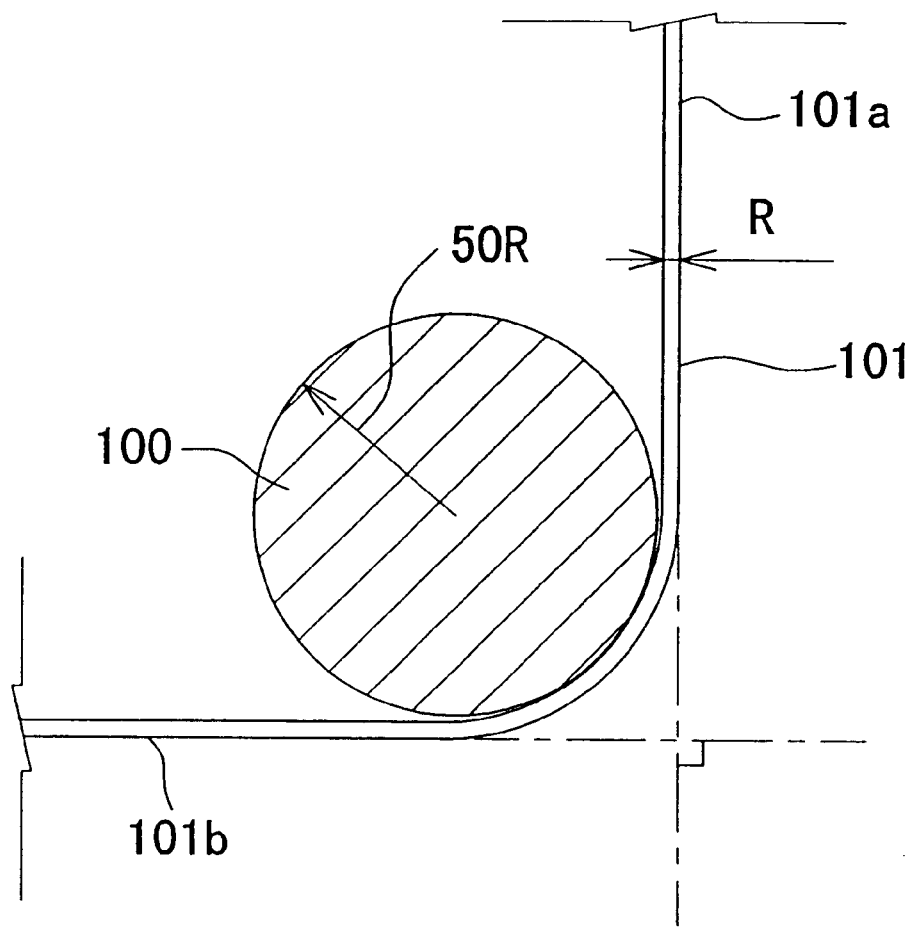
FIG. 18 is a diagram representing a condition wherein a metal tubular member is bent 90 degrees with a modulus of curvature that is 50 times the outer diameter thereof.

In FIG. 18 is diagrammed a condition wherein a metal tubular member 101 has been bent 90 degrees around the circumference of a cylindrical material 100 of radius 50R with a radius of curvature that is 50 times (50R) the outer radius (R) thereof. One end (not shown) of the metal tubular member 101 is secured, and the metal tubular member 101 is bent in the circumferential direction of the cylindrical material 100 having a radius 50R that is 50 times the outer diameter of the metal tubular member 101, being bent so that the angle of intersection between the extensions of the portions 101a and 101b of the metal tubular member 101 that are not bent at that time becomes 90 degrees.

Figure 19:
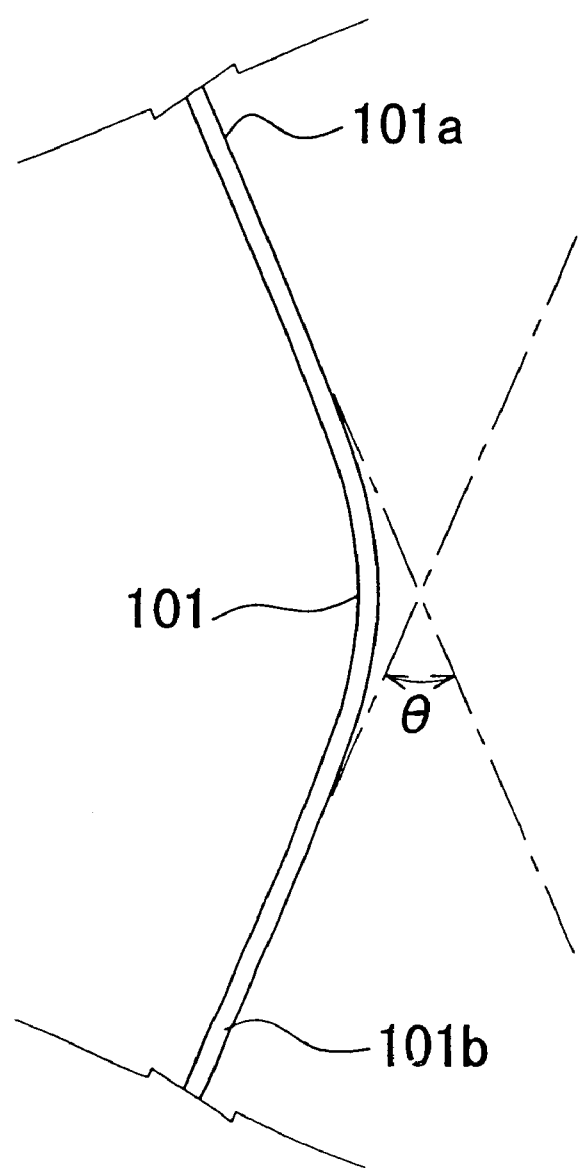
FIG. 19 is a simplified diagram representing the angle of bend in, a metal tubular member.

After that, when the exterior force applied to the metal tubular member 101 relating to the present invention is released, and the angle of intersection between the extensions of the parts 101a and 101b of the naturally deformed metal tubular member 101 that are not bent was measured, that angle of intersection was found to satisfy condition (1) noted above, as diagrammed in FIG. 19.

Similarly, the methods of bending a metal tubular member 90 degrees with a radius of curvature that is 35 times (35R) the outer diameter (R) thereof, and of bending a metal tubular member 90 degrees with a radius of curvature that is 25 times (25R) the outer diameter (R) thereof, follow the method described above and diagrammed in FIG. 18.

There is another common method for evaluating the degree of plastic deformation in a metal tubular member wherewith any point on the metal tubular member is secured, a weight is applied to another point, the bend is held at a certain angle for a certain time and then released, and the elasticity of a hypodermic injection needle of the bending angle which developed in the metal tubular member is examined. When that method is applied, results are obtained which bear a correspondence to the evaluation method of the present invention. Nevertheless, the evaluation method of the present invention is preferable because it yields more stable results.

Various other methods for evaluating plastic deformation exist besides the methods described in the foregoing, but the performance of the metal tubular member corresponds with the evaluation method of the present invention, wherefore it is indicated even with other evaluation methods that metal tubular members based on the present invention are superior.

An example of using stainless steel for the metal tubular member is described below, but there is no particular need to make that a limitation in the present invention, and it is possible to use carbon steel, nickel alloys, nickel-iron alloys, and titanium-nickel alloys and the like, for example, as suitable.

Even if the composition of the metal is identical, the physical properties thereof vary depending on the conditions during processing, wherefore it is necessary to perform processing and make adjustments so that the characteristics of the metal tubular member noted earlier will be exhibited. For example, the properties of stainless steel can be controlled by solid-solution heat treatment, quenching, and tempering. Solid-solution heat treatment and tempering are particularly suitable because strength, hardness, and creep characteristics can be easily controlled by the conditions thereof.

The temperature conditions in solid-solution heat treatment and tempering differ depending on the composition of the steel. In general, however, solid solution and structural recrystallization do not proceed adequately if the temperature is too low, whereas, when the temperature is too high, there is a tendency for strength to diminish due to the coarsening of the crystal grain. Effective temperature ranges exist for each type of steel. In some cases it is advantageous for the present invention to conduct processing with temperature conditions that are on the low side within such ranges. The process temperature, holding time, and cooling speed, which are conditions for solid-solution heat treatment and tempering, are not limited to or by the ranges and numerical values of these embodiments, and should be set in view of the shape and dimensions of the material being heat-treated and the conditions of the surrounding environment so that the characteristics of the metal tubular member noted above are obtained.

Among stainless steels, moreover, those containing molybdenum or titanium are not susceptible to becoming brittle with high-temperature tempering, while, at the same time, the temper softening decline characteristic becomes great, wherefore such steels are preferable because controlling the properties thereof is easier. Among stainless steels containing molybdenum or titanium, AISI No. 316, 316L, 317, 321, 416, 430F, and 430T are preferable in terms of machinability, with 316, 321, and 430F being particularly preferable because of their demonstrated safety when deployed in a living body.

There is no particular limitation on either the deployment position or deployment condition of the metal tubular members described in the foregoing, but in many cases it will be preferable to deploy such on the proximal side of the catheter, relatively speaking. As to the deployment condition, a portion of the catheter may be configured only by the metal tubular member, or the metal tubular member may be present as a core material or reinforcing material. The metal tubular member may also be deployed in a condition wherein the surface thereof is coated with a synthetic resin.

Specific embodiments of balloon catheters wherein the metal tubular members relating to the present invention are used are now described in detail.

EMBODIMENT 12

After forming a tubular member having an outer diameter of 0.70 mm and an inner diameter of 0.59 mm, using 316 stainless steel, by cold drawing, solid-solution heat treatment was performed at approximately 1093° C. with a holding time of 10 minutes, whereupon the metal tubular member used in this embodiment was fabricated. The balloon catheter of Embodiment 12 was then fabricated, employing this metal tubular material in a balloon catheter having the structure diagrammed in FIG. 9.

EMBODIMENT 13

After forming a tube having an outer diameter of 0.70 mm and an inner diameter of 0.59 mm, using 316 stainless steel, by cold drawing, solid-solution heat treatment was performed at approximately 982° C. with a holding time of 10 minutes, whereupon the metal tubular member used in this embodiment was fabricated. The balloon catheter of Embodiment 13 was then fabricated, employing this metal tubular member in a balloon catheter having the structure diagrammed in FIG. 9, as in Embodiment 12.

EMBODIMENT 14

After forming a tube having an outer diameter of 0.70 mm and an inner diameter of 0.59 mm, using 321 stainless steel, by cold drawing, solid-solution heat treatment was performed at approximately 1093° C. with a holding time of 10 minutes, whereupon the metal tubular member used in this embodiment was fabricated. The balloon catheter of Embodiment 14 was then fabricated, employing this metal tubular member in a balloon catheter having the structure diagrammed in FIG. 9, as in Embodiment 12.

EMBODIMENT 15

After forming a tube having an outer diameter of 0.70 mm and an inner diameter of 0.59 mm, using 430F stainless steel, by cold drawing, tempering treatment was performed at approximately 1816° C. with a holding time of 3 minutes, whereupon the metal tubular member used in this embodiment was fabricated. The balloon catheter of Embodiment 15 was then fabricated, employing this metal tubular member in a balloon catheter having the structure diagrammed in FIG. 9, as in Embodiment 12.

COMPARATIVE EXAMPLE 5

After forming a tube having an outer diameter of 0.70 mm and an inner diameter of 0.59 mm, using 304 stainless steel, by cold drawing, solid-solution heat treatment was performed at approximately 1093° C. with a holding time of 10 minutes, whereupon the metal tubular member used in this comparative example was fabricated. The balloon catheter of Comparative Example 5 was then fabricated, employing this metal tubular member in a balloon catheter having the structure diagrammed in FIG. 9, as in Embodiment 12.

COMPARATIVE EXAMPLE 6

A commercially available balloon catheter having a metal tubular member (made of 304 stainless steel, with outer diameter of 0.70 mm and inner diameter of 0.48 mm) as a configuring member of the catheter shaft was taken as Comparative Example 6.

EVALUATION OF EMBODIMENTS 12–15 AND COMPARATIVE EXAMPLES 5 AND 6

The bending angle (θ) described earlier was measured in the metal tubular members (all having outer diameters of 0.70 mm) of Embodiments 12 to 15 and Comparative Examples 5 and 6, described in the foregoing. Specifically, to begin with, each metal tubular member was bent about the circumferential surface of a cylinder having a radius of curvature that was 14.3 times 0.70 mm (=10 mm), and then released after holding that condition for 1 minute, at which time the bending angle (θ) of each naturally deformed metal tubular member was measured.

Similarly, each metal tubular member was bent about the circumferential surface of cylinders having, respectively, radii of curvature 21.4 times the outer diameter (=15 mm), 28.6 times the outer diameter (=20 mm), 35.7 times the outer diameter (=25 mm), 42.9 times the outer diameter (=30 mm), 50 times the outer diameter (=35 mm), 57.1 times the outer diameter (=40 mm), 64.3 times the outer diameter (=45 mm), and 71.4 times the outer diameter thereof (=50 mm), and then released, after holding that condition for 1 minute, at which time the bending angle (θ) of each naturally deformed metal tubular member was measured.

Figure 20:
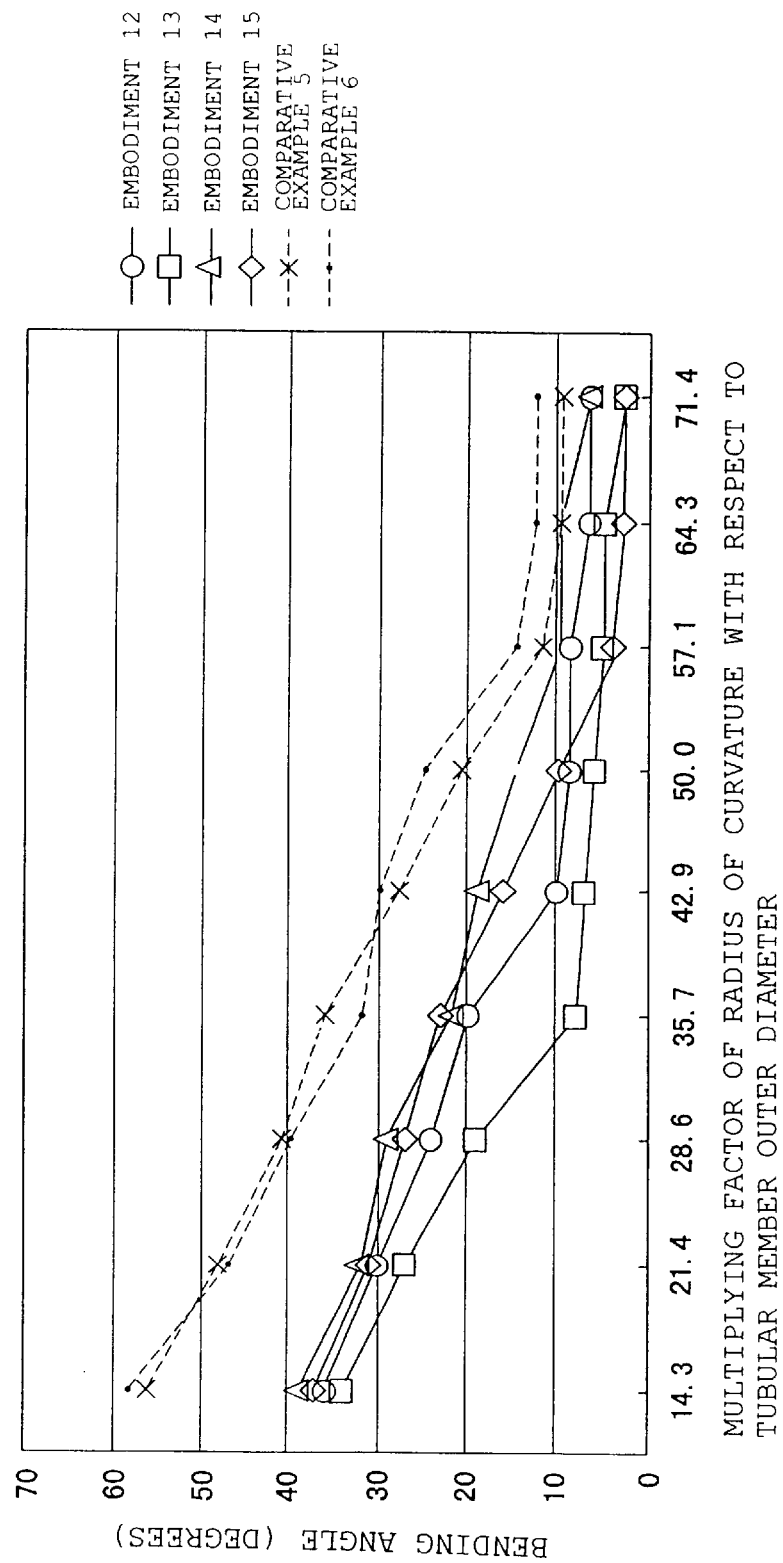
FIG. 20 is a graph representing the relationship between the bending angle and the multiple of the modulus of curvature relative to the outer diameter of a metal tubular member.

Those measurement results are plotted in the graph given in FIG. 20. As indicated in FIG. 20, with Embodiments 12 to 15 relating to the present invention, when bending was done to 90 degrees with a radius of curvature 50 times the outer diameter thereof of 0.70 (=35 mm), that condition held for 1 minute, and then released, the bending angle produced in each metal tubular member was 15 degrees or less. With both Comparative Examples 5 and 6, on the other hand, the bending angle was 20 degrees or greater, indicating that they are more susceptible to plastic deformation than Embodiments 12 to 15.

With Embodiments 12 to 15 relating to the present invention, furthermore, when bending to 90 degrees was done with a radius of curvature 28.6 times the outer diameter thereof of 0.70 mm(=20 mm), that condition held for 1 minute, and then released, the bending angle produced in each metal tubular member was 30 degrees or less.

As the radius of curvature of the cylinder increases, the bending angle produced becomes smaller, wherefore, with Embodiments 12 to 15 relating to the present invention, when bending to 90 degrees was done at a radius of curvature 35 times the outer diameter thereof of 0.70 mm, that condition held for 1 minute, and then released, the bending angle produced in each metal tubular member was 30 degrees or less.

With Comparative Examples 5 and 6, on the other hand, when bending to 90 degrees was done with a radius of curvature 35.7 times the outer diameter thereof of 0.70 mm (=25 mm), that condition held for 1 minute, and released, the bending angle produced in each metal tubular member was greater than 30 degrees. As the radius of curvature of the cylinder decreases, the bending angle produced increases, wherefore, with Comparative Examples 5 and 6, when bending was done to 90 degrees with a radius of curvature 35 times the outer diameter thereof of 0.70 mm, that condition held for 1 minute, and released, the bending angle produced in each metal tubular member was clearly greater than 30 degrees, indicating a greater susceptibility to plastic deformation than Embodiments 12 to 15.

With Embodiments 12 to 15 relating to the present invention, furthermore, when bending to 90 degrees was done with a radius of curvature 21.4 times the outer diameter thereof of 0.70 mm (=15 mm), that condition held for 1 minute, and then released, the bending angle produced in each metal tubular member was 35 degrees or less.

As the radius of curvature of the cylinder increases, the bending angle produced becomes smaller, wherefore, with Embodiments 12 to 15, when bending to 90 degrees was done at a radius of curvature 25 times the outer diameter thereof of 0.70 mm, that condition held for 1 minute, and then released, the bending angle produced in each metal tubular member was 35 degrees or less.

With Comparative Examples 5 and 6, on the other hand, when bending to 90 degrees was done with a radius of curvature 28.6 times the outer diameter thereof of 0.70 mm (=20 mm), that condition held for 1 minute, and released, the bending angle produced in each metal tubular member was greater than 40 degrees. As the radius of curvature of the cylinder decreases, the bending angle produced increases, wherefore, with Comparative Examples 5 and 6, when bending was done to 90 degrees with a radius of curvature 25 times the outer diameter thereof of 0.70 mm, that condition held for 1 minute, and released, the bending angle produced in each metal tubular member was clearly greater than 35 degrees, indicating a greater susceptibility to plastic deformation than Embodiments 12 to 15.

EMBODIMENT 16

Using 316 stainless steel, a tube having an outer diameter of 0.60 mm and inner diameter of 0.45 mm was machined under the same fabrication conditions as in Embodiment 13 to fabricate the metal tubular member used in this embodiment. The balloon catheter of Embodiment 16 was then fabricated, employing this metal tubular member in a balloon catheter having the structure diagrammed in FIG. 9, as in Embodiment 12.

EMBODIMENT 17

Using 321 stainless steel, a tube having an outer diameter of 0.60 mm and inner diameter of 0.45 mm was machined under the same fabrication conditions as in Embodiment 14 to fabricate the metal tubular member used in this embodiment. The balloon catheter of Embodiment 17 was then fabricated, employing this metal tubular member in a balloon catheter having the structure diagrammed in FIG. 9, as in Embodiment 12.

COMPARATIVE EXAMPLE 7

After forming a tube having an outer diameter of 0.60 mm and an inner diameter of 0.45 mm, using 304 stainless steel, by cold drawing, solid-solution heat treatment was performed at approximately 1093° C. with a holding time of 10 minutes, whereupon the metal tubular member used in this comparative example was fabricated.

The balloon catheter of Comparative Example 7 was then fabricated, employing this metal tubular member in a balloon catheter having the structure diagrammed in FIG. 9, as in Embodiment 12.

COMPARATIVE EXAMPLE 8

A commercially available balloon catheter having a metal tubular member (made of 304 stainless steel, with outer diameter of 0.60 mm and inner diameter of 0.45 mm) as a configuring member of the catheter shaft was taken as Comparative Example 8.

EVALUATION OF EMBODIMENTS 16 AND 17 AND COMPARATIVE EXAMPLES 7 and 8

The bending angle (θ) described earlier was measured in the metal tubular members (all having outer diameters of 0.60 mm) of Embodiments 16 and 17 and Comparative Examples 7 and 8, described in the foregoing. Specifically, each metal tubular member was bent about the circumferential surface of cylinders having,. respectively, radii of curvature 16.7 times the outer diameter thereof (0.60 mm) (=15 mm), 25 times the outer diameter (=15 mm), 33.3 times the outer diameter (=20 mm), 37.5 times the outer diameter (=22.5 mm), 41.7 times the outer diameter (=25 mm), 50 times the outer diameter (=30 mm), 58.3 times the outer diameter (=35 mm), 66.7 times the outer diameter (=40 mm), 75 times the outer diameter (=45 mm), and 83.3 times the outer diameter thereof, and then released, after holding that condition for 1 minute, at which time the bending angle (θ) of each naturally deformed metal tubular member was measured.

Figure 21:
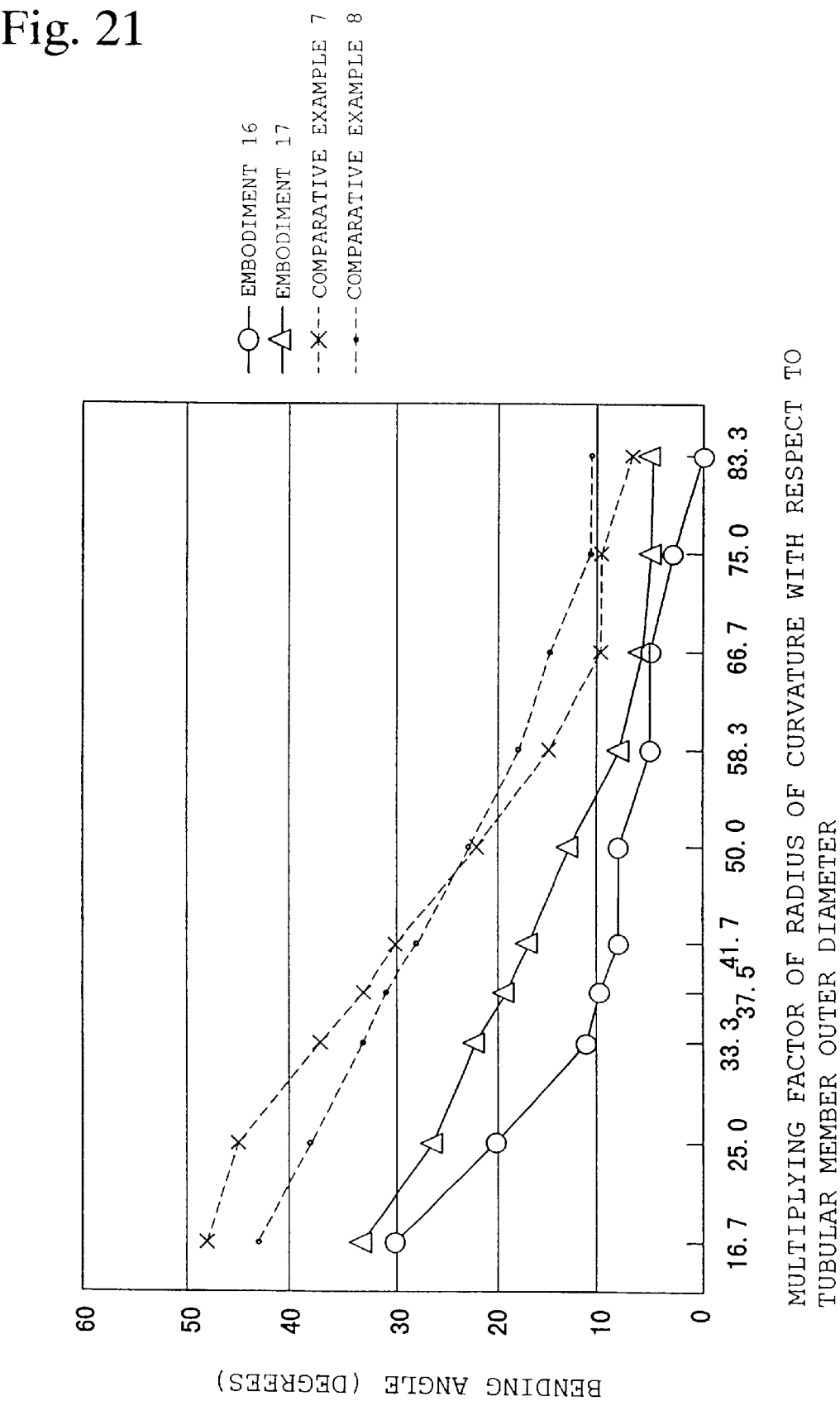
FIG. 21 is a graph representing the relationship between the bending angle and the multiple of the modulus of curvature relative to the outer diameter of a metal tubular member.

Those measurement results are plotted in the graph given in FIG. 21. As indicated in FIG. 21, with Embodiments 16 and 17 relating to the present invention, when bending was done to 90 degrees with a radius of curvature 50 times the outer diameter thereof of 0.60 (=30 mm), that condition held for 1 minute, and then released, the bending angle produced in each metal tubular member was 15 degrees or less. With both Comparative Examples 7 and 8, on the other hand, the bending angle was 20 degrees or greater, indicating that they are more susceptible to plastic deformation than Embodiments 16 and 17.

With Embodiments 16 and 17 relating to the present invention, furthermore, when bending to 90 degrees was done with a radius of curvature 33.3 times the outer diameter thereof of 0.60 mm (=20 mm), that condition held for 1 minute, and then released, the bending angle produced in each metal tubular member was 30 degrees or less.

As the radius of curvature of the cylinder increases, the bending angle produced becomes smaller, wherefore, with Embodiments 16 and 17 relating to the present invention, when bending to 90 degrees was done at a radius of curvature 35 times the outer diameter thereof of 0.60 mm, that condition held for 1 minute, and then released, the bending angle produced in each metal tubular member was 30 degrees or less.

With Comparative Example 7, on the other hand, when bending to 90 degrees was done with a radius of curvature 37.5 times the outer diameter thereof of 0.60 mm (=22.5 mm), that condition held for 1 minute, and released, the bending angle produced in the metal tubular member was 33 degrees. As the radius of curvature of the cylinder decreases, the bending angle produced increases, wherefore, with Comparative Example 7, when bending was done to 90 degrees with a radius of curvature 35 times the outer diameter thereof of 0.60 mm, that condition held for 1 minute, and released, the bending angle produced in the metal tubular member was clearly greater than 30 degrees, indicating a greater susceptibility to plastic deformation than Embodiments 16 and 17.

With Comparative Example 8, when bending to 90 degrees was done with a radius of curvature 37.5 times the outer diameter thereof of 0.60 mm (=22.5 mm), that condition held for 1 minute, and released, the bending angle produced in the metal tubular member was 31 degrees.

As the radius of curvature of the cylinder decreases, the bending angle produced increases, wherefore, with Comparative Example 8, when bending was done to 90 degrees with a radius of curvature 35 times the outer diameter thereof of 0.60 mm, that condition held for 1 minute, and released, the bending angle produced in the metal tubular member was clearly greater than 30 degrees, indicating a greater susceptibility to plastic deformation than Embodiments 16 and 17.

With Embodiments 16 and 17 relating to the present invention, furthermore, when bending to 90 degrees was done with a radius of curvature 25 times the outer diameter thereof of 0.60 mm (=15 mm), that condition held for 1 minute, and then released, the bending angle produced in each metal tubular member was 35 degrees or less.

With Comparative Examples 7 and 8, on the other hand, when bending to 90 degrees was done with a radius of curvature 25 times the outer diameter thereof of 0.60 mm (=15 mm), that condition held for 1 minute, and then released, the bending angle produced in each metal tubular member was 38 degrees or more, indicating a greater susceptibility to plastic deformation than Embodiments 16 and 17.

EMBODIMENT 18

Using 316 stainless steel, a tube having an outer diameter of 1.00 mm and inner diameter of 0.72 mm was machined under fabrication conditions equivalent to those of Embodiment 13 to fabricate the metal tubular member used in this embodiment. This metal tubular member was deployed as the proximal-side tubular member in a balloon catheter having the structure diagrammed in FIG. 14, thus fabricating the balloon catheter of Embodiment 18.

COMPARATIVE EXAMPLE 9

After forming a tube having an outer diameter of 1.00 mm and inner diameter of 0.72 mm by cold drawing, using 304 stainless steel, solid-solution heat treatment was performed at approximately 982° C. with a holding time of 10 minutes to,fabricate the metal tubular member used in this comparative example. Then that tube was deployed as the metal tubular member on the proximal side in a balloon catheter having the structure diagrammed in FIG. 14, as in Embodiment 18, to fabricate the balloon catheter of this comparative example.

EVALUATION OF EMBODIMENT 18 AND COMPARATIVE EXAMPLE 9

The bending angle (θ) described earlier was measured in the metal tubular members (each having an outer diameter of 1.00 mm) of Embodiment 18 and Comparative Example 9, described in the foregoing. Specifically, those metal tubular members were bent about the circumferential surface of cylinders having, respectively, radii of curvature 20 times the outer diameter thereof (1.00 mm) (=20 mm), 25 times the outer diameter (=25 mm), 30 times the outer diameter (=30 mm), 35 times the outer diameter (=35 mm), 40 times the outer diameter (=40 mm), and 50 times the outer diameter (=50 mm), and then released, after holding that condition for 1 minute, at which time the bending angle (θ) of each naturally deformed metal tubular member was measured.

Figure 22:
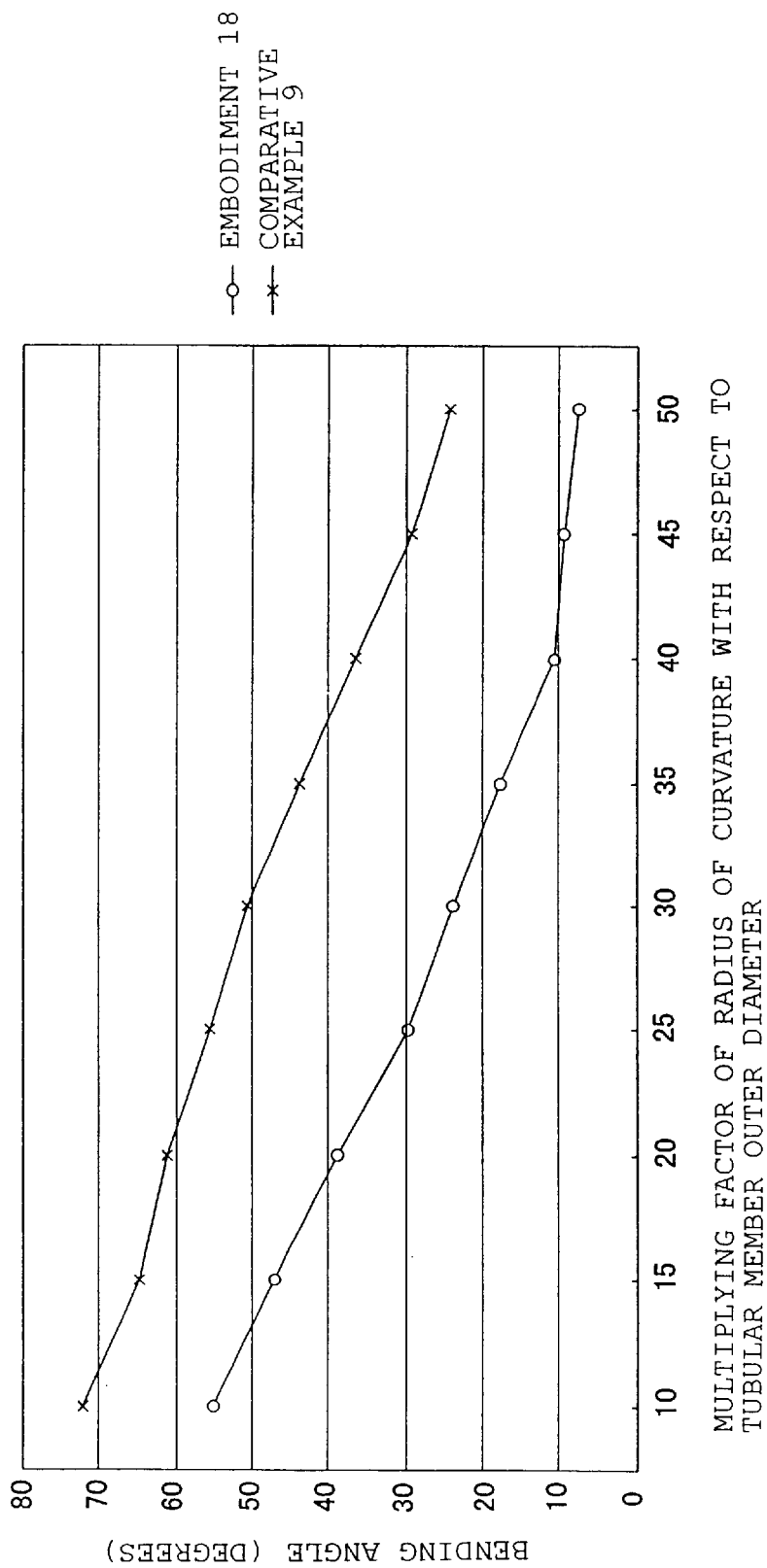
FIG. 22 is a graph representing the relationship between the bending angle and the multiple of the modulus of curvature relative to the outer diameter of a metal tubular member.

Those measurement results are plotted in the graph given in FIG. 22. As indicated in FIG. 22, with Embodiment 18 relating to the present invention, when bending was done to 90 degrees with a radius of curvature 50 times the outer diameter thereof of 1.00 (=50 mm), that condition held for 1 minute, and then released, the bending angle produced in the metal tubular member was 15 degrees or less. With Comparative Example 9, on the other hand, the bending angle was greater than 20 degrees, indicating a greater susceptibility to plastic deformation than Embodiment 18.

With Embodiment 18 relating to the present invention, furthermore, when bending to 90 degrees was done with a radius of curvature 35 times the outer diameter thereof of 1.00 mm (=35 mm), that condition held for 1 minute, and then released, the bending angle produced in each metal tubular member was 30 degrees or less. With Comparative Example 9, on the other hand, the bending angle was greater than 30 degrees, indicating a greater susceptibility to plastic deformation than Embodiment 18.

With Embodiment 18 relating to the present invention, furthermore, when bending to 90 degrees was done with a radius of curvature 25 times the outer diameter thereof of 1.00 mm (=25 mm), that condition held for 1 minute, and then released, the bending angle produced in each metal tubular member was 35 degrees or less. With Comparative Example 9, on the other hand, the bending angle was greater than 35 degrees, indicating a greater susceptibility to plastic deformation than Embodiment 18.

As per the foregoing, Comparative Examples 5 to 9 are susceptible to plastic deformation. Accordingly, in balloon catheters in comparative examples wherein these metal tubular members are employed, the shafts exhibit bending deformation during use and controllability tends to decline.

The metal tubular members of Embodiments 12 to 18, described in the foregoing, are not susceptible to plastic deformation, and balloon catheters of embodiments wherein these metal tubular members are employed do not readily exhibit habitual bending, but exhibit good characteristics with no decline in controllability.

Embodiment aspects of the balloon(s) relating to the present invention are now described.

Figure 23:
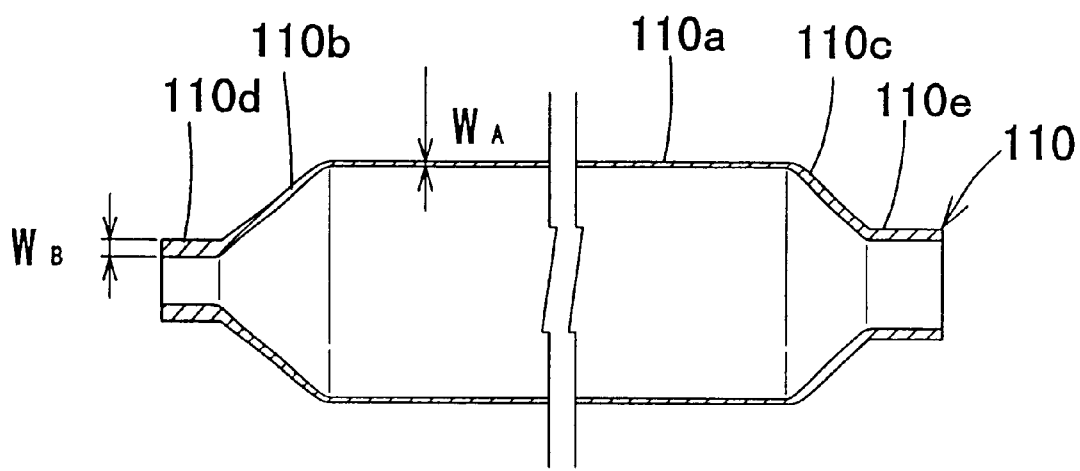
FIG. 23 is a simplified cross-sectional view representing sites for measuring the skin thickness dimensions in a balloon relating to the present invention.

As diagrammed in FIG. 23, the balloon 110 in the first embodiment is configured by a straight tube part 110a that expands or contracts with the induction of a pressurized fluid, a distal-side conical part 110b and a proximal-side conical part 110c the diameters of which narrow toward the outside, formed at either end of the straight tube part 110a, and a cylindrical distal-side sleeve part 110d and cylindrical proximal-side sleeve part 110e formed at the two ends of those conical parts 110b and 110c. It is preferable that such a balloon 110 be such that correspondence relationships are established so that the skin thickness ratio ($W_B/W_A$) between the straight tube part skin thickness ($W_A$) and the sleeve part skin thickness ($W_B$) corresponding to values within a range of nominal expanded diameters of 3.5 mm to 3.0 mm is less than 2.5, the skin thickness ratio ($W_B/W_A$) corresponding to a nominal expanded diameter of 2.5 mm is less than 2.3, the skin thickness ratio ($W_B/W_A$) corresponding to a nominal expanded diameter of 2.0 mm is less than 2.1, and the skin thickness ratio ($W_B/W_A$) corresponding to a nominal expanded diameter of 1.5 mm is less than 2.0. Thus it is possible to optimize the balance between the balloon straight tube part skin thickness and sleeve part skin thickness while imparting adequate pressure withstanding performance to the balloon. With the balloon 110 diagrammed, the straight tube part 110a is indicated as having a perfectly straight tubular shape with a constant outer diameter, but the present invention is not limited thereto or thereby, and the straight tube part may have a slightly tapered shape, or it may be a straight tube part having one or a plurality of constrictions along its length.

Next, the method of manufacturing the balloon 110 is described. For manufacturing the balloon, a blow molding method is adopted to impart sufficient strength against the internal pressure inducted during expansion. More specifically, it is preferable to use a biaxial stretching procedure that stretches a balloon-shaped parison formed by extrusion molding in the axial direction, and then stretches it in the circumferential direction by blowing pressurized air for blow-molding inside the metal mold. Instead of that stretching procedure, in some cases it will be preferable to employ a biaxial stretching procedure wherein, after stretching the parison in the axial direction, an expansion deformation is caused in the circumferential direction, by applying a high internal pressure in a comparatively low-temperature environment, so as to produce an outer diameter that is smaller than the outer diameter of the balloon finally formed, after which the blowing in of the blow-molding pressurized air described above is performed.

Next, in order to prevent deformation or failure, a yet higher internal pressure is introduced into the entire balloon, and, while holding the straight tube part and conical parts in a metal mold, a pulling stretch is applied in the axial direction to the sleeve parts, and, by thinning the walls of those sleeve parts and adjusting the skin thickness, the balloon 110 relating to the present invention is formed. At this time, if the internal pressure applied to the balloon is low, deformation or failure will readily occur in the straight tube part and conical parts of the balloon, and the sleeve part skin thinning will not proceed, wherefore it is necessary to introduce a sufficiently high internal pressure. In order to secure the shape and dimensions of and increase the strength in the balloon, furthermore, after adjusting the skin thickness of the sleeve parts, the balloon may be subjected to a thermal fixing treatment, as necessary. There is no particular limitation on the resin material used in the balloon, but thermoplastic resins, such as a polyethylene terephthalate, polyethylene, polyvinyl acetate, ionomer, vinyl polychloride, polyamide, polyamide-based thermoplastic elastomer, polyester-based thermoplastic elastomer, or polyurethane-based thermoplastic elastomer or the like can be used to good effect. Among these, those which have a Shore hardness of 75D or greater, an elongation of less than 250%, and a glass transition temperature of less than 37° C. are particularly to be preferred because therewith it is easier to pull-stretch the sleeve parts in the axial direction and adjust the skin thickness.

Figure 24:
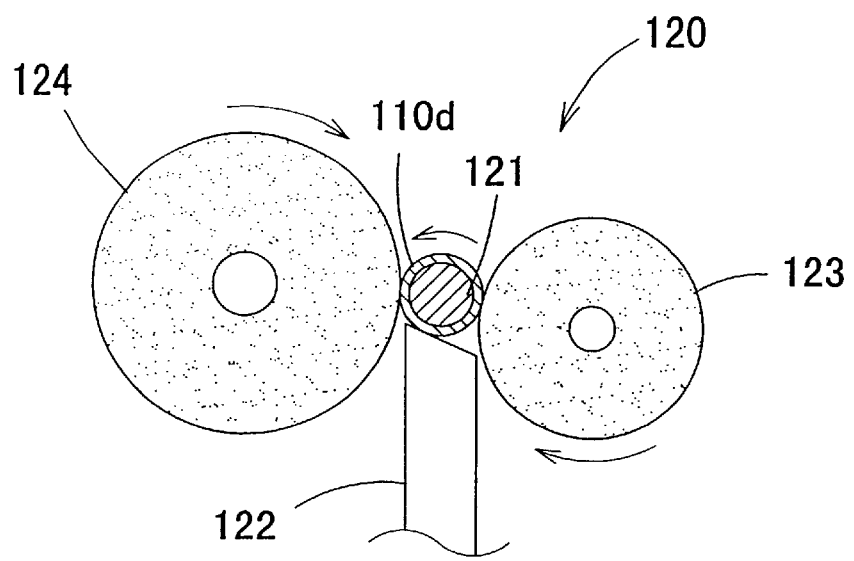
FIG. 24 is a simplified diagram of a centerless grinding apparatus.

Polishing and grinding provide other effective means for making the skin thin in the sleeve parts. Such a grinding procedure is performed, for example, using a centerless grinding apparatus 120 like that diagrammed in FIG. 24. First, the distal-side sleeve part 110d having a core material 121 for supporting the inner diameter inserted in the lumen therein is loaded on a receiving plate 122, and is simultaneously supported from the right by the contact of an adjustment grindstone wheel 123 and from the left by a cutting grindstone wheel 124. In this condition, the outer surface of the sleeve part 110d is ground by causing both the cutting grindstone wheel 124 and the adjustment grindstone wheel 123 to turn clockwise, without supporting the center core of the distal-side sleeve part 110d. At this time, the turning speed of the cutting grindstone wheel 124 is maintained at a higher turning speed than that of the adjustment grindstone wheel 123, and the depth of cutting is suitably determined by the turning speed of the two wheels, the turning speed ratio therebetween, and the amount of feed-in turning of the adjustment grindstone wheel 123. With such a grinding procedure as this, skin thickness adjustment can be performed to high precision even in a comparatively small-diameter tube, and so the procedure may be said to be well suited to balloons for balloon catheters. The thermoplastic resins noted above can be used to good effect as the resin material for the balloons subjected to abrasive and cutting grinding processes.

Figure 25:
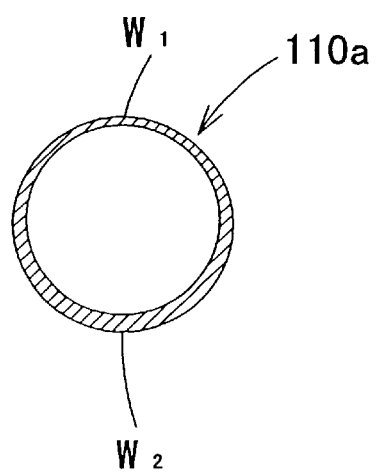
FIG. 25 is a simplified explanatory diagram representing a cross-section of a balloon straight tube part.

Suitable means for examining and measuring the parts of the balloon may be selected as appropriate to the shape of each part. A microgauge may be used for measuring the skin thickness of the straight tube part of the balloon, for example, and an optical microscope or electron microscope for examining or measuring the cross-sections thereof, while a pin gauge may be used for measuring the inner diameter of the sleeve parts of the balloon, a laser measurement instrument for measuring the outer diameter thereof, and an optical microscope for examining or measuring the cross-sections therein. If there is variation between the measured values in these parts, the measured values may be subjected to averaging computations according to the distribution condition thereof. In a case where, for example, the distribution of the skin thicknesses in the balloon straight tube part 110a is such that the skin thickness is maximized at a location $W_2$ axially symmetrical with the location $W_1$ of minimum skin thickness, as indicated in the cross-sectional view of the balloon straight tube part given in FIG. 25, a value intermediate between the minimum skin thickness value and the maximum skin thickness value may be taken as the skin thickness value. For measuring the skin thickness of the distal-side sleeve parts, in general, the skin thickness in the sleeve part tends to take on a distribution-wherein there is little variation in the axial direction, but, when it is joined by fusion to the guide wire passing tube, it is preferable that skin thickness measurements be made near the boundary with the conical part where there is little effect from the fusion.

More specific embodiments of the balloon in the first embodiment described in the foregoing are now described in detail.

EMBODIMENT 19; NOMINAL EXPANDED DIAMETER=3.5 mm

A parison having an outer diameter of 1.09 mm and inner diameter of 0.48 mm was fabricated by an extrusion molding process, using a polyurethane-based thermoplastic elastomer having a Shore hardness of 77.5D, glass transition temperature of −9° C., and extreme elongation of 220%. Next, that parison was stretched by a factor of approximately 1.5 in the axial direction in a metal mold with the temperature adjusted to 55° C., and, by introducing compressed air at approximately 4 MPa into the interior thereof, it was stretched in the circumferential direction until the outer diameter thereof was approximately twice the outer diameter of the original parison. Then the tubular member formed by stretching the parison was loaded into another metal mold having a cylindrical void therein with an inner diameter of approximately 3.5 mm, and, by introducing compressed air at 2.2 MPa into the interior in a temperature environment of approximately 104° C., a balloon was formed. Following thereupon, the pressure of the compressed air noted above was raised to 3.5 MPa, and, while holding the straight tube part and conical parts of the balloon in the same metal mold, the distal-side sleeve part and proximal-side sleeve part were both pull-stretched in the axial direction. Then the balloon of this embodiment (with a nominal expanded diameter of 3.5 mm) was extracted from the cooled metal mold. The dimensions of the balloon In this embodiment were a straight tube part skin thickness ($W_A$) of 0.024 mm, a distal-side sleeve part skin thickness ($W_B$) of 0.058 mm, and a skin thickness ration ($W_B/W_A$) of 2.42.

EMBODIMENT 19; NOMINAL EXPANDED DIAMETER=3.0 mm

A parison having an outer diameter of 0.95 mm and inner diameter of 0.44 mm was fabricated by an extrusion molding process, using a polyurethane-based thermoplastic elastomer having a Shore hardness of 77.5D, glass transition temperature of −9° C., and extreme elongation of 220%. Next, that parison was stretched by a factor of approximately 1.5 in the axial direction in a metal mold with the temperature adjusted to 55° C., and, by introducing compressed air at approximately 3.5 MPa into the interior thereof, it was stretched in the circumferential direction until the outer diameter thereof was approximately twice the outer diameter of the original parison. Then the tubular member formed by stretching the parison was loaded into another metal mold having a cylindrical void therein with an inner diameter of approximately 3.0 mm, and, by introducing compressed air at 2.2 MPa into the interior in a temperature environment of approximately 104° C., a balloon was formed. Following thereupon, the pressure of the compressed air noted above was raised to 3.5 MPa, and, while holding the straight tube part and conical parts of the balloon in the same metal mold, the distal-side sleeve part and proximal-side sleeve part were both pull-stretched in the axial direction. Then the balloon of this embodiment (with a nominal expanded diameter of 3.0 mm) was extracted from the cooled metal mold. The dimensions of the balloon in this embodiment were a straight tube part skin thickness ($W_A$) of 0.021 mm, a distal-side sleeve part skin thickness ($W_B$) of 0.050 mm, and a skin thickness ration ($W_B/W_A$) of 2.38.

EMBODIMENT 19; NOMINAL EXPANDED DIAMETER=2.5 mm

A parison having an outer diameter of 0.80 mm and inner diameter of 0.35 mm was fabricated by an extrusion molding process, using a polyurethane-based thermoplastic elastomer having a Shore hardness of 77.5D, glass transition temperature of −9° C., and extreme elongation of 220%. Next, that parison was stretched by a factor of approximately 1.6 in the axial direction in a metal mold with the temperature adjusted to 55° C., and, by introducing compressed air at, approximately 3.0 MPa into the interior thereof, it was stretched in the circumferential direction until the outer diameter thereof was approximately twice the outer diameter of the original parison. Then the tubular member formed by stretching the parison was loaded into another metal mold having a cylindrical void therein with an inner diameter of approximately 2.5 mm, and, by introducing compressed air at 2.2 MPa into the interior in a temperature environment of approximately 104° C., a balloon was formed. Following thereupon, the pressure of the compressed air noted above was raised to 3.5 MPa, and, while holding the straight tube part and conical parts of the balloon in the same metal mold, the distal-side sleeve part and proximal-side sleeve part were both pull-stretched in the axial direction. Then the balloon of this embodiment (with a nominal expanded diameter of 2.5 mm) was extracted from the cooled metal mold. The dimensions of the balloon in this embodiment were a straight tube part skin thickness ($W_A$) of 0.020 mm, a distal-side sleeve part skin thickness ($W_B$) of 0.045 mm, and a skin thickness ration ($W_B/W_A$) of 2.25.

EMBODIMENT 19; NOMINAL EXPANDED DIAMETER=2.0 mm

A parison having an outer diameter of 0.65 mm and inner diameter of 0.30 mm was fabricated by an extrusion molding process, using a polyurethane-based thermoplastic elastomer having a Shore hardness of 77.5D, glass transition temperature of −9° C., and extreme elongation of 220%. Next, that parison was stretched by a factor of approximately 1.7 in the axial direction in a metal mold with the temperature adjusted to 55° C., and, by introducing compressed air at approximately 2.5 MPa into the interior thereof, it was stretched in the circumferential direction until the outer diameter thereof was approximately twice the outer diameter of the original parison. Then the tubular member formed by stretching the parison was loaded into another metal mold having a cylindrical void therein with an inner diameter of approximately 2.0 mm, and, by introducing compressed air at 2.2 MPa into the interior in a temperature environment of approximately 100° C., a balloon was formed. Following thereupon, the pressure of the compressed air noted above was raised to 3.0 MPa, and, while holding the straight tube part and conical parts of the balloon in the same metal mold, the distal-side sleeve part and proximal-side sleeve part were both pull-stretched in the axial direction. Then the balloon of this embodiment (with a nominal expanded diameter of 2.0 mm) was extracted from the cooled metal mold. The dimensions of the balloon in this embodiment were a straight tube part skin thickness ($W_A$) of 0.018 mm, a distal-side sleeve part skin thickness ($W_B$) of 0.037 mm, and a skin thickness ration ($W_B/W_A$) of 2.06.

EMBODIMENT 19; NOMINAL EXPANDED DIAMETER=1.5 mm

A parison having an outer diameter of 0.50 mm and inner diameter of 0.24 mm was fabricated by an extrusion molding process, using a polyurethane-based thermoplastic elastomer having a Shore hardness of 77.5D, glass transition temperature of −9° C., and extreme elongation of 220%. Next, that parison was stretched by a factor of approximately 1.8 in the axial direction in a metal mold with the temperature adjusted to 55° C., and, by introducing compressed air at approximately 2.5 MPa into the interior thereof, it was stretched in the circumferential direction until the outer diameter thereof was approximately twice the outer diameter of the original parison. Then the tubular member formed by stretching the parison was loaded into another metal mold having a cylindrical void therein with an inner diameter of approximately 1.5 mm, and, by introducing compressed air at 2.2 MPa into the interior in a temperature environment of approximately 100° C., a balloon was formed. Following thereupon, the pressure of the compressed air noted above was raised to 3.0 MPa, and, while holding the straight tube part and conical parts of the balloon in the same metal mold, the distal-side sleeve part and proximal-side sleeve part were both pull-stretched in the axial direction. Then the balloon of this embodiment (with a nominal expanded diameter of 1.5 mm) was extracted from the cooled metal mold. The dimensions of the balloon in this embodiment were a straight tube part skin thickness ($W_A$) of 0.018 mm, a distal-side sleeve part skin thickness ($W_B$) of 0.034 mm, and a skin thickness ration ($W_B/W_A$) of 1.89.

The dimensions of the balloons of Embodiment 19 described above are given in Table 4 further below. The dimensions in the table are indicated as $W_B/W_A$=(skin thickness ratio). This applies also hereafter.

EMBODIMENT 20; NOMINAL EXPANDED DIAMETER=3.5 mm

A parison having an outer diameter of 1.04 mm and inner diameter of 0.52 mm was fabricated by an extrusion molding process, using a polyester-based thermoplastic elastomer having a Shore hardness of 72D, glass transition temperature of 12° C., and extreme elongation of 260%. Next, by subjecting that parison to biaxial stretch blow-molding, a balloon (nominal expanded diameter=3.5 mm) was formed. The dimensions of this balloon were a straight tube part skin thickness of 0.023 mm, and distal-side sleeve part skin thickness of 0.092 mm (outer diameter=0.76 mm). Next, the balloon was mounted in a centerless grinding apparatus, as diagrammed in FIG. 24, in a condition wherein a core material was inserted into the lumen of the distal-side sleeve part of the balloon, that core material having an outer diameter roughly equivalent to the inner diameter of that lumen, and the outer surface of the distal-side sleeve part was subjected to a grinding process until the outer diameter thereof was 0.69 mm. After grinding, the end of that sleeve part was cut so that the ground length became 1.5 mm, whereupon the balloon of this embodiment (nominal expanded diameter=3.5 mm) was fabricated. The dimensions of the balloon of this embodiment were a straight tube part skin thickness ($W_A$) of 0.023 mm, a distal-side sleeve part skin thickness ($W_B$) of 0.057 mm, and a skin thickness ration ($W_B/W_A$) of 2.48.

EMBODIMENT 20; NOMINAL EXPANDED DIAMETER=3.0 mm

A parison having an outer diameter of 0.98 mm and inner diameter of 0.49 mm was fabricated by an extrusion molding process, using a polyester-based thermoplastic elastomer having a Shore hardness of 72D, glass transition temperature of 12° C., and extreme elongation of 260%. Next, by subjecting that parison to biaxial stretch blow-molding, a balloon (nominal expanded diameter=3.0 mm) was formed. The dimensions of this balloon were a straight tube part skin thickness of 0.021 mm, and distal-side sleeve part skin thickness of 0.085 mm (outer diameter=0.77 mm). Next, the balloon was mounted in a centerless grinding apparatus, as diagrammed in FIG. 24, in a condition wherein a core material was inserted into the lumen of the distal-side sleeve part of the balloon, that core material having an outer diameter roughly equivalent to the inner diameter of that lumen, and the outer surface of the distal-side sleeve part was subjected to a grinding process until the outer diameter thereof was 0.70 mm. After grinding, the end of that sleeve part was cut so that the ground length became 1.5 mm, whereupon the balloon of this embodiment (nominal expanded diameter=3.0 mm) was fabricated. The dimensions of the balloon of this embodiment were a straight tube part skin thickness ($W_A$) of 0.021 mm, a distal-side sleeve part skin thickness ($W_B$) of 0.050 mm, and a skin thickness ration ($W_B/W_A$) of 2.38.

The dimensions of the balloons relating to Embodiment 20 described above are given in Table 4 further below.

COMPARATIVE EXAMPLE 10

The skin thicknesses of the straight tube part and distal-side sleeve part of the balloons of balloon catheters using commercially available polyethylene balloons as configuring components, having nominal expanded diameters of 3.5 mm, 3.0 mm, 2.5 mm, 2.0 mm, and 1.5 mm, were measured, and the skin thickness ratios ($W_B/W_A$) thereof were computed. The results are given in Table 4.

COMPARATIVE EXAMPLE 11

The skin thicknesses of the straight tube part and distal-side sleeve part of the balloons of balloon catheters using commercially available polyamide-based thermoplastic elastomer balloons as configuring components, having nominal expanded diameters of 3.5 mm, 3.0 mm, 2.5 mm, 2.0 mm, and 1.5 mm, were measured, and the ratios ($W_B/W_A$) thereof were computed. The results are given in Table 4.

COMPARATIVE EXAMPLE 12

The skin thicknesses of the straight tube part and distal-side sleeve part of the balloons of balloon catheters using commercially available polyurethane-based thermoplastic elastomer balloons as configuring components, having nominal expanded diameters of 3.5 mm, 3.0 mm, 2.5 mm, 2.0 mm, and 1.5 mm, were measured, and the ratios ($W_B/W_A$) thereof were computed. The results are given in Table 4.

EVALUATION OF EMBODIMENTS 19 AND 20 AND COMPARATIVE EXAMPLES 10 AND 11

In evaluating the embodiments and comparative examples described above, the balloon was judged to be more outstanding the smaller the skin thickness ratio ($W_B/W_A$) at each nominal expanded diameter. Referring to Table 4, in the embodiments having nominal expanded diameters of 3.5 mm or 3.0 mm, the skin thickness ratio was 2.5 or below, in those having a nominal expanded diameter of 2.5, the skin thickness ratio was 2.3 or below, in those having a nominal expanded diameter of 2.0 mm, the skin thickness ratio was 2.1 or below, and in those having a nominal expanded diameter of 1.5, the skin thickness ratio was 2.0 or below. In contrast thereto, the comparative examples exhibited larger skin thickness ratios than the embodiments at every nominal expanded diameter, demonstrating their inferiority to the embodiments. The foregoing results indicated that, in the balloons of the embodiments, the skin thickness of the sleeve parts is made sufficiently thin, even when the skin thickness of the straight tube part is optimized with respect to the relationship between ability to withstand pressure and material strength.

Furthermore, rapid exchange balloon catheters having the structure diagrammed in FIG. 28 were fabricated, using the balloons of the embodiments, and evaluated. The distal-side sleeve parts of the balloons were joined to guide wire passing tubes (outer diameter=0.54 mm; inner diameter 0.41 mm) using a polyurethane-based adhesive, so as to allow an average clearance of 0.015 mm. The tips of these balloon catheters exhibited satisfactory flexibility in every case, and it was confirmed that they were outstanding.

Thus, with the balloons in the first embodiment, the leading end tips can be given smaller diameters and enhanced flexibility, after securing pressure withstanding performance in the balloon catheters. These balloons therefore make it possible both to enhance the controllability of the balloon catheters and to enhance the ability thereof to pass through to very difficult and winding lesion sites and sites where the surface resistance is great, such as inside stints.

A second embodiment of the balloon relating to the present invention is next described in detail. The balloon of the second embodiment is formed from a polymer material having a crystallized region, having a crystallinity of no less than 10% and no greater than 40%. Such a balloon is fabricated by subjecting a single-lumen tube (parison) formed by extrusion molding and having an elongation at

TABLE 4

(Sleeve part skin thickness)/(straight tube part skin thickness) = (skin thickness ratio)

| Sample | Nominal Expanded Diameter | | | | |
|---|---|---|---|---|---|
| | 1.5 mm | 2.0 mm | 2.5 mm | 3.0 mm | 3.5 mm |
| Embodiment 19 | 0.034/0.018 = 1.89 | 0.037/0.018 = 2.06 | 0.045/0.020 = 2.25 | 0.050/0.021 = 2.38 | 0.058/0.024 = 2.42 |
| Embodiment 20 | | | | 0.050/0.021 = 2.38 | 0.057/0.023 = 2.48 |
| Comparative example 10 | 0.060/0.029 = 2.07 | 0.076/0.032 = 2.38 | 0.080/0.030 = 2.67 | 0.095/0.032 = 2.97 | 0.102/0.035 = 2.91 |
| Comparative example 11 | 0.039/0.018 = 2.17 | 0.045/0.021 = 2.14 | 0.053/0.020 = 2.65 | 0.060/0.020 = 3.00 | 0.075/0.022 = 3.41 |
| Comparative example 12 | 0.042/0.020 = 2.10 | 0.046/0.020 = 2.30 | 0.062/0.025 = 2.48 | 0.065/0.025 = 2.60 | 0.072/0.027 = 2.67 | the tensile break point of 250 to 450% to biaxial stretch blow molding, and performing an annealing process at a temperature 10° C. to 40° C. higher than the biaxial stretch blow molding temperature, preferably for 40 seconds to 120 seconds. As is well known, the elongation at the tensile break point can be effectively adjusted by changing such conditions as the extraction speed when extrusion-molding the parison, the distance between the die and the water vat, and the extraction speed.

For the polymer material configuring the balloon, it is possible to use one or two or more types of polymer material having a crystallized region such as a polyolefin, polyamide, polyurethane, polyester, polyolefin elastomer, polyamide elastomer, polyurethane elastomer, or polyester elastomer. When the balloon is configured with an elastomer, in particular, the crystallized region (hard segment) in the elastomer and the non-crystallized region (soft segment) coexist, wherefore, in the present invention, crystallinity is defined according to Formula 1 below.

$$\text{Crystallinity (\%)} = P_b/(P_{100} \times (W/100)) \quad \text{Formula 1:}$$

where $P_b$ is the balloon property, $P_{100}$ is the crystallized region (hard segment) homopolymer property, and W is the specific weight (wt. %) of the crystallized region (hard segment) in the balloon.

Various methods are commonly known for measuring crystallinity as described above, including methods that measure density, X-ray diffraction, infrared absorption (IR) and Raman spectrums, and nuclear magnetic resonance (NMR) spectrum. In addition to these, examination by optical microscope, especially by a polarizing microscope, is effective in analyzing the structure and degree of orientation of the crystals, etc. There are also methods that focus on energy changes, such as differential thermal analysis (DTA) and differential scanning calorimetry (DSC). Accordingly, For the balloon property ($P_b$) noted above in Formula 1, it is possible to measure and use such values as density, x-ray diffraction strength, infrared absorption spectrum strength, nuclear magnetic resonance spectrum strength, and crystalline heat of fusion by DTA or DSC, etc.

In calculating the crystallinity as defined in the present invention, the effectiveness of the present invention will not be impaired by using any of the physical properties noted above, but it will probably be well to use the crystalline heat of fusion based on the DTA or DSC in the interest of measurement simplicity.

An example is now given for calculating the crystallinity using the crystalline heat of fusion. In the case of a balloon formed of an elastomer comprising PBT (polybutylene terephthalate) as the crystallized region (hard segment) and PTMG (polytetramethylene glycol) as the non-crystallized region (soft segment), the PBT homopolymer crystalline heat of fusion can be used for $P_{100}$ in Formula 1 given above.

Embodiments of the balloon catheter using the balloon of the second embodiment described in the foregoing are now described specifically and in detail.

EMBODIMENT 21

A balloon catheter having the leading end structure diagrammed in FIG. 29 was fabricated and deemed Embodiment 21. More specifically, for the guide wire passing tube 200, a tube having an inner diameter of 0.42 mm and outer diameter of 0.56 mm was formed by extrusion molding using the high-density polyethylene "HY540" (made by Mitsubishi Chemical Industries Ltd.). For the outside tube 204, a tube, having an inner diameter of 0.71 mm and outer diameter of 0.90mm was formed by extrusion molding using the polyamide elastomer "PEBAX 6333SA00" (made by Toray-DuPont Co., Ltd.). The guide wire passing tube 200 and outside tube 204 so fabricated were deployed in a double concentric tubular form and made the catheter shaft of this embodiment.

A parison having an inner diameter of 0.43 mm and outer diameter of 0.96 mm was also molded by extrusion molding using the polyester-based elastomer "Pelprene S-6001" (made by Toyobo Co., Ltd.) formed from a crystallized region (hard segment) of PBT and a non-crystallized region (soft segment) of a polycaprolactone. By subjecting that parison to biaxial stretch blow molding in a metal mold, a balloon having an outer diameter of 3.0 mm and skin thickness of approximately 18 μm was produced. The elongation at the tensile break point of the parison and the balloon molding conditions are noted in Table 5 given further below.

Next, the crystalline heat of fusion of the molded balloon was measured by differential scanning calorimetry. The crystallinity calculated with Formula 2 below and the balloon characteristics are noted in Table 6 given further below.

$$\text{Crystallinity (\%)} = H_b/(H_{100} \times (W/100)) \quad \text{Formula 2:}$$

where $H_b$ is the balloon crystalline heat of fusion (kJ/mol), $H_{100}$ the homopolymer crystalline heat of fusion (kJ/mol) in the crystallized region (hard segment), and W the specific weight (wt. %) of the crystallized region (hard segment) in the balloon.

The balloon was bonded to the catheter shaft using the two-liquid hardening urethane-based adhesive "UR053" (made by H. B. Fuller Co.), and, after wrapping the balloon portion, it was subjected to EOG sterilization and made the balloon catheter sample in Embodiment 21.

Figure 26:
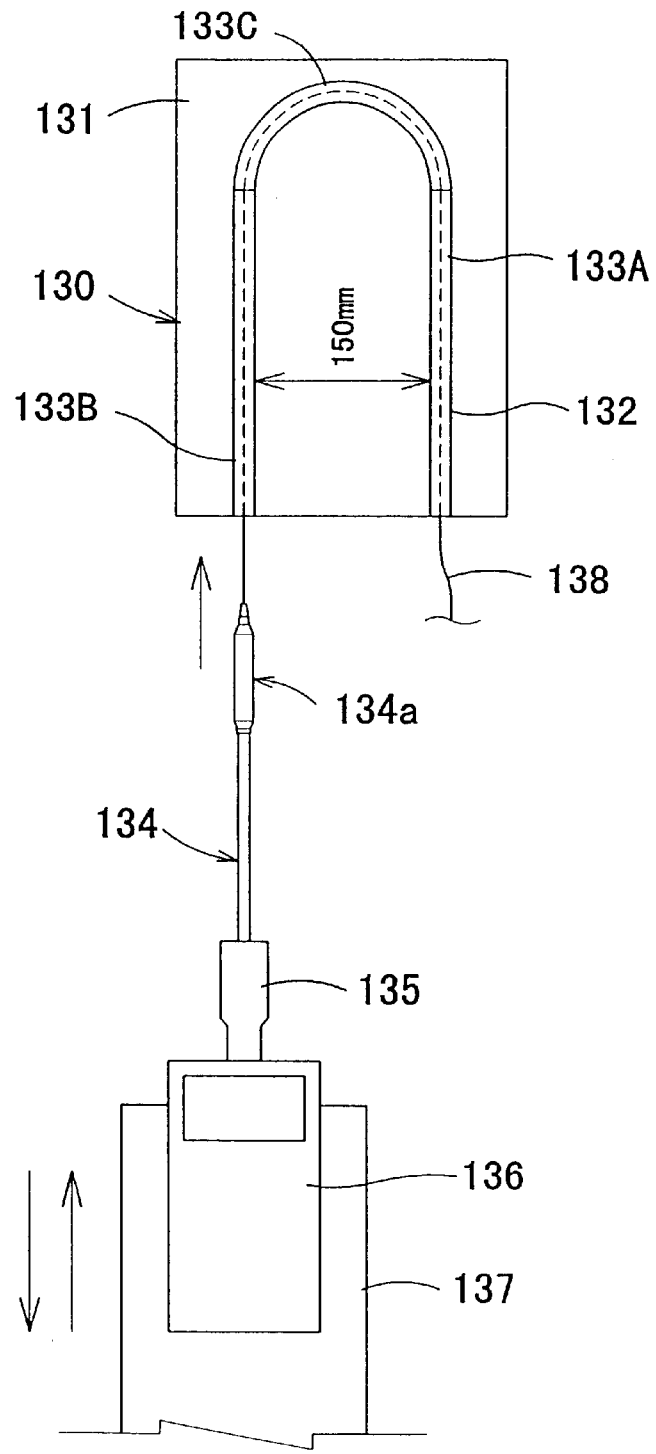
FIG. 26 is a simplified diagram of a vascular plate having a simulated U-shaped curved stricture.

This balloon catheter sample (Embodiment 21) was tested in the test system diagrammed in FIG. 26, that is, it was inserted into a U-shaped curved constricted blood vessel model plate 130 placed in physiological saline solution at 37° C., whereupon the value of the resistance affecting the sample was measured. The results of this measurement are noted in Table 7 given further below. As diagrammed in FIG. 26, the U-shaped curved constricted blood vessel model plate 130 has a U-shaped channel 132 formed on the back side of an acrylic panel 131, with polyethylene tubes 133A and 133B having inner diameters of 3.0 mm deployed along the inside of that U-shaped channel. The curved part of the U-shaped curved constricted blood vessel model was configured by forming a semicircle having a diameter of 150 mm at the inner diameter, and securing a polyethylene tube 133° C. having an inner diameter of 0.95 mm and outer diameter of 2.98 mm concentrically in the curved part of that U-shaped curved constricted blood vessel model.

The balloon catheter sample 134 was connected to a force gauge 136 using a clamp 135, the force gauge 136 was advanced at a speed of 10 mm/sec using a slide table 137, and the maximum resistance value while the balloon 134a was passing through the curved constricted blood vessel model was measured. The measurements were made with n samples with n=3. The measurement values indicated in Table 7 below are average values. When making the measurements, a guide wire 138 was passed into the guide wire passing tube of the catheter 134, and that guide wire 138 was inserted into the interior of the curved constricted blood vessel model beforehand.

Another sample having the same configuration as the balloon catheter samples wherewith the resistance value was measured was placed in a water vat filled with physiological saline solution at 37° C., and the pressure was raised 0.2 ATM at a time using physiological saline solution. The pressure was continually raised, holding each pressure for 1 second, until the balloon failed, to measure the balloon failure pressure. The results are indicated in Table 7 given below. These measurement results are average values where the number of samples n=3.

EMBODIMENT 22

Using a parison made of the same material as in Embodiment 21, a balloon of the same size were produced. The elongation of the parison at the tensile break point and the balloon molding conditions are indicated in Table 5 further below. The results of measuring the crystallinity in the same way as in Embodiment 21 are indicated in Table 6 further below. Catheter samples were produced using the same catheter shafts as in Embodiment 21, and the resistances when inserted into the curved constricted blood vessel model and balloon failure pressures were measured. The results are given in Table 7 further below.

EMBODIMENT 23

A parison having an inner diameter of 0.43 mm and outer diameter of 0.96 mm was molded by extrusion molding the polyamide-based elastomer "PEBAX 7233SA00" (made by Toray-DuPont Co.), configured with Nylon 12 in the crystallized region (hard segment) and PTMG in the non-crystallized region (soft segment). By subjecting that parison to biaxial stretch blow molding in a metal mold, a balloon having an outer diameter of 3.0 mm and skin thickness of approximately 17 μm was produced. The elongation at the tensile break point of the parison and the balloon molding conditions are noted in Table 5 further below. The results of measuring the crystallinity as in Embodiment 21 are noted in Table 6 further below. Catheter samples were fabricated using the same catheter shaft as in Embodiment 21, and the resistance when inserted into the curved constricted blood vessel model and balloon failure pressure were measured. The results are given in Table 7 further below.

EMBODIMENT 24

Using a parison made of the same material as in Embodiment 23, a balloon of the same size were produced. The elongation of the parison at the tensile break point and the balloon molding conditions are indicated in Table 5 further below. The results of measuring the crystallinity in the same way as in Embodiment 21 are indicated in Table 6 further below. Catheter samples were produced using the same catheter shafts as in Embodiment 21, and the resistances when inserted into the curved constricted blood vessel model and balloon failure pressures were measured. The results are given in Table 7 further below.

EMBODIMENT EXAMPLE 13

Using a parison made of the same material as in Embodiment 23, a balloon of the same size were produced. The elongation of the parison at the tensile break point and the balloon molding conditions are indicated in Table 5 further below. The results of measuring the crystallinity in the same way as in Embodiment 21 are indicated in Table 6 further below. Catheter samples were produced using the same catheter shafts as in Embodiment 21, and the resistances when inserted into the curved constricted blood vessel model and balloon failure pressures were measured. The results are given in Table 7 further below.

COMPARATIVE EXAMPLE 14

Using a parison made of the same material as in Embodiment 21, a balloon of the same size were produced. The elongation of the parison at the tensile break point and the balloon molding conditions are indicated in Table 5 further below. The results of measuring the crystallinity in the same way as in Embodiment 21 are indicated in Table 6 further below. Catheter samples were produced using the same catheter shafts as in Embodiment 21, and the resistances when inserted into the curved constricted blood vessel model and balloon failure pressures were measured. The results are given in Table 7 further below.

TABLE 5

| | Elongation at tensile break point of parison (%) | Balloon molding temperature (° C.) | Annealing temperature (° C.) | Annealing time (seconds) |
|---|---|---|---|---|
| Embodiment 21 | 442 | 93.3 | 104.4 | 40 |
| Embodiment 22 | 274 | 93.3 | 132.2 | 100 |
| Embodiment 23 | 333 | 71.1 | 93.3 | 60 |
| Embodiment 24 | 258 | 71.1 | 110.0 | 120 |
| Comparative Example 13 | 506 | 71.1 | 76.7 | 20 |
| Comparative Example 14 | 221 | 93.3 | 143.3 | 120 |

TABLE 6

| | Balloon Material | Crystallized region (Hard Segment) Composition | Non-Crystallized region (Soft Segment) Composition | Crystallized region (Hard Segment) Specific Weight (wt. %) | Crystallinity (%) |
|---|---|---|---|---|---|
| Embodiment 21 | Polyester-based elastomer Pelprene S-6001 | PBT | Polycaprolactone | 87 | 10 |

TABLE 6-continued

|  | Balloon Material | Crystallized region (Hard Segment) Composition | Non-Crystallized region (Soft Segment) Composition | Crystallized region (Hard Segment) Specific Weight (wt. %) | Crystallinity (%) |
|---|---|---|---|---|---|
| Embodiment 22 | Polyester-based elastomer Pelprene S-6001 | PBT | Polycaprolactone | 87 | 38 |
| Embodiment 23 | Polyamide-based elastomer Pebax 7233SA00 | Nylon 12 | PTMG | 88 | 18 |
| Embodiment 24 | Polyamide-based elastomer Pebax 7233SA00 | Nylon 12 | PTMG | 88 | 40 |
| Comparative Example 13 | Polyamide-based elastomer Pebax 7233SA00 | Nylon 12 | PTMG | 88 | 8 |
| Comparative Example 14 | Polyester-based elastomer Pelprene S-6001 | PBT | Polycaprolactone | 87 | 43 |

TABLE 7

|  | Average Maximum Resistance Value When Passing Through Constriction (gf) | Average Failure Pressure (atm) |
|---|---|---|
| Embodiment 21 | 18 | 21.1 |
| Embodiment 22 | 23 | 22.9 |
| Embodiment 23 | 21 | 20.8 |
| Embodiment 24 | 30 | 23.5 |
| Comparative Example 13 | 22 | 15.8 |
| Comparative Example 14 | 55 ※1 | 23.8 |

Note 1:
Measured value for n = 1. In the n = 3 samples, the balloon did not pass in two cases, and the catheter shaft became kinked.

EVALUATION OF EMBODIMENTS 21 TO 24 AND COMPARATIVE EXAMPLES 13 AND 14

In terms of the strength to withstand pressure in the balloon catheters having an expanded diameter of 3.0 mm demanded at medical facilities in recent years, a rated break point (RBP) of at least 14 atm is required in view of the increasingly frequent use with expansion after stent. RBP is usually calculated by Formula 3 given below. In order to satisfy the requirement noted above, a mean break pressure (MBP) of 20 atm or so is necessary.

$$RBP = MBP - (K+1) \times SD \quad \text{Formula 3:}$$

where RBP is the rated break point, MBP the mean break pressure, SD the standard deviation for the mean break pressure, and K a constant determined by reliability, probability, and the number of samples used in computing the mean break pressure.

The lower the value of the resistance when a catheter is advanced to a vascular stricture, the easier it is to make that advance to the stricture, signifying high passability. Physicians implementing the procedure generally judge passability to be high if the resistance value is on the order of 20 gf.

Referring to Table 7, with Embodiments 21 to 24, the maximum resistance during stricture passing is within a range of 18 to 30 gf, whereupon stricture passability is thought to be very high. The mean break pressure is also within a range of 20.8 to 23.5 atm, whereupon it can be judged that the required rated break pressure (of 14 atm) can be realized with any of those embodiments. In short, balloon catheters and thin-skin balloons exhibiting adequate strength to withstand pressure and adequate flexibility are realized.

With Comparative Example 13, on the other hand, although passability is very high in view of the maximum resistance of 22 gf during stricture passage, the mean break pressure is extremely low at 15.8 atm, and it is not possible to attain the rated break pressure of 14 atm. The reason is thought to perhaps be low crystallinity caused by inadequate stretching of the balloon, or even by a low degree of orientation.

With Comparative Example 14, on the other hand, although the mean break pressure of 23.8 atm is adequate, the maximum load during stricture passage is extremely high at 55 gf. In addition, in two cases out of three, the balloon part could not pass the stricture, and kinks developed in the catheter samples. As indicated in Table 6, furthermore, the crystallinity is high at 43%, from which it is conjectured that the cause is that the flexibility possessed by the balloon material was lost.

Accordingly, it is evident that, in the balloons in Embodiments 21 to 24, flexibility to pass through winding strictures and adequate strength to withstand pressure are realized, and that balloon catheters to which those balloons are joined also exhibit adequate flexibility and strength to withstand pressure.

Accordingly, with the balloon catheters having the balloons of the second embodiment, as described in the foregoing, it is possible, by controlling the crystallinity of the balloon, to simultaneously realize flexibility, high strength to withstand pressure, and thinner skin in the balloon part and, as a consequence, it becomes possible to enhance balloon passability in winding strictures.

As described in the foregoing, the balloon catheters and manufacturing methods relating to the present invention are well suited for use in the field of medical treatment when performing therapy or surgery for the purpose of dilating passages in the body, and particularly for use in percutaneous translumin angioplasty.

What is claimed is:

1. A balloon catheter for use in therapy and surgery for purpose of dilation operations, configured by deploying a balloon at the distal end of a catheter shaft, having a guide wire passing tube that passes through interior of said balloon at the distal part of said catheter, and is joined to the distal part of said balloon, wherein there is provided a tension generation means for generating tension in the axial direction in said balloon by applying a force in the axial direction to the distal part of said guide wire passing tube when assembling or using said balloon catheter.

2. The balloon catheter according to claim 1, which is assembled in a condition in which said tension generation means is applying a force in the axial direction to the distal part of said guide wire passing tube, after said guide wire passing tube has been joined to the distal end of said balloon in a condition in which no tension is acting.

3. The balloon catheter according to claim 1, wherein an elastic body incorporated in interior of said balloon catheter is used as said tension generation means.

4. The balloon catheter according to claim 3, wherein said elastic body is a coiled elastic body.

5. The balloon catheter of any one of claim 3, wherein said elastic body is comprised of a metal material.

6. The balloon catheter according to claim 3, having an elastic force transmitting body supported by said elastic body, so that tension is imparted in the axial direction to said balloon by said elastic force transmitting body.

7. The balloon catheter according to claim 6, wherein said elastic force transmitting body comprises, as a configuring component, a linear member that extends to the vicinity of said balloon.

8. The balloon catheter according to claim 7, wherein at least one portion of said linear member has a tapered shape.

9. The balloon catheter according to claim 7, wherein said linear member is joined to one end of a coiled elastic body, and is deployed so as to extend from interior of said coiled elastic body.

10. The balloon catheter according to claim 3, wherein stress generated by displacements in said elastic body is within a range of 5 gf to 200 gf inclusive.

11. The balloon catheter according to claim 10, wherein stress generated by displacements in said elastic body is within a range of 10 gf to 50 gf inclusive.

12. The balloon catheter according to claim 1, wherein said catheter shaft comprises a plurality of tubular members each having at least one lumen, rigidities of proximal part and distal part of said catheter shaft mutually differ, and rigidity of said proximal part is established higher than that of said distal part.

13. The balloon catheter according to claim 12, wherein said catheter shaft comprises a plurality of tubular members each having at least one lumen, rigidities of proximal part and distal part of said catheter shaft mutually differ, said proximal part is formed from a polyimide material as its main component, and said distal part is formed from a polymer material having a lower elastic modulus than said polyimide.

14. The balloon catheter according to claim 12, wherein said catheter shaft comprises a plurality of tubular members each having at least one lumen, rigidities of the proximal part and distal part of said catheter shaft mutually differ, said proximal part is formed from a metal material, and said distal part is formed from a polymer material.

15. The balloon catheter according to claim 12, 13, or 14, wherein a hydrophilic coating is applied to the distal end of said catheter shaft, and the area to be coated with said hydrophilic coating is established to extend to the proximal part of said catheter shaft that contacts said distal part.

16. The balloon Catheter according to claim 12, 13, or 14, wherein a hydrophilic coating is applied to distal end of said catheter shaft, and scope of said hydrophilic coating is established to extend to proximal part of said catheter shaft configured with a larger diameter than said distal part.

17. The balloon catheter according to any one of claims 12 to 14, wherein flexibility of said catheter shaft is made to vary, either in multiple stages or continuously, from the distal part to the proximal part thereof.

18. The balloon catheter according to any one of claims 12 to 14 wherein outer diameter of said catheter shaft is made to vary, either in multiple stages or continuously, from the distal part to the proximal part thereof.

19. The balloon catheter according to claim 1, having a guide wire lumen through which a guide wire is passed and which is formed with a limitation from the distal end of said balloon to midway along the length of said catheter shaft, wherein a hydrophilic coating is applied to the outer surface of said catheter shaft from the leading end of said balloon catheter to a location on the proximal side of the back end opening in said guide wire lumen.

20. The balloon catheter according to claim 19, wherein said hydrophilic coating is applied in a range extending from the most distal end of said balloon catheter towards the proximal side for more than 300 mm.

21. The balloon catheter according to claim 1, wherein a hydrophilic coating is applied to said balloon and catheter shaft in the distal part of said balloon catheter, and the thickness of the hydrophilic coating layer on said catheter shaft is adjusted to be greater than the thickness of the hydrophilic coating layer on said balloon and in vicinity of said balloon.

22. The balloon catheter according to claim 1, wherein a hydrophilic coating is applied at least to the catheter shaft at the distal part of said balloon catheter, and the friction resistance when hydrophilic coating layer on said catheter shaft is wetted is adjusted to be smaller than friction resistance of the balloon and at the vicinity of said balloon.

23. The balloon catheter according to claim 22, wherein said hydrophilic coating is applied only to said catheter shaft at the distal part of said balloon catheter.

24. The balloon catheter according to claim 21 or 22, wherein the thickness of said hydrophilic coating layer on said catheter shaft is 2 $\mu$m or greater.

25. The balloon catheter according to claim 1, wherein a metal tubular member is used for at least one of a plurality of tubular members constituting said catheter shaft, and the bending angle produced in said metal tubular member when released after said metal tubular member was held for 1 minute in a condition where the metal tubular member was bent 90 degrees with a radius of curvature 50 times the outer diameter thereof is 15 degrees or less.

26. The balloon catheter according to claim 1, wherein a metal tubular member is used for at least one of a plurality of tubular members constituting said catheter shaft, and the bending angle produced in said metal tubular member when released after said metal tubular member was held for 1 minute in a condition where the metal tubular member was bent 90 degrees with a radius of curvature 35 times the outer diameter thereof is 30 degrees or less.

27. The balloon catheter according to claim 1, wherein a metal tubular member is used for at least one of a plurality of tubular members constituting said catheter shaft, and bending angle produced in said metal tubular member when released after said metal tubular member was held for 1 minute in a condition where the metal tubular member was bent 90 degrees with a radius of curvature 25 times the outer diameter thereof is 35 degrees or less.

28. The balloon catheter according to any one of claims 25 to 27, wherein metal material of said metal tubular member comprises molybdenum or titanium.

29. The balloon catheter according to any one of claims 25 to 27, wherein a stainless steel selected from among 316 stainless steel, 321 stainless steel, and 430F stainless steel is used for the material of said metal tubular member.

30. The balloon catheter according to claim 1, comprising a balloon having a straight tube part, conical parts which are formed at both ends of said straight tube part, and tapered so that the diameter thereof becomes progressively smaller toward the outside, and cylindrical sleeve parts formed at both ends of said conical parts, wherein skin thickness of said balloon is adjusted so that skin thickness ratio ($W_B/W_A$) between skin thickness of straight tube part ($W_A$) and skin thickness of sleeve part ($W_B$) is less than 2.5 for a balloon nominal expanded diameter of 3.5 mm to 3.0 mm, said skin thickness ratio ($W_B/W_A$) is less than 2.3 for a nominal expanded diameter of 2.5 mm, said skin thickness ratio ($W_B/W_A$) is less than 2.1 for a nominal expanded diameter of 2.0 mm, and said skin thickness ratio ($W_B/W_A$) is less than 2.0 for a nominal expanded diameter of 1.5 mm.

31. The balloon catheter according to claim 30, wherein raw material of said balloon consists of a thermoplastic resin having a Shore hardness greater than 75D, an elongation of less than 250%, and a glass transition temperature of less than 37° C.

32. The balloon catheter according to claim 30 or 31, wherein said balloon is formed by stretching a tubular member constituting the balloon in the axial direction; stretching the same in the circumferential direction by blowing to form said balloon; then mounting the straight tube part and conical parts of said balloon into a metal mold while inducting a higher pressure into interior of said balloon than the pressure applied during stretching in the circumferential direction in order to make skin of sleeve parts thinner; and stretching the sleeve parts in the axial direction.

33. The balloon catheter according to claim 30 or 31, wherein skin of sleeve parts of said balloon is made thinner by polishing or grinding.

34. The balloon catheter according to claim 1, wherein balloon is formed from a polymer material having a crystallized region, and crystallinity of said balloon is adjusted to 10% or more but 40% or less.

* * * * *